US012758548B2

(12) United States Patent
Wang et al.

(10) Patent No.: US 12,758,548 B2
(45) Date of Patent: Oct. 13, 2026

(54) PIPERAZINE DERIVATIVES AND APPLICATION THEREOF

(71) Applicant: GUANGZHOU BAIYUNSHAN PHARMACEUTICAL HOLDINGS CO., LTD. BAIYUNSHAN PHARMACEUTICAL GENERAL FACTORY, Guangzhou (CN)

(72) Inventors: Jiansong Wang, Guangzhou (CN); Zhibo Luo, Guangzhou (CN); Fei Qin, Guangzhou (CN); Wei Wei, Shanghai (CN); Zhigan Jiang, Shanghai (CN); Zhixiang Pan, Shanghai (CN); Yingxia Bao, Guangzhou (CN); Haiying He, Shanghai (CN); Haiwen Huang, Guangzhou (CN); Shuhui Chen, Shanghai (CN)

(73) Assignee: GUANGZHOU BAIYUNSHAN PHARMACEUTICAL HOLDINGS CO., LTD. BAIYUNSHAN PHARMACEUTICAL GENERAL FACTORY, Guangzhou (CN)

( * ) Notice: Subject to any disclaimer, the term of this patent is extended or adjusted under 35 U.S.C. 154(b) by 406 days.

(21) Appl. No.: 18/557,580

(22) PCT Filed: Apr. 22, 2022

(86) PCT No.: PCT/CN2022/088615
§ 371 (c)(1),
(2) Date: Oct. 26, 2023

(87) PCT Pub. No.: WO2022/228317
PCT Pub. Date: Nov. 3, 2022

(65) Prior Publication Data

US 2024/0238281 A1 Jul. 18, 2024

(30) Foreign Application Priority Data

Apr. 27, 2021 (CN) ........................ 202110461572.X
Jul. 27, 2021 (CN) ........................ 202110853038.3
Oct. 20, 2021 (CN) ........................ 202111223627.X
Dec. 13, 2021 (CN) ........................ 202111521983.X

(51) Int. Cl.
*A61K 31/496* (2006.01)
*C07D 401/14* (2006.01)
*C07D 403/06* (2006.01)
*C07D 403/14* (2006.01)
*C07D 405/14* (2006.01)

(52) U.S. Cl.
CPC .......... *A61K 31/496* (2013.01); *C07D 401/14* (2013.01); *C07D 403/06* (2013.01); *C07D 403/14* (2013.01); *C07D 405/14* (2013.01)

(58) Field of Classification Search
CPC .. A61K 31/496; C07D 401/14; C07D 403/06; C07D 403/14; C07D 405/14
See application file for complete search history.

(56) References Cited

U.S. PATENT DOCUMENTS

2015/0087673 A1 3/2015 Hitoshi et al.

FOREIGN PATENT DOCUMENTS

CN 101115732 A 1/2008
WO WO-2004078716 A1 * 9/2004 ............... A61P 3/10
WO 2005040109 A1 5/2005

OTHER PUBLICATIONS

Patani, G. A., LaVoie, E. J.; Chemical Reviews, v96, pp. 3147-3176; 1996 (Year: 1996).*
Tran, et al.; Bioorganic & Medicinal Chemistry Letters, v17, pp. 5165-5170; 2007 (Year: 2007).*
Tran, Joe A. et al., "Pyrrolidines as potent functional agonists of the human melanocortin-4 receptor," Bioorganic & Medicinal Chemistry Letters, 2007, 17(18), pp. 5165-5170.
Jiang, Wanlong et al., "Synthesis and characterization of pyrrolidine derivatives as potent agonists of the human melanocortin-4 receptor," Bioorganic & Medicinal Chemistry Letters, 2007, 17(23), pp. 6546-6552.
International Search Report for PCT/CN2022/088615, mailed Jul. 20, 2022.
Written Opinion of the International Searching Authority for PCT/CN2022/088615, mailed Jul. 20, 2022.
First Office Action for CN Application No. 202280031358.3, mailed Jun. 30, 2025, pp. 1-11.
First search for CN Application No. 202280031358.3, mailed Jun. 30, 2025, pp. 1-4.
Second Office Action for CN Application No. 202280031358.3, mailed Jan. 21, 2026, pp. 1-14.
European search opinion for EP Application No. 22794788, mailed Aug. 8, 2024, pp. 1-5.
Supplementary European search report for EP Application No. 22794788, mailed Aug. 28, 2024, p. 1.
Notice of Reasons for Refusal for JP Application No. 2023565550, mailed Oct. 8, 2024, pp. 1-6.

(Continued)

*Primary Examiner* — Jeffrey S Lundgren
*Assistant Examiner* — W. Justin Youngblood
(74) *Attorney, Agent, or Firm* — Hoffmann & Baron, LLP

(57) ABSTRACT

A class of piperazine derivatives and application thereof, specifically compound represented by formula (III) or pharmaceutically acceptable salt thereof.

(III)

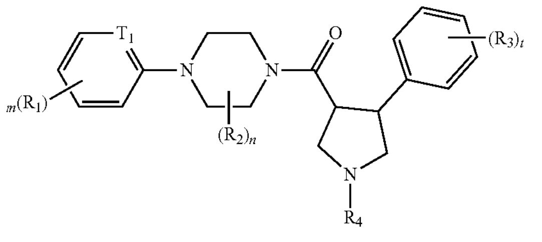

17 Claims, No Drawings

(56) References Cited

OTHER PUBLICATIONS

Decision to Grant a Patent for JP Application No. 2023565550, mailed Apr. 15, 2025, pp. 1-5.
Search Report by Registered Search Organization for JP Application No. 2023565550, , Sep. 12, 2024, pp. 1-30.
Chen Chen et al., "Identification and characterization of pyrrolidine diastereoisomers as potent functional agonists and antagonists of the human melanocortin-4 receptor", Bioorganic & Medicinal Chemistry Letters, 2008, available online Nov. 4, 2007, vol. 18, pp. 129-136.
Moon-Kook Jeon et al., "Promising Strategies for Obesity Pharmacotherapy: Melanocortin-4 (MC-4) Receptor Agonists and Melanin Concentrating Hormone (MCH) Receptor-1 Antagonists", Current Topics in Medicinal Chemistry, 2009, vol. 9, No. 6, pp. 504-538.
Jinfa Ying et al., "Design, Synthesis, and Biological Evaluation of New Cyclic Melanotropin Peptide Analogues Selective for the Human Melanocortin-4 Receptor", Journal of Medicinal Chemistry, 2006, published on Web Oct. 19, 2006, vol. 49, No. 23, pp. 6888-6896.

* cited by examiner

PIPERAZINE DERIVATIVES AND APPLICATION THEREOF

CROSS-REFERENCE TO RELATED APPLICATIONS

The present application is a national phase entry under 35 USC § 371 of International Application No. PCT/CN2022/088615, filed Apr. 22, 2022, which claims the benefit of, and priority to Chinese Patent Application No. 202110461572.X, filed Apr. 27, 2021; Chinese Patent Application No. 202110853038.3 filed Jul. 27, 2021; Chinese Patent Application No. 202111223627.X, filed Oct. 20, 2021; and Chinese Patent Application No. 202111521983.X, filed Dec. 13, 2021, the entire disclosures of which are incorporated herein by reference.

TECHNICAL FIELD

The present disclosure relates to the field of medical technology, and in particular, to a class of piperazine derivatives and use thereof, specifically to compounds of formula (III) and pharmaceutically acceptable salts thereof.

BACKGROUND

Melanocortin receptors belong to a subfamily of G-protein coupled receptors (GPCRs). Currently, five receptor subtypes in the melanocortin family have been cloned and characterized, i.e. MC1R, MC2R, MC3R, MC4R and MC5R, respectively, which are distributed in different tissues. They are receptors for endogenous agonists such as MSH. After activation, they can initiate their downstream cAMP signal transduction pathways and mediate a wide range of physiological functions. Among them, melanocortin 1 receptor (MC1R) is mainly expressed in melanocytes, monocytes and mast cells to mediate pigmentation of hair and skin and block inflammation. MC2R is expressed in adipocytes and adrenal cells to mediate steroidogenesis in the adrenal gland. MC3R is found in the brain, hypothalamus, heart, intestine, and placenta and is associated with energy homeostasis and inflammation. MC5R is found in a wide range of tissues and is thought to function in the exocrine gland system. MC4R is uniquely expressed in the brain and controls feeding behavior, energy homeostasis, and erectile function. MC4R-deficient mice and human exhibit a severe obesity phenotype. Synthetic MC4R agonists have been reported to have a variety of biological effects. Previously, a series of synthetic peptides and peptide analogs are developed based on endogenous agonists such as MSH. NDP-MSH is a non-selective agonist that acts simultaneously on MC1R, MC3R, MC4R and MC5R and has been reported to be capable of reducing food intake and weight gain in rat models. Cyclic heptapeptide MT-II is another agonist with non-selective properties, which has been demonstrated to have therapeutic use for the treatment of erectile dysfunction in clinical trials. Bremelanotide (BMT) is a cyclic 7-amino acid melanocortin peptide that has agonistic effects on MC1R, MC3R, and MC4R, it was approved by FDA for the treatment of a sexual desire disorder in premenopausal women in June 2019. Setmelanotide is a polypeptide-based selective MC4R agonist that was approved by FDA in July 2020 for the treatment of genetic obesity caused by POMC, PCSK1 or LEPR deficiency. These studies have opened up a new chapter for MC4R-targeted drugs. However, the above studies are all related to polypeptide-based molecules, which have shortcomings such as poor target selectivity and inability to take orally. Therefore, the research on small-molecule selective MCR agonists is of great significance in the art.

SUMMARY

The present disclosure provides compounds of formula (III) below or pharmaceutically acceptable salt thereof, which are selected from:

(III)

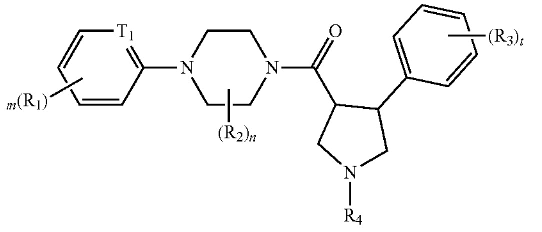

wherein, each $R_1$ is independently selected from halogen, $C_{1-3}$ alkyl, $C_{1-3}$ alkoxyl, —C(═O)$NR_aR_b$ and —$CH_2C$(═O)$NR_aR_b$, the $C_{1-3}$ alkyl and the $C_{1-3}$ alkoxyl are optionally substituted by 1, 2 or 3 halogens;

each $R_2$ is independently selected from $C_{1-3}$ alkyl and $C_{3-6}$ cycloalkyl;

each $R_3$ is independently selected from halogen, $C_{1-3}$ alkyl and $C_{1-3}$ alkoxyl;

$R_4$ is selected from $C_{1-4}$ alkyl, phenyl, $C_{3-6}$ cycloalkyl, 4-8 membered heterocycloalkyl and 5-6 membered heteroaryl, wherein said $C_{1-4}$ alkyl, phenyl, $C_{3-6}$ cycloalkyl, 4-8 membered heterocycloalkyl and 5-6 membered heteroaryl are independently optionally substituted by 1, 2 or 3 $R_c$;

$R_a$ and $R_b$ are each independently selected from H and $C_{1-3}$ alkyl;

each $R_c$ is independently selected from halogen, —CN and $C_{1-3}$ alkyl;

m, n and t are each independently selected from 0, 1 and 2;

$T_1$ is selected from N and CH; and the "hetero" in the "4-8 membered heterocycloalkyl" or "5-6 membered heteroaryl" means 1, 2, 3 or 4 heteroatoms or heteroatom groups independently selected from O, NH, S and N.

In some embodiments of the present disclosure, the $R_a$ and $R_b$ are each independently selected from H and —$CH_3$, and other variables are as defined in the present disclosure.

In some embodiments of the present disclosure, each of the aforementioned $R_1$ is independently selected from F, Cl, —$CF_3$, —C(═O)$NHCH_3$ and —$CH_2C$(═O)$NHCH_3$, and other variables are as defined in the present disclosure.

In some embodiments of the present disclosure, the aforementioned structural unit

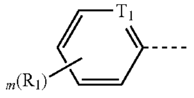

is selected from

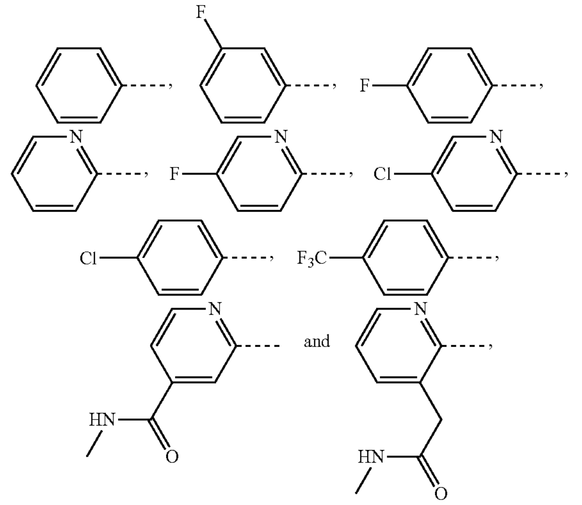

and other variables are as defined in the present disclosure.

In some embodiments of the present disclosure, each of the aforementioned $R_2$ is independently selected from —$CH_3$ and cyclopropyl, and other variables are as defined in the present disclosure.

In some embodiments of the present disclosure, each of the aforementioned $R_3$ is independently selected from F, Cl and Br, and other variables are as defined in the present disclosure.

In some embodiments of the present disclosure, each of the aforementioned Re is independently selected from —CN and —$CH_3$, and other variables are as defined in the present disclosure.

In some embodiments of the present disclosure, the aforementioned $R_4$ is selected from tert-butyl, phenyl, pyridyl, pyridazinyl, tetrahydropyranyl, cyclobutyl, cyclohexyl, tetrahydrofuranyl and oxabicyclooctyl, wherein said tert-butyl, phenyl, pyridyl, pyridazinyl, tetrahydropyranyl, cyclobutyl, cyclohexyl, tetrahydrofuranyl and oxabicyclooctyl are independently optionally substituted by 1, 2 or 3 $R_c$, and other variables are as defined in the present disclosure.

In some embodiments of the present disclosure, the aforementioned $R_4$ is selected from

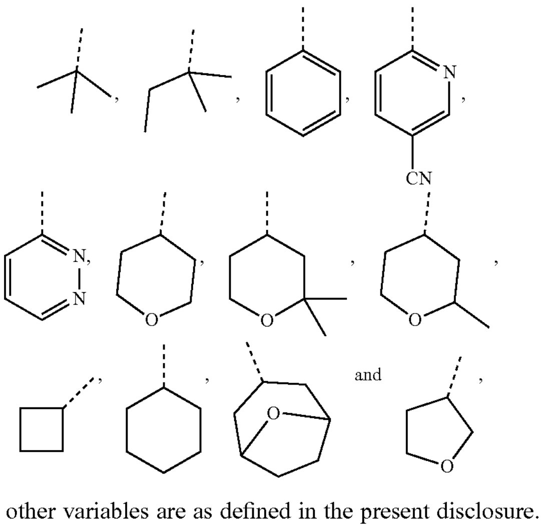

and other variables are as defined in the present disclosure.

The present disclosure provides compounds of formula (III) below or pharmaceutically acceptable salts thereof, which are selected from:

(III)

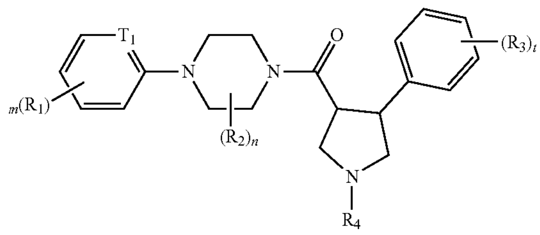

wherein, each $R_1$ is independently selected from halogen, $C_{1-3}$ alkyl, $C_{1-3}$ alkoxyl, —C(═O)$NR_aR_b$ and —$CH_2C$(═O)$NR_aR_b$, the $C_{1-3}$ alkyl and the $C_{1-3}$ alkoxyl are each independently optionally substituted by 1, 2 or 3 halogens;

each $R_2$ is independently selected from $C_{1-3}$ alkyl and $C_{3-6}$ cycloalkyl;

each $R_3$ is independently selected from halogen, $C_{1-3}$ alkyl and $C_{1-3}$ alkoxyl;

$R_4$ is selected from $C_{1-4}$ alkyl, phenyl, 5-6 membered heterocycloalkyl and 5-6 membered heteroaryl, the $C_{1-4}$ alkyl, phenyl, 5-6 membered heterocycloalkyl and 5-6 membered heteroaryl are independently optionally substituted by 1, 2 or 3 $R_c$;

$R_a$ and $R_b$ are each independently selected from H and $C_{1-3}$ alkyl;

each $R_c$ is independently selected from halogen, CN;

m, n and t are each independently selected from 0, 1 and 2;

$T_1$ is selected from N and CH; and the "hetero" in the "5-6 membered heterocycloalkyl" or "5-6 membered heteroaryl" means 1, 2, 3 or 4 heteroatoms or heteroatom groups independently selected from O, NH, S and N.

In some embodiments of the present disclosure, the aforementioned $R_a$ and the aforementioned $R_b$ are each independently selected from H and —$CH_3$, and other variables are as defined in the present disclosure.

In some embodiments of the present disclosure, each of the aforementioned $R_1$ is independently selected from F, Cl, —$CF_3$, —C(═O)$NHCH_3$ and —$CH_2C$(═O)$NHCH_3$, and other variables are as defined in the present disclosure.

In some embodiments of the present disclosure, the aforementioned structural unit

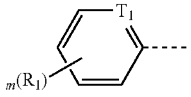

is selected from

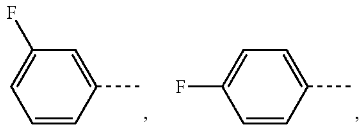

-continued

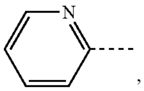, 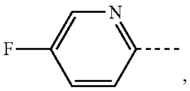,

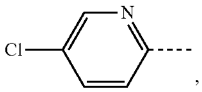, 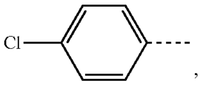,

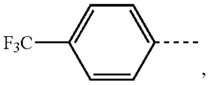, 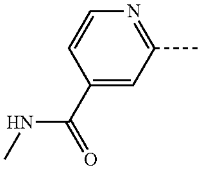 and

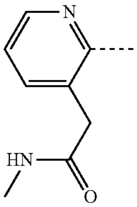, and other variables are as defined in the present disclosure.

In some embodiments of the present disclosure, each of the aforementioned $R_2$ is independently selected from $-CH_3$ and cyclopropyl, and other variables are as defined in the present disclosure.

In some embodiments of the present disclosure, each of the aforementioned $R_3$ is independently selected from F, Cl and Br, and other variables are as defined in the present disclosure.

In some embodiments of the present disclosure, the aforementioned $R_4$ is selected from tert-butyl, phenyl, pyridyl, pyridazinyl and tetrahydropyranyl that are independently optionally substituted by 1, 2 or 3 $R_c$, and other variables are as defined in the present disclosure.

In some embodiments of the present disclosure, the aforementioned $R_4$ is selected from

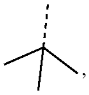, 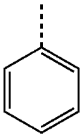, 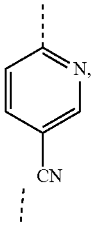

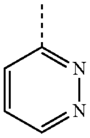 and 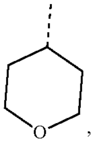, and other variables are as defined in the present disclosure.

The present disclosure provides compounds of formula (II) below or pharmaceutically acceptable salts thereof, which are selected from:

(II)

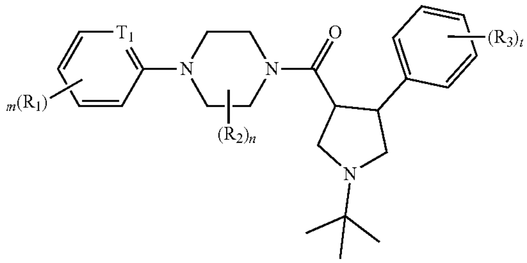

wherein, each $R_1$ is independently selected from halogen, $C_{1-3}$ alkyl, $C_{1-3}$ alkoxyl, $-C(=O)NR_aR_b$ and $-CH_2C(=O)NR_aR_b$;

each $R_2$ is independently selected from $C_{1-3}$ alkyl;

each $R_3$ is independently selected from halogen, $C_{1-3}$ alkyl and $C_{1-3}$ alkoxyl;

$R_a$ and $R_b$ are each independently selected from H and $C_{1-3}$ alkyl;

m, n and t are each independently selected from 0, 1 and 2; and $T_1$ is selected from CH and N.

In some embodiments of the present disclosure, the aforementioned $R_a$ and $R_b$ are each independently selected from H and $-CH_3$, and other variables are as defined in the present disclosure.

In some embodiments of the present disclosure, each of the aforementioned $R_1$ is independently selected from F, Cl, $-C(=O)NHCH_3$ and $-CH_2C(=O)NHCH_3$, and other variables are as defined in the present disclosure.

In some embodiments of the present disclosure, the aforementioned structural unit

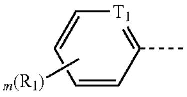

is selected from

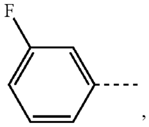, 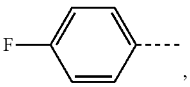, 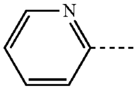,

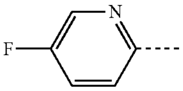, 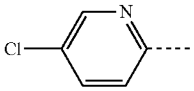,

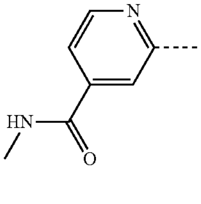 and 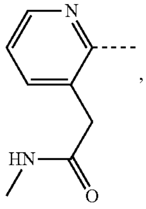, and other variables are as defined in the present disclosure.

In some embodiments of the present disclosure, each of the aforementioned $R_2$ is independently selected from $-CH_3$, and other variables are as defined in the present disclosure.

In some embodiments of the present disclosure, each of the aforementioned $R_3$ is independently selected from F and Cl, and other variables are as defined in the present disclosure.

The present disclosure provides compounds of formula below or pharmaceutically acceptable salts thereof, which are selected from:

(I)

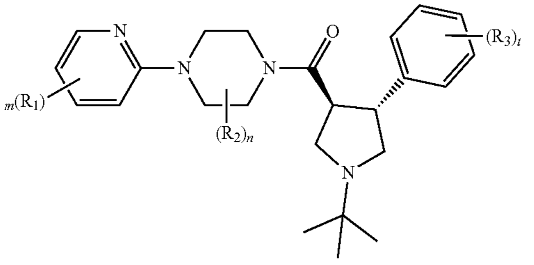

wherein, each $R_1$ is independently selected from halogen, $C_{1-3}$ alkyl, $C_{1-3}$ alkoxyl, —C(═O)$NR_aR_b$ and —$CH_2C$(═O)$NR_aR_b$;

each $R_2$ is independently selected from $C_{1-3}$ alkyl;

each $R_3$ is independently selected from halogen, $C_{1-3}$ alkyl and $C_{1-3}$ alkoxyl;

$R_a$ and $R_b$ are each independently selected from H and $C_{1-3}$ alkyl; and m, n and t are each independently selected from 0, 1 and 2.

In some embodiments of the present disclosure, the aforementioned $R_a$ and $R_b$ are each independently selected from H and —$CH_3$, and other variables are as defined in the present disclosure.

In some embodiments of the present disclosure, each of the aforementioned $R_1$ is independently selected from F, Cl, —C(═O)$NHCH_3$ and —$CH_2C$(═O)$NHCH_3$, and other variables are as defined in the present disclosure.

In some embodiments of the present disclosure, the aforementioned structural unit

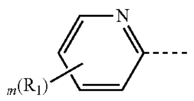

is selected from

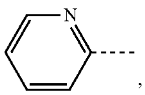
,
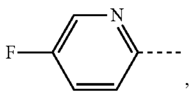
,
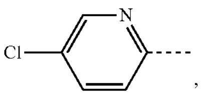
,
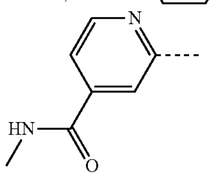
and
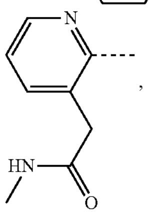
, and other variables are as defined in the present disclosure.

In some embodiments of the present disclosure, each of the aforementioned $R_2$ is independently selected from —$CH_3$, and other variables are as defined in the present disclosure.

In some embodiments of the present disclosure, each of the aforementioned $R_3$ is independently selected from F and Cl, and other variables are as defined in the present disclosure.

In some embodiments of the present disclosure, for the compounds or pharmaceutically acceptable salts thereof, the compounds are selected from:

(I)

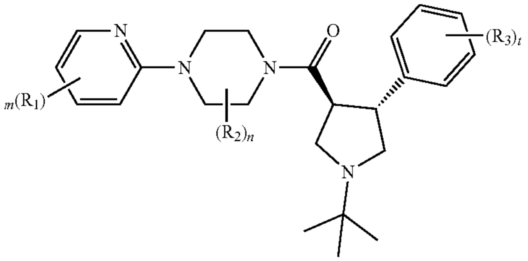

(II-1)

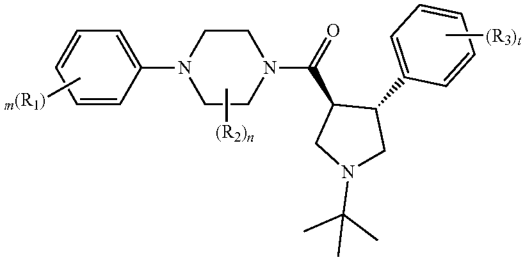

(II-2)

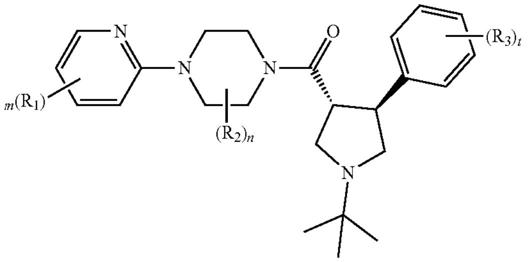

(II-3)

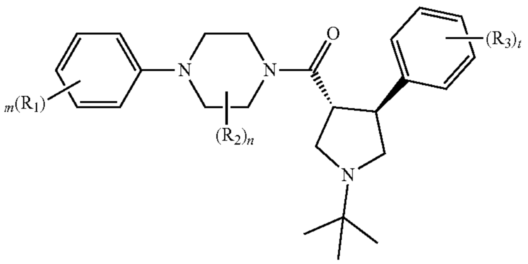

wherein, $R_1$, $R_2$, $R_3$, m, n and t are as defined in the present disclosure.

In some embodiments of the present disclosure, for the compounds or pharmaceutically acceptable salts thereof, the compounds are selected from:

(III-1)
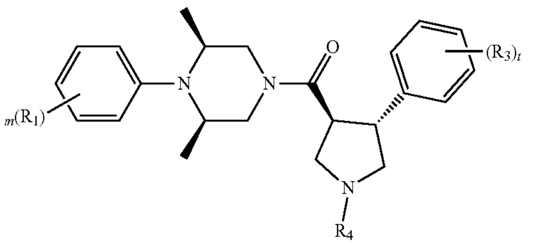
(III-2)
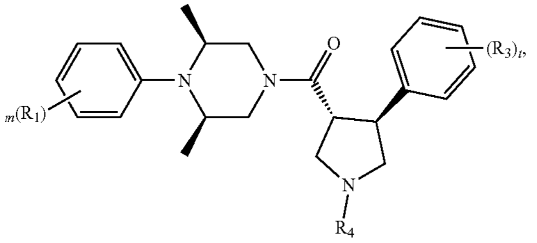
wherein, $R_1$, $R_3$, $R_4$, m and t are as defined in the present disclosure.
Some embodiments of the present disclosure are derived from any combination of the aforementioned variables.
The present disclosure further provides the following compounds or pharmaceutically acceptable salts thereof, which are selected from:
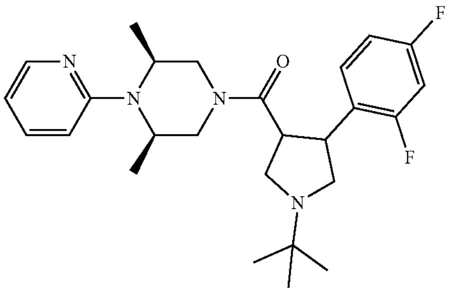
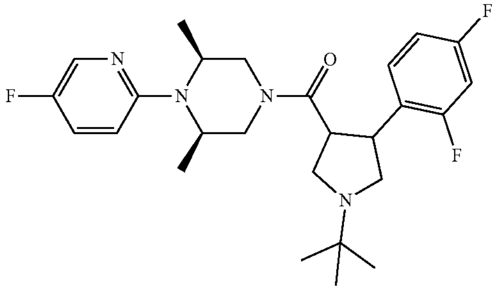
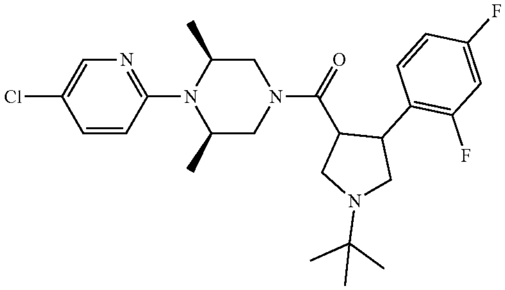
-continued
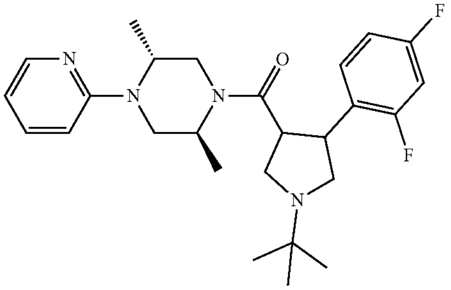
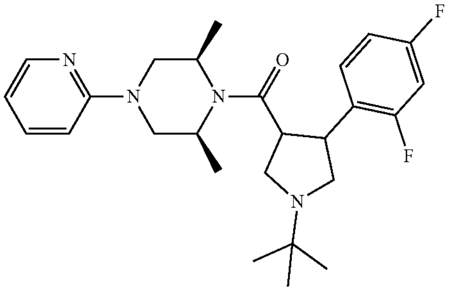
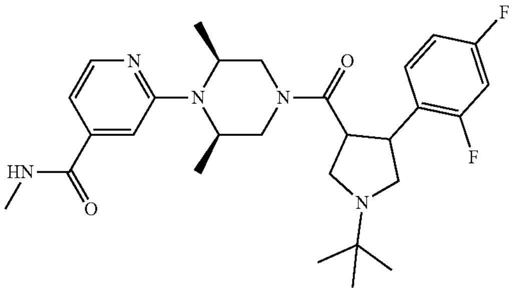
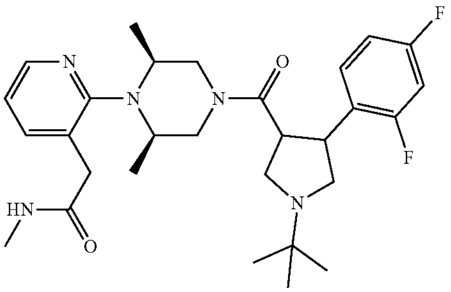
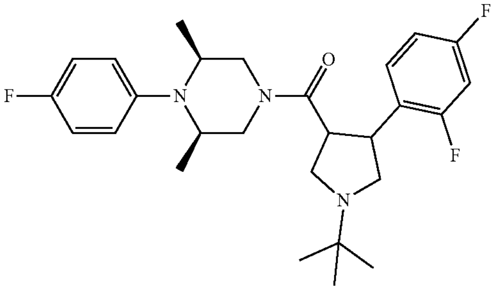

-continued
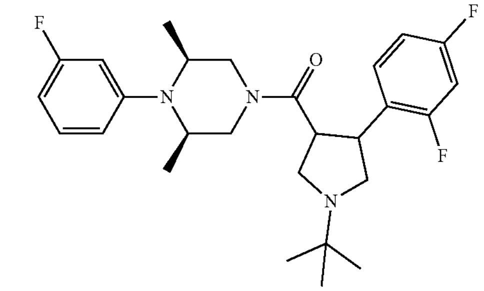
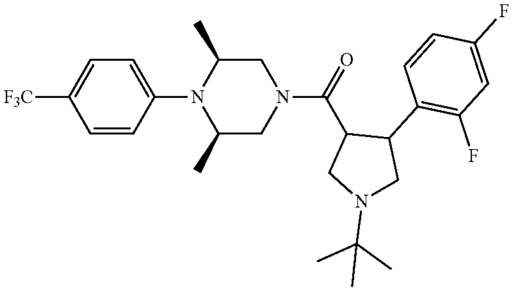
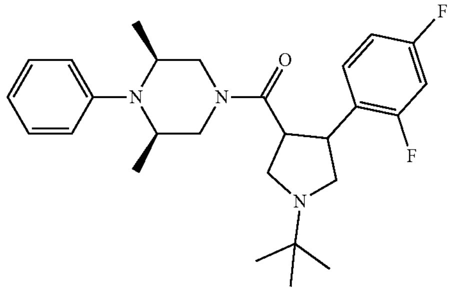
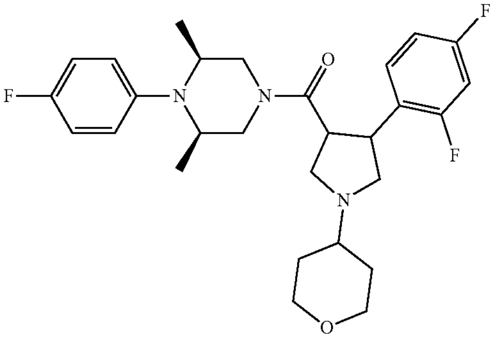
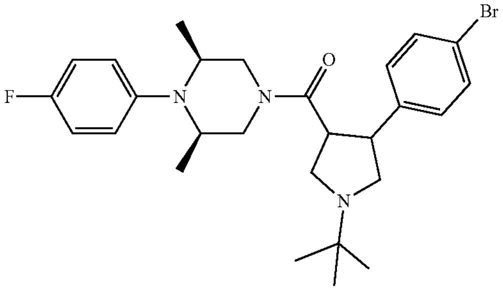
-continued
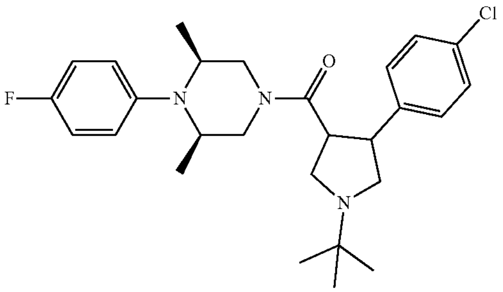
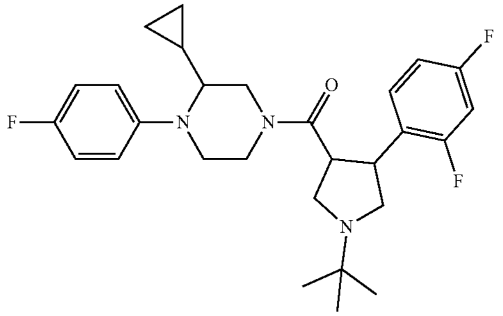
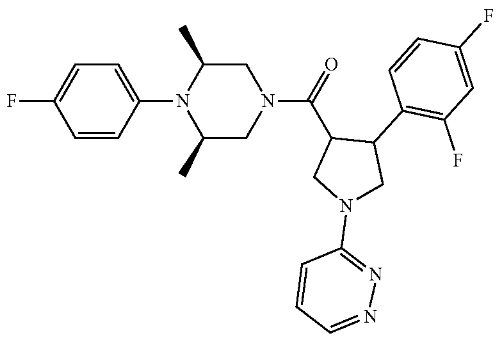
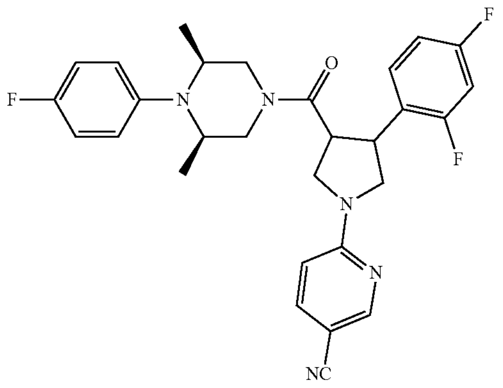
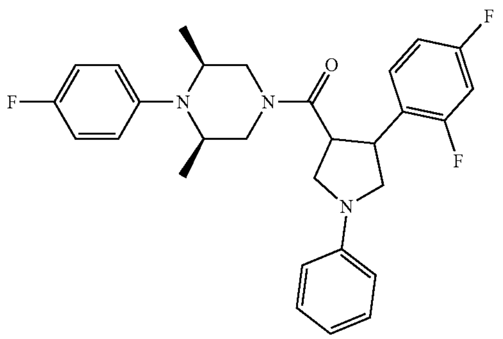

-continued
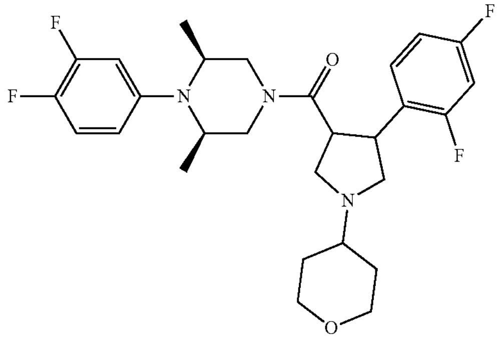
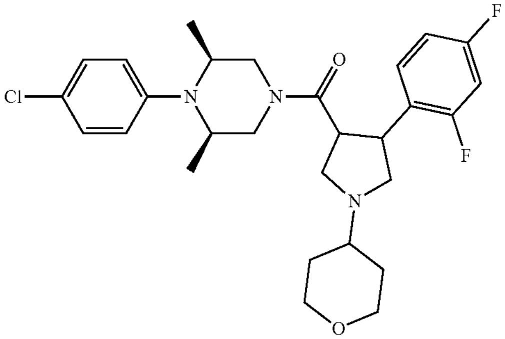
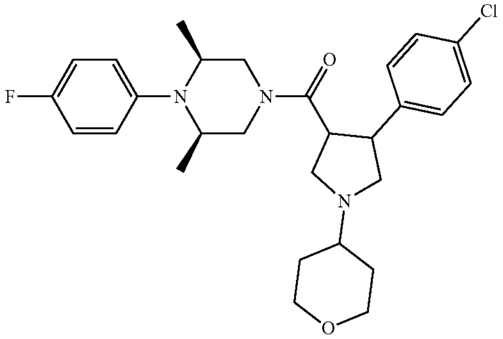
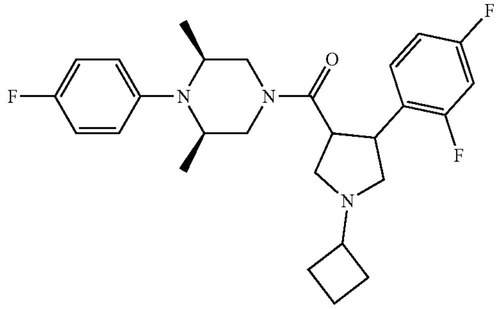
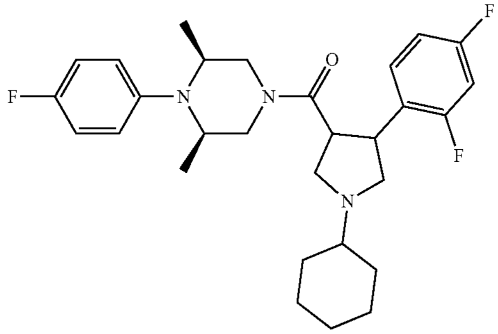
-continued
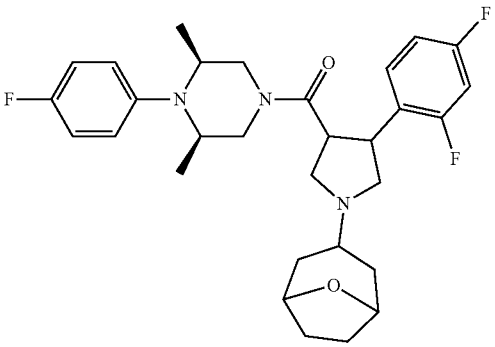
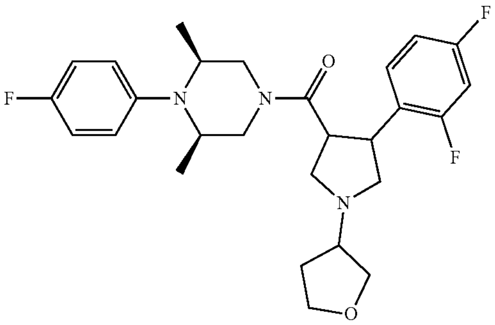
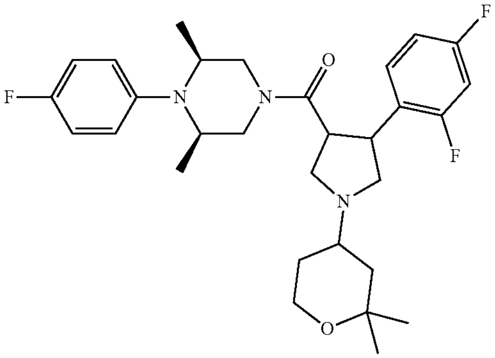
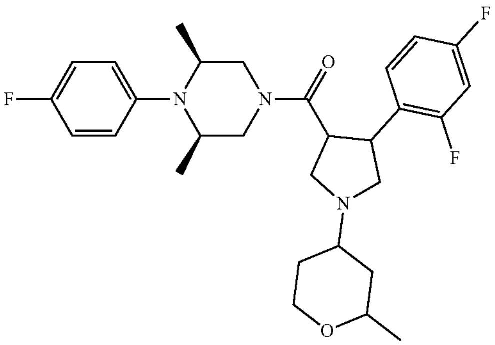
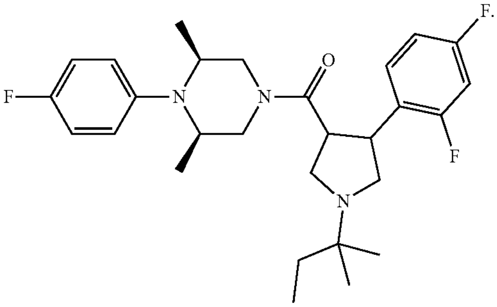 [SMILES: CCC(C)(C)N1CC(C(=O)N2C[C@@H](C)N(c3ccc(F)cc3)[C@@H](C)C2)C(c2ccc(F)cc2F)C1]

The present disclosure further provides the following compounds or pharmaceutically acceptable salts thereof, which are selected from:
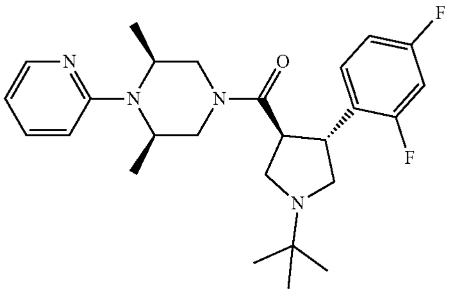
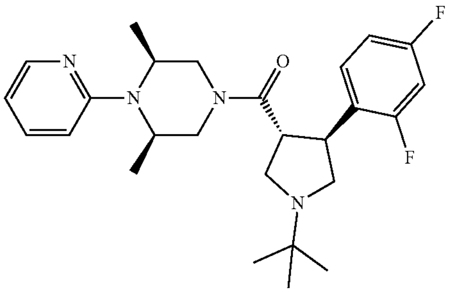
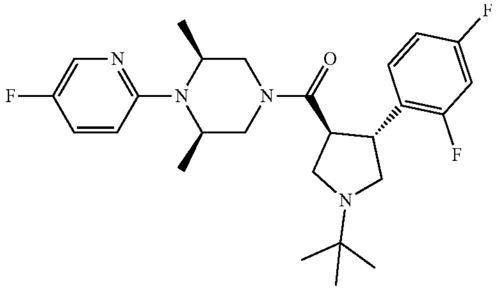
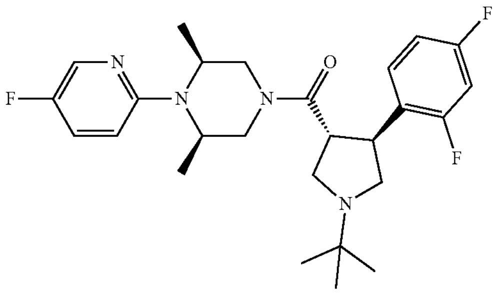
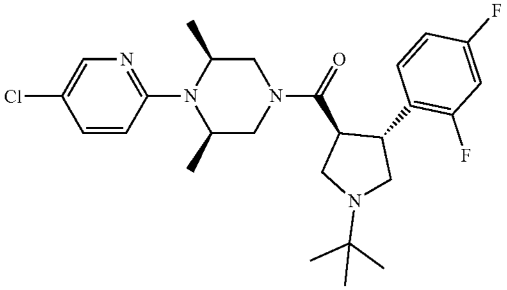
-continued
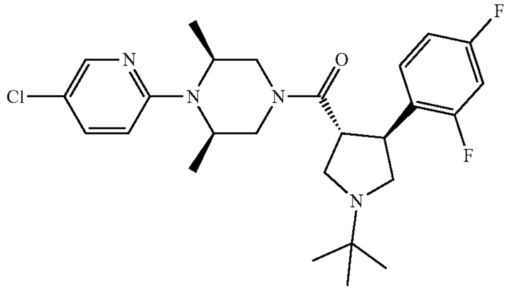
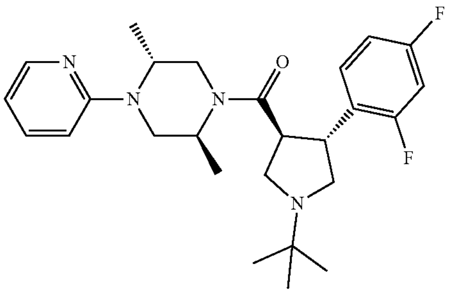
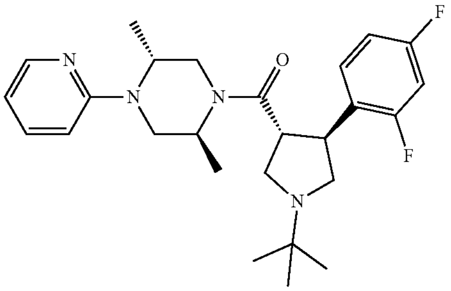
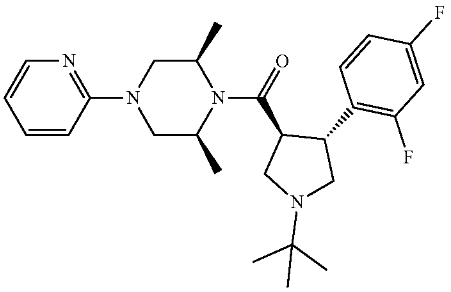
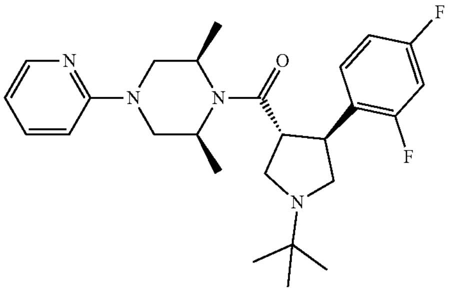

-continued
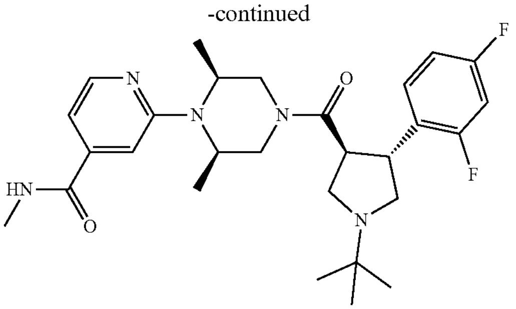
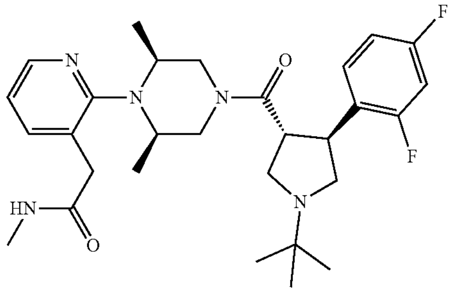
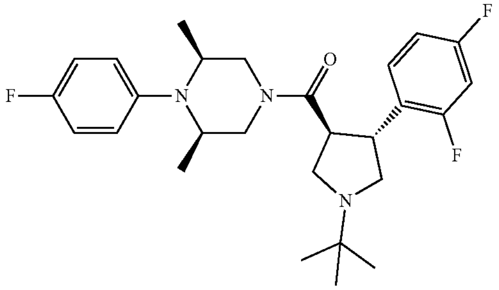
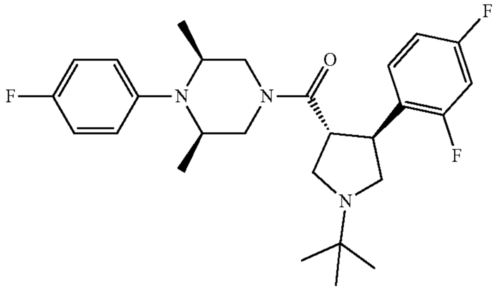
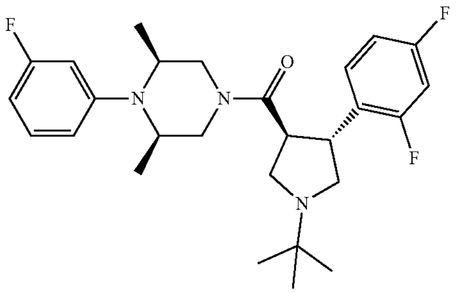
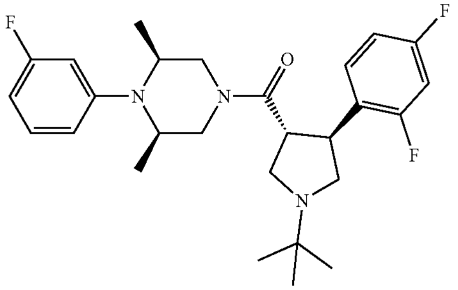
-continued
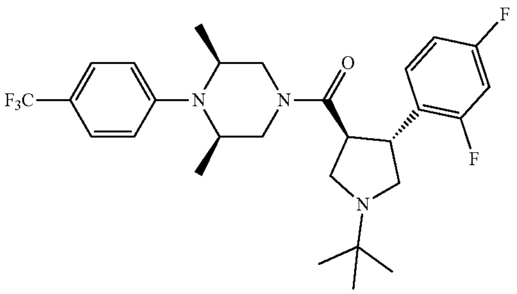
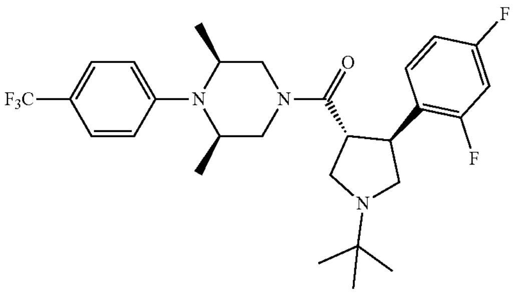
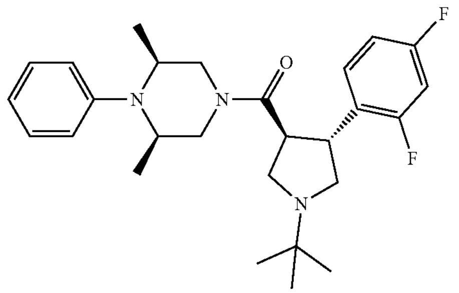
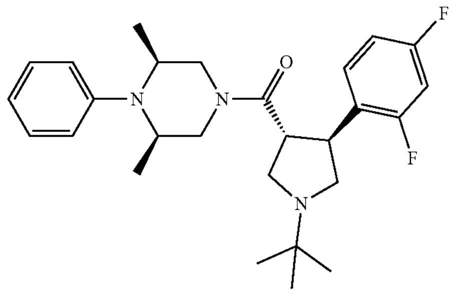
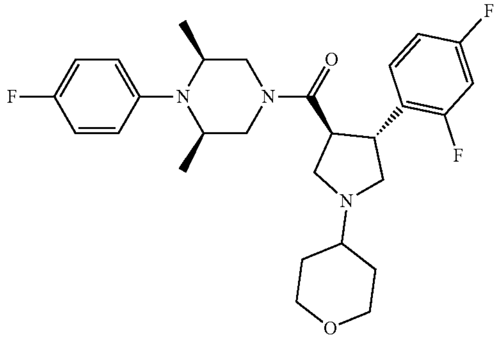

-continued
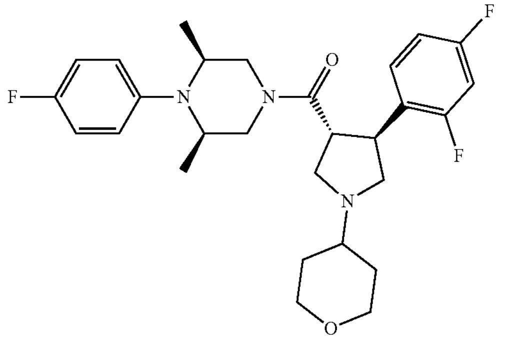
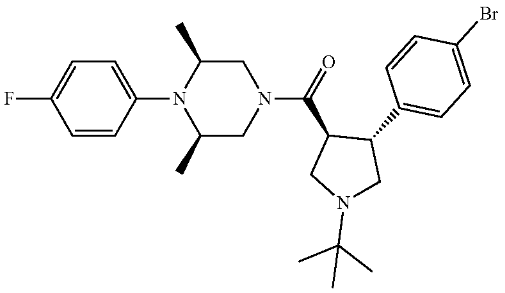
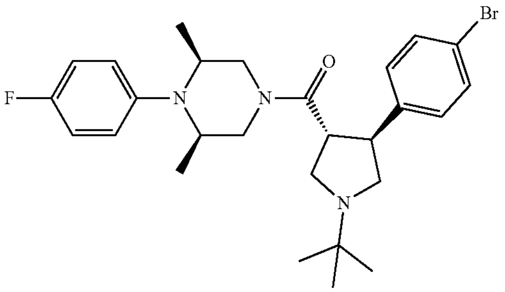
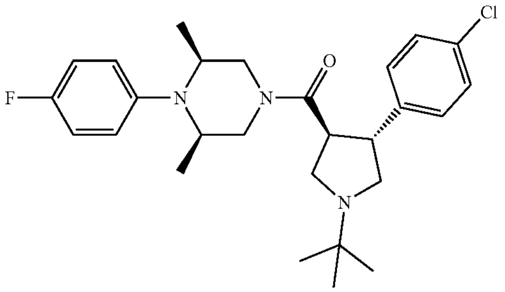
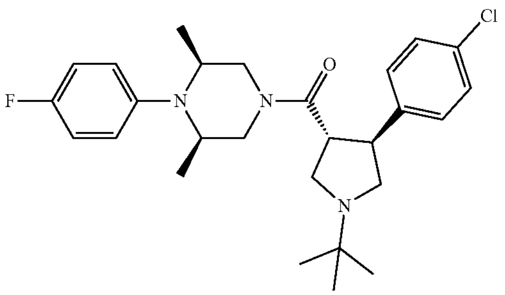
-continued
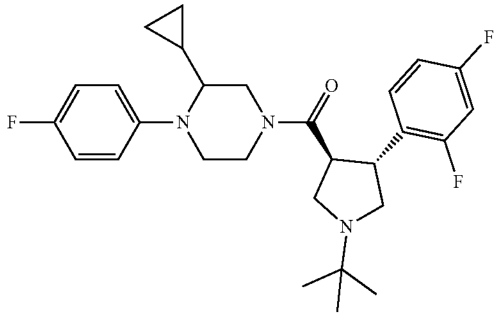
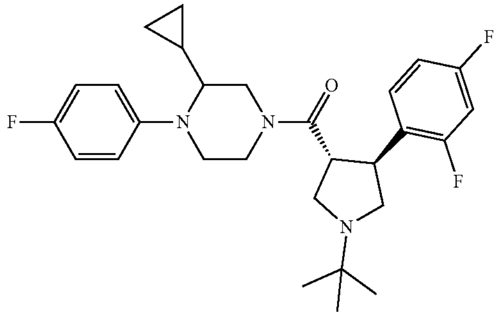
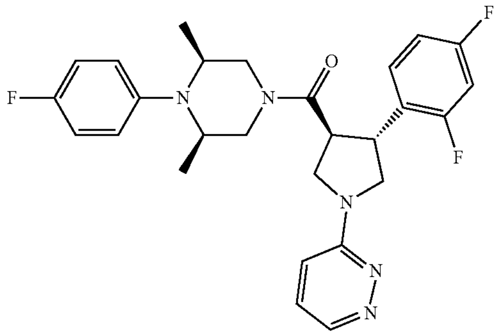
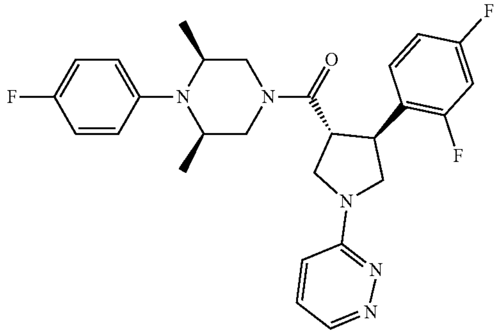
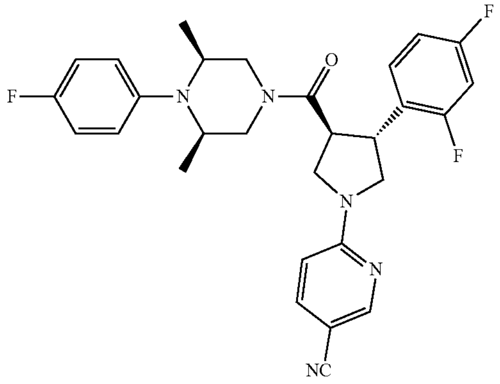

-continued
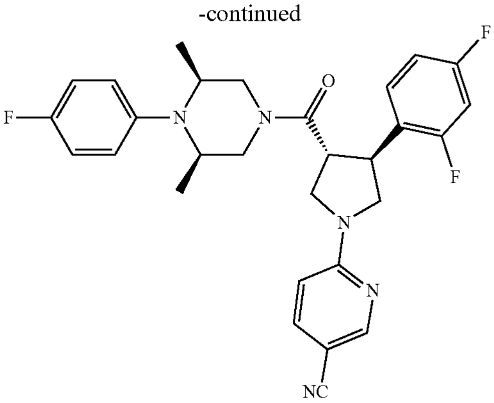
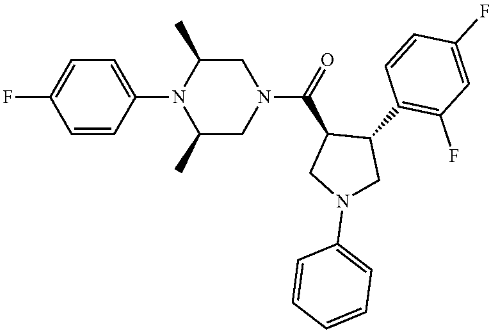
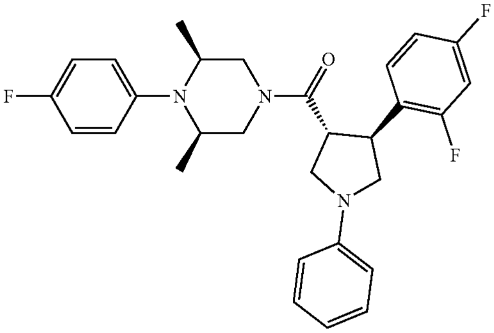
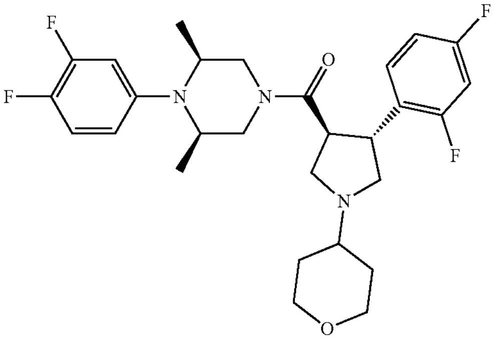
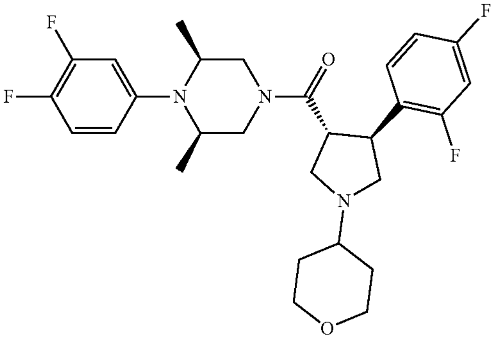
-continued
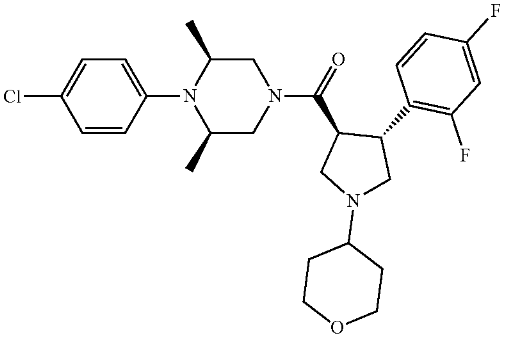
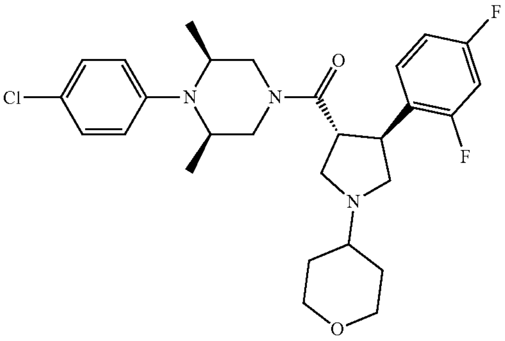
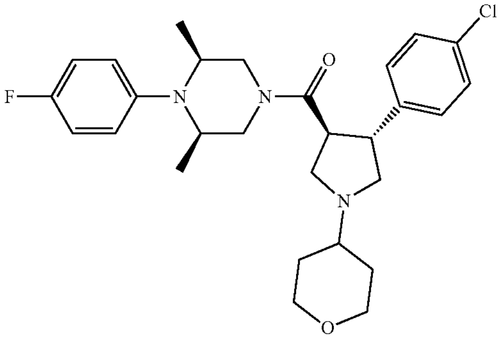
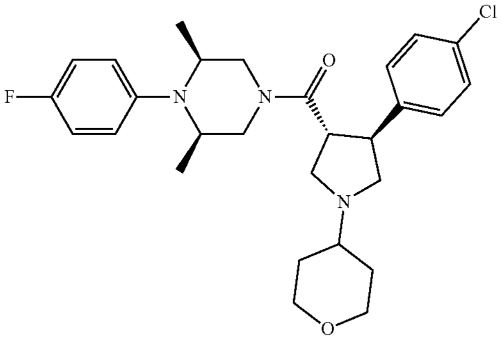
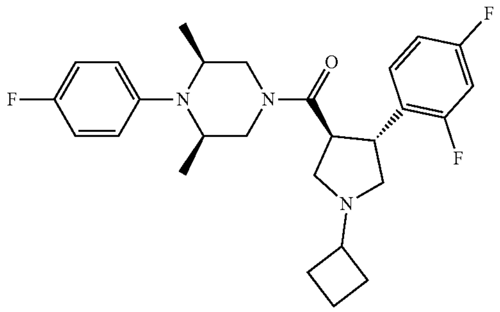

-continued
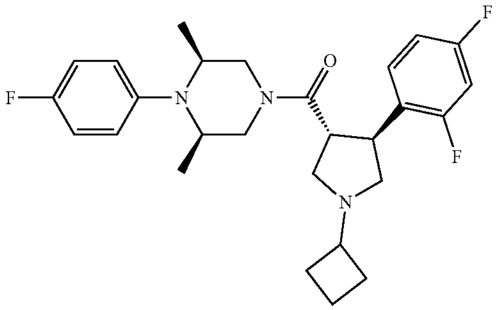
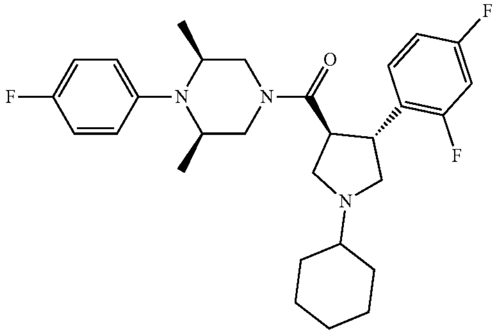
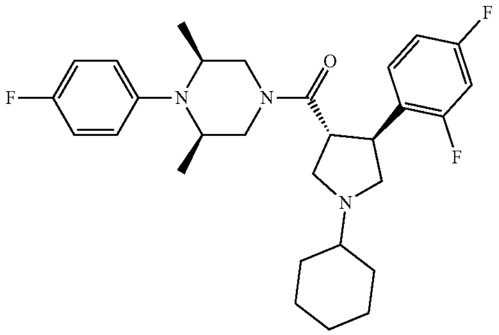
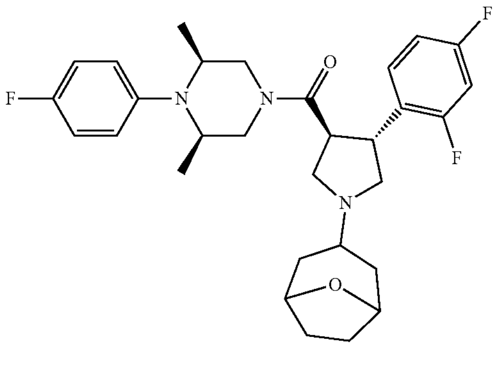
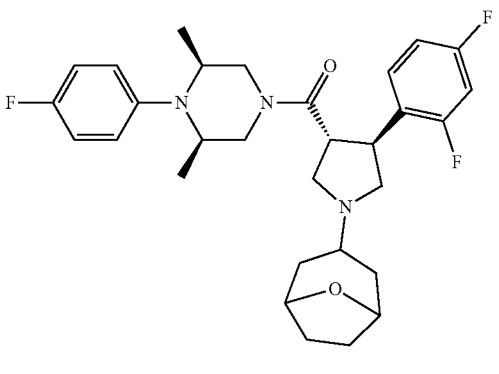
-continued
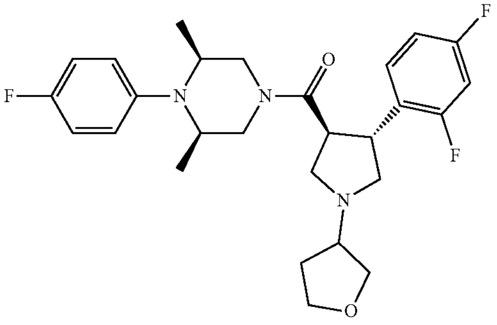
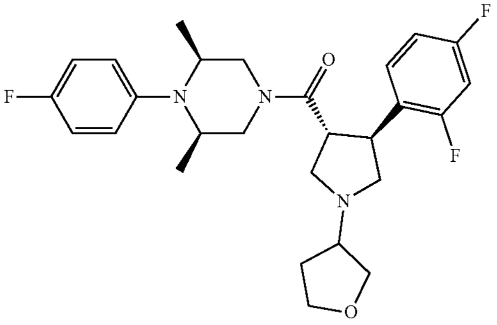
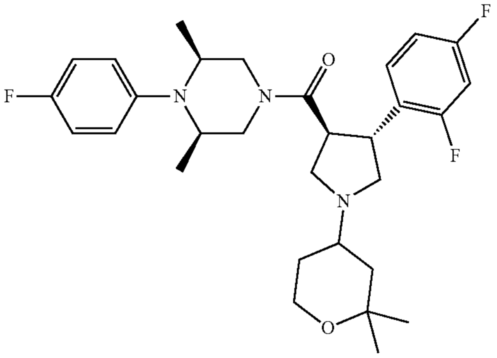
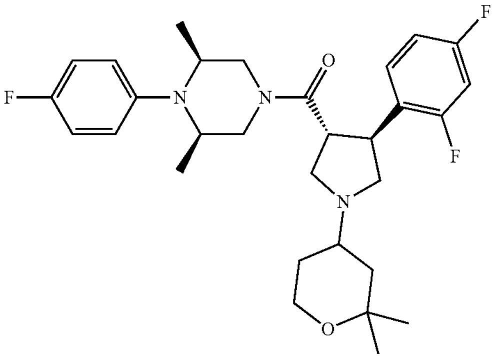
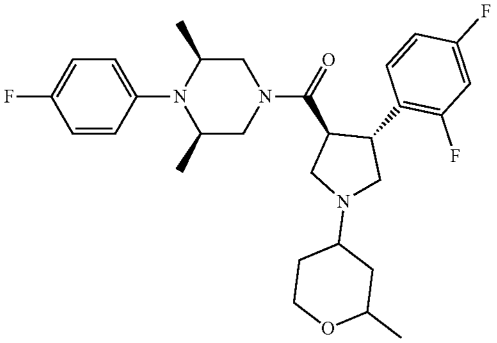

-continued
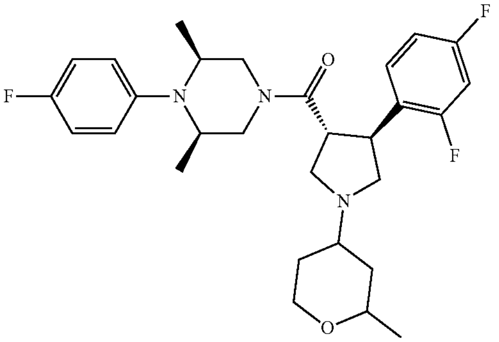
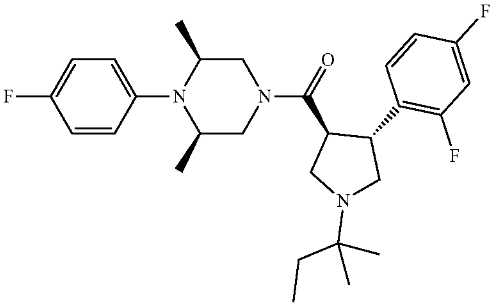
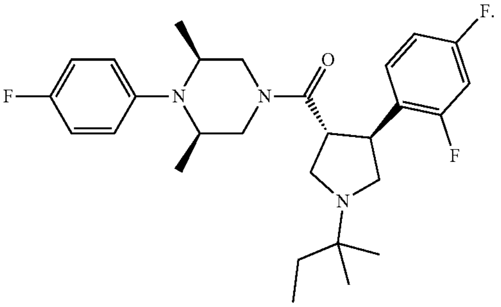 [SMILES: CCC(C)(C)N1C[C@H](C(=O)N2C[C@@H](C)N(c3ccc(F)cc3)[C@@H](C)C2)[C@@H](c2ccc(F)cc2F)C1]
The present disclosure further provides the following compounds or pharmaceutically acceptable salts thereof, which are selected from:
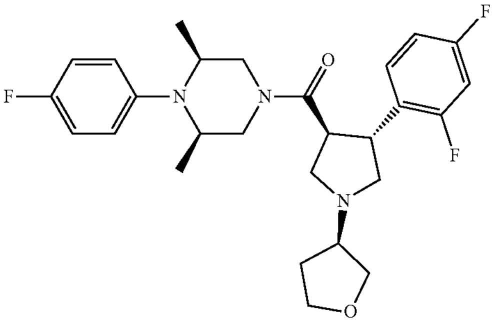
-continued
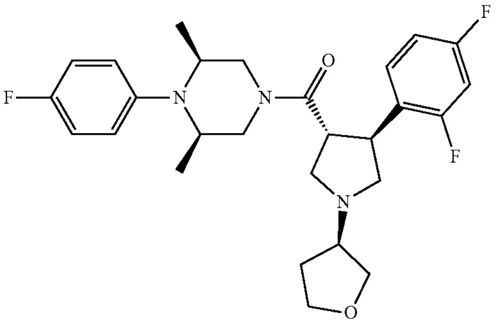
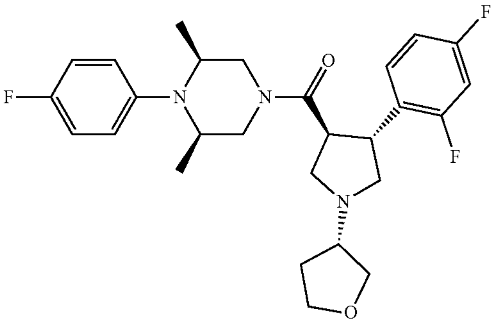
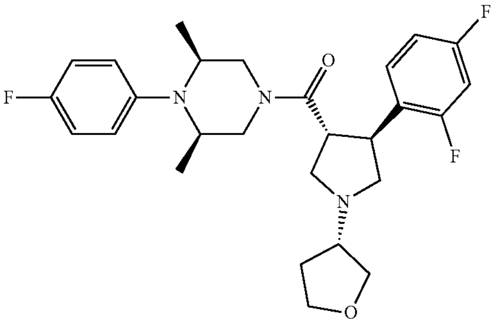
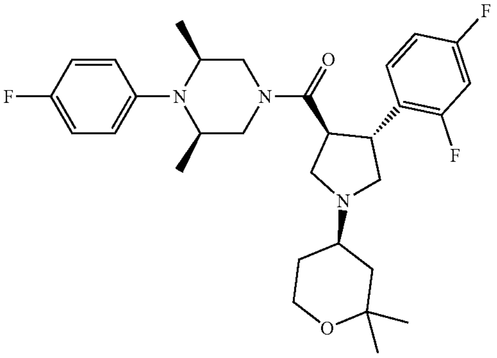
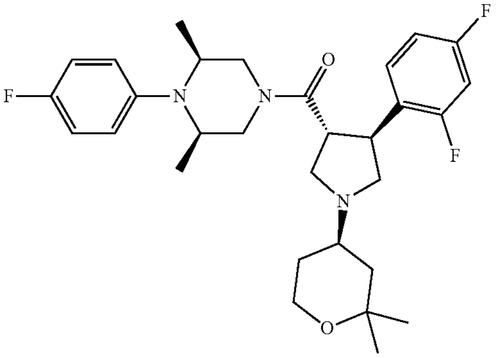

-continued
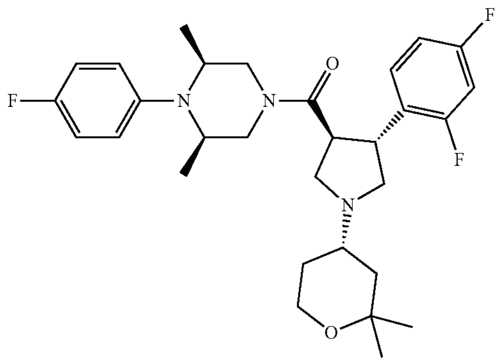
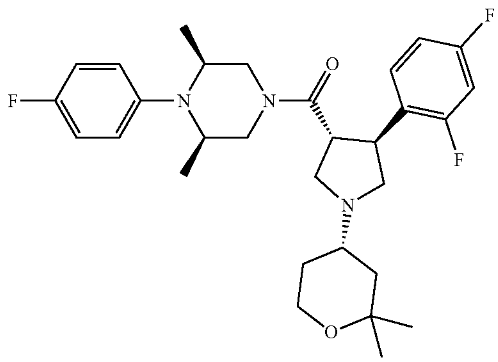
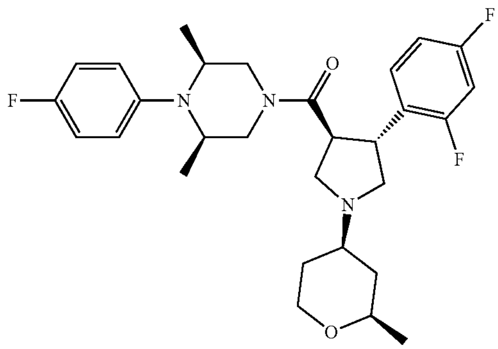
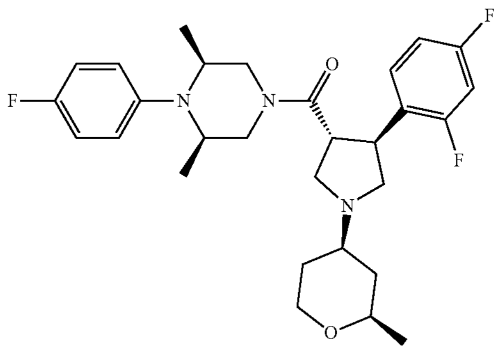
-continued
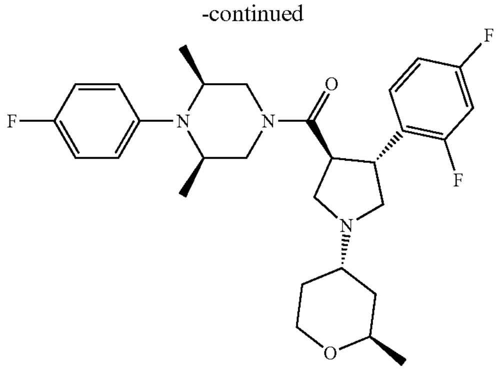
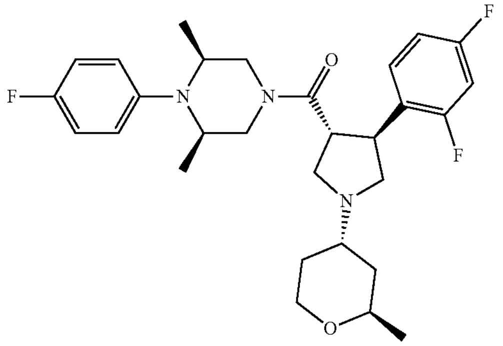
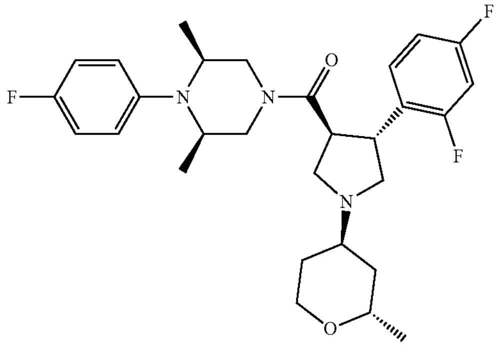
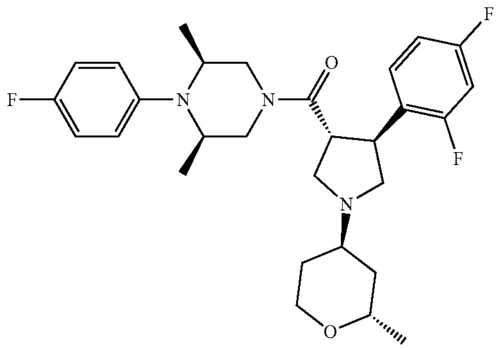
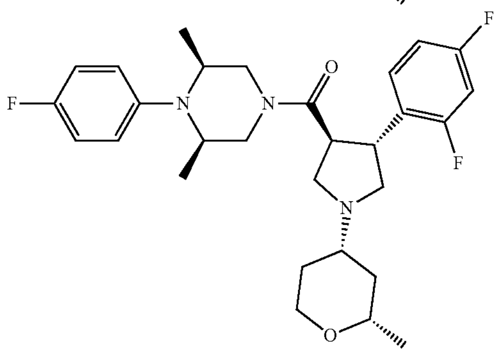

-continued

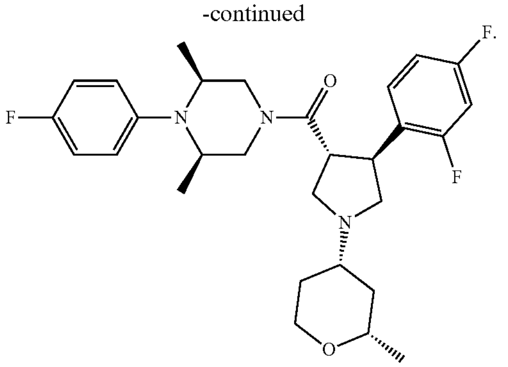

The present disclosure further provides use of the aforementioned compounds or pharmaceutically acceptable salts thereof in the preparation of a drug for treating MC4R agonist-related disease.

In some embodiments of the present disclosure, the aforementioned MC4R agonist-related disease is selected from male erectile dysfunction and female sexual desire disorder.

Technical Effects

As an MC4R receptor agonist, the compound of the present disclosure has selective agonistic effects on human MC4R receptors, and exhibits good activity in vitro experiments. The compound of the present disclosure exhibits good pharmacokinetic properties in rats, and can penetrate the blood brain barrier into brain tissue at a high brain-to-blood ratio, and reach a high drug concentration, thus it can be used for developing drugs for treating diseases related to MC4R signaling pathway such as sexual dysfunction.

Definitions and Description

Unless otherwise stated, the following terms and phrases used herein are intended to have the following meanings. A specific term or phrase should not be considered uncertain or unclear without a specific definition, but should be interpreted by ordinary meanings. A trade name herein refers to a corresponding product or active ingredient thereof.

The term "pharmaceutically acceptable" used herein refers to compounds, materials, compositions and/or dosage forms that are suitable for use in contact with human and animal tissues without excessive toxicity, irritation, allergic reactions or other problems or complications within the scope of reliable medical judgment, and are proportional to a reasonable benefit/risk ratio.

The term "pharmaceutically acceptable salt" refers to a salt of the compound of the present disclosure, prepared from the compound with specific substituents in the present disclosure and relatively non-toxic acids or bases. When the compound of the present disclosure contains relatively acidic functional groups, a base addition salt can be obtained by contacting such a compound in a neutral form with a sufficient amount of bases in a pure solution or suitable inert solvent. The pharmaceutically acceptable base addition salt includes sodium, potassium, calcium, ammonium, organic amine or magnesium salts or the like. When the compound of the present disclosure contains relatively basic functional groups, an acid addition salt can be obtained by contacting such a compound in the neutral form with a sufficient amount of acids in a pure solution or suitable inert solvent. Examples of the pharmaceutically acceptable acid addition salt includes inorganic acid salts, salts of amino acids (such as arginine), and salts of organic acids such as glucuronic acid. Some specific compounds of the present disclosure contain basic and acidic functional groups, which can be thus transformed into any base or acid addition salt.

The pharmaceutically acceptable salt of the present disclosure can be synthesized by conventional chemical methods from parent compounds containing acidic or basic groups. In general, such a salt is prepared by enabling these compounds in the form of free acids or bases to react with stoichiometric appropriate bases or acids in water, organic solvents, or a mixture of both.

As used herein and as well-known in the art, "treatment" or "treating" refers to a method used for achieving beneficial or desired results (including clinical outcomes). The beneficial or desired clinical outcomes may include, but not limited to: reducing tumor progression, reducing tumor sizes, reducing tumor growth rates, reducing tumor invasion and metastasis potential, alleviating or improving one or more symptoms or conditions, reducing disease severity, stabilizing (i.e., not worsening) disease statuses, preventing disease transmission, delaying or slowing disease progression, improving or alleviating disease statuses, and reliving (whether partially or completely), whether detectable or undetectable. "Treatment" or "treating" can also mean extending the survival period compared with the expected survival period without treatment.

The term "pharmaceutical composition" refers to a mixture of one or more compounds or salts of the present disclosure with pharmaceutically acceptable excipients. The purpose of the pharmaceutical composition is to facilitate the administration of the compound of the present disclosure to an organism.

The therapeutic dose of the compound of the present disclosure may be determined according to, for example, the following: specific purposes of treatment, methods of administering the compound, the health and condition of patient, and the judgment of prescribing physician. The proportion or concentration of the compound of the present disclosure may not be fixed in a medicinal composition, but depending on multiple factors, including doses, chemical properties (such as hydrophobicity) and routes of administration.

The term "treatment" means administering the compound or preparation of the present disclosure to improve or eliminate a disease or one or more symptoms related to the disease, and includes:

(i) suppressing the disease or disease condition, i.e., arresting progression thereof; and (ii) alleviating the disease or disease condition, i.e., making the disease or disease condition subside.

The term "therapeutically effective amount" refers to the amount of the compound of the present disclosure to (i) treat a specific disease, condition, or disorder, (ii) alleviate, improve, or eliminate one or more symptoms of the specific disease, condition, or disorder, or (iii) prevent or delay the onset of one or more symptoms of the specific disease, condition, or disorder as described herein. The amount of the compound of the present disclosure that constitutes the "therapeutically effective amount" varies depending on the compound, disease statuses and severity, administration methods, and the age of a mammal to be treated, but may be routinely determined by those skilled in the art based on their own knowledge and the content of the present disclosure.

Unless otherwise required in the present disclosure, in the entire specification and subsequent claims, the words "comprise" and their English variants, for example, "comprises" and "comprising" shall be interpreted as open and inclusive meanings, i.e., "including but not limited to".

The term "one embodiment" or "embodiment" or "in another embodiment" or "in some embodiments" mentioned throughout the specification means that at least one embodiment includes specific reference elements, structures or characteristics related to the embodiment. Therefore, phrases "in one embodiment" or "in the embodiment" or "in another embodiment" or "in some embodiments" appearing in different positions throughout the specification do not necessarily all refer to a same embodiment. In addition, specific elements, structures or characteristics may be combined in one or more embodiments in any appropriate manner.

Unless otherwise stated, the term "isomer" intends to include geometric isomers, cis and trans-isomers, stereoisomers, enantiomers, optical isomers, non-enantiomers and tautomers.

The compound of the present disclosure may exist in specific geometric or stereoisomeric forms. The present disclosure contemplates that all such compounds, including cis- and trans-isomers, (−)- and (+)-enantiomers, (R)- and (S)-enantiomers, non-enantiomers, (D)-isomers, (Z)-isomers, and racemic mixtures and other mixtures thereof, for example, enantiomers or non-enantiomer enriched mixtures, fall within the scope of the present disclosure. Substituents such as alkyl may have additional asymmetric carbon atoms. All the isomers and mixtures thereof are included within the scope of the present disclosure.

Unless otherwise stated, the term "enantiomer" or "optical isomer" refers to stereoisomers in a mutual mirror-image relationship.

Unless otherwise stated, the term "cis and trans-isomer" or "geometric isomer" is caused by the fact that double bonds or single bonds of ringed carbon atoms cannot rotate freely.

Unless otherwise stated, the term "diastereoisomer" refers to C:\Users\astiteler\AppData\Roaming\iManage\Work\Recent\2234-23 PCT_US PIPERAZINE DERIVATIVES AND APPLICATION THEREOF\quot:http:\baike.baidu.com\item\分子\479055&quot a stereoisomer where a molecule has two or more chiral centers and has a non mirror like relationship between molecules.

Unless otherwise stated, "(+)" represents dextro, "(−)" represents levo, and "(±)" represents racemic.

Unless otherwise stated, an absolute configuration of a stereocenter is represented by a solid wedge bond ( ) and a dashed wedge bond ( ), a relative configuration of the stereocenter is represented by a solid straight bond ( ) and a dashed straight bond ( ), the solid wedge bond ( ) or the dashed wedge bond ( ) is represented by a wavy line ( ), or the solid straight bond ( ) and the dashed straight bond ( ) are represented by a wavy line ( ).

Unless otherwise stated, the solid straight bond ( ) and the dashed straight bond ( ) on two adjacent chiral atoms represent relative configurations, for example,

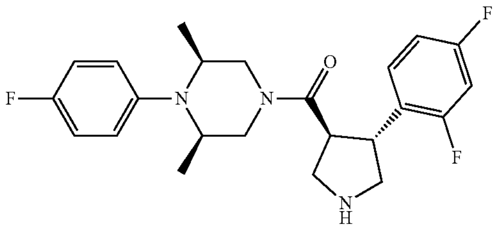 [SMILES: C[C@@H]1CN(C(=O)[C@@H]2CNC[C@H]2c2ccc(F)cc2F)C[C@H](C)N1c1ccc(F)cc1]

indicates that groups linked to two chiral carbons of tetrahydropyrrole are in a trans position, i.e.,

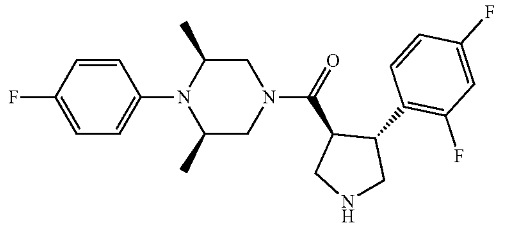

or

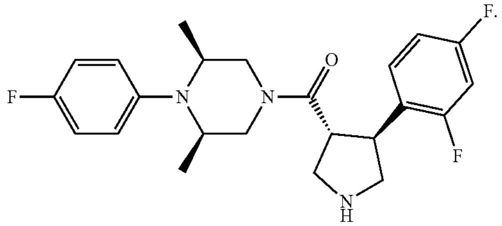

The compound of the present disclosure may exist in a specific form. Unless otherwise stated, the term "tautomer" or "tautomeric form" means that at room temperature, isomers of different functional groups are in dynamic equilibrium and can be quickly mutually transformed. If a tautomer is possible (for example, in a solution), the chemical equilibrium of the tautomer can be achieved. For example, a proton tautomer (also known as prototropic tautomer) includes mutual transformation through proton migration, such as ketone-enol isomerization and imine-enamine isomerization. A valence tautomer includes mutual transformation through recombination of some bonding electrons. A specific example of ketone-enol tautomerism is the mutual transformation of two tautomers of pentane-2,4-dione and 4-hydroxypentane-3-en-2-one.

Unless otherwise stated, the terms "enrich in one isomer", "enriched isomer", "enrich in one enantiomer" or "enriched enantiomer" mean that the content of one isomer or enantiomer is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "excessive isomer" or "excessive enantiomer" refers to the difference between the relative percentages of two isomers or two enantiomers. For example, if the content of one isomer or enantiomer is 90%, and the content of the other isomer or enantiomer is 10%, the excess (ee value) of the isomer or enantiomer is 80%.

Optically active (R)- and(S)-isomers as well as D and L isomers can be prepared through chiral synthesis, chiral reagents, or other conventional techniques. If an enantiomer of a compound of the present disclosure is desired, the enantiomer can be prepared through asymmetric synthesis or derivatization with chiral additives, in which a resulting non-enantiomeric mixture is separated, and auxiliary groups are split with assistance to provide a pure desired enantiomer. Alternatively, when molecules contain basic functional groups (for example, amino) or acidic functional groups (for example, carboxyl), non-enantiomeric salts are formed with appropriate optically active acids or bases, and then non-enantiomeric resolution is conducted using conventional methods known in the art, followed by recovery to obtain pure enantiomers. In addition, enantiomers and non-enantiomers are generally separated through chromatography, and the chromatography adopts chiral stationary phases, and is optionally combined with chemical derivatization methods (for example, generating aminoformates from amines).

The compound of the present disclosure can contain atomic isotopes of a non-natural proportion on one or more atoms constituting the compound. For example, the compound can be labeled with radioactive isotopes, such as tritium ($^3H$), iodine-125 ($^{125}I$), or C-14 ($^{14}C$). Further, for example, deuterated drugs can be formed by substituting hydrogen with deuterium. The bond between deuterium and carbon is stronger than that between ordinary hydrogen and carbon. Compared to undeuterated drugs, deuterated drugs have the advantages of reducing toxic side effects, increasing drug stability, enhancing therapeutic efficacy, extending the biological half-life of drugs, and the like. The transformation of all isotopic compositions of the compound of the present disclosure, whether radioactive or not, is included within the scope of the present disclosure.

"Optional" or "optionally" means that events or situations described subsequently may but not necessarily appear, and the description includes the circumstances in which the events or situations occur and the circumstances in which the events or situations do not occur.

The term "substituted" means that any one or more hydrogen atoms on a specific atom are substituted by a substituent, the substituent can include variants of deuterium and hydrogen, as long as the valence state of the specific atom is normal and the substituted compound is stable. When the substituent is oxygen (i.e., =O), it means that two hydrogen atoms are substituted. Oxygen substitution does not occur on aromatic groups. The term "optionally substituted" refers to either substituted or not substituted, and unless otherwise specified, the type and number of substituents can be arbitrary on a chemically achievable basis.

When any variable (for example, R) appears more than once in the composition or structure of a compound, the definition thereof in each case is independent. Therefore, for example, if a group is substituted by 0-2 R(s), the group can be optionally substituted by at most two Rs, and in each case, R has independent options. In addition, combinations of substituents and/or variants thereof are allowed only if such combinations produce stable compounds.

When the number of a linking group is 0, for example, $-(CRR)_0-$, it indicates that the linking group is a single bond.

When one of variables is selected from a single bond, it indicates that two groups linked thereby are directly linked, for example, when L in A-L-Z represents a single bond, it indicates that the structure is actually A-Z.

When the connection direction of listed linking groups is not indicated, the linking direction is arbitrary. For example, if the linking group L in

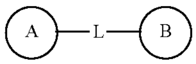

is -M-W—, at this time, -M-W— can link ring A and ring B in the same direction as the reading order from left to right to form

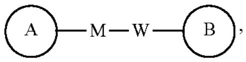, or link ring A and ring B in the opposite direction as the reading order from left to right to form

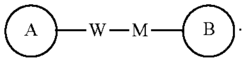.

The combination of linking groups, substituents, and/or variants thereof is allowed only if such a combination produces stable compounds.

Unless otherwise specified, when a group has one or more linkable sites, any one or more sites of the group can be linked to other groups through chemical bonds. When the linking method of the chemical bond is not localized, and H atoms exist at the linkable site, the number of H atoms at the site correspondingly decreases with the number of linked chemical bonds to be groups of corresponding valences when linking the chemical bonds. The chemical bonds linking said site to other functional groups can be represented by a solid straight bond (), a dashed straight bond (), or a wavy line () For example, the solid straight bond in-$OCH_3$ indicates linkage to other groups through the oxygen atom in the group; the dashed straight bond in

indicates linkage to other groups through both ends of the nitrogen atom in the group; the wavy line in

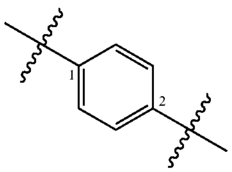 [SMILES: *c1ccc(*)cc1]

indicates linkage to other groups through carbon atoms at sites 1 and 2 of phenyl;

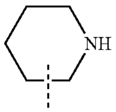

indicates that any linkable site on the piperidinyl can be linked to other groups through one chemical bond, including at least four connection modes

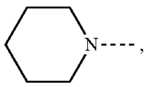, 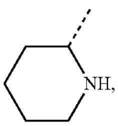, 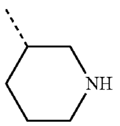 and

-continued

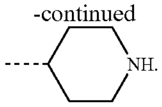

Even if an H atom is drawn on-N—,

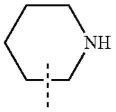

still includes a group with

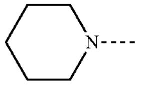

linking mode, only when one chemical bond is linked, the H at this site will correspondingly decrease by one to become monovalent piperidine group.

Unless otherwise specified, $C_{n-n+m}$ or $C_n$-$C_{n+m}$ includes any specific case of n to (n+m) carbons, for example, $C_{1-12}$ include $C_1$, $C_2$, $C_3$, $C_4$, $C_5$, $C_6$, $C_7$, $C_8$, $C_9$, $C_{10}$, $C_{11}$, and $C_{12}$, also include any range from n to nim, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n to (n+m) members means that the number of atoms on the ring is n to (n+m), for example, 3-12 membered rings include 3-membered rings, 4-membered rings, 5-membered rings, 6-membered rings, 7-membered rings, 8-membered rings, 9-membered rings, 10-membered rings, 11-membered rings, and 12-membered rings, also include any range from n to (n+m), for example, 3-12 membered rings include 3-6 membered rings, 3-9 membered rings, 5-6 membered rings, 5-7 membered rings, 6-7 membered rings, 6-8 membered rings, and 6-10 membered rings, etc.

Unless otherwise specified, the term "$C_{1-4}$ alkyl" is used to represent a straight or branched chain saturated hydrocarbon group consisting of 1 to 4 carbon atoms. The $C_{1-4}$ alkyl includes $C_{1-2}$, $C_{1-3}$ and $C_{2-3}$ alkyl, etc.; it can be monovalent (for example, methyl), divalent (for example, methylene) or multivalent (for example, methine). Examples of $C_{1-4}$ alkyl include, but are not limited to, methyl (Me), ethyl (Et), propyl (including n-propyl and isopropyl), butyl (including n-butyl, isobutyl, s-butyl and t-butyl), etc.

Unless otherwise specified, the term "$C_{1-3}$ alky" is used to represent a straight or branched chain saturated hydrocarbon group consisting of 1 to 3 carbon atoms. The $C_{1-3}$ alkyl includes $C_{1-2}$ and $C_{2-3}$ alkyl, etc.; it can be monovalent (for example, methyl), divalent (for example, methylene) or multivalent (for example, methine). Examples of $C_{1-3}$ alkyl include, but are not limited to, methyl (Me), ethyl (Et), propyl (including n-propyl and isopropyl), etc.

Unless otherwise specified, the term "$C_{1-3}$ alkoxyl" represents those alkyl groups containing 1 to 3 carbon atoms that are bonded to the rest of the molecule via an oxygen atom. The $C_{1-3}$ alkoxyl includes $C_{1-2}$, $C_{2-3}$, $C_3$ and $C_2$ alkoxyl, etc. Examples of $C_{1-3}$ alkoxyl include, but are not limited to, methoxy, ethoxy, propoxy (including n-propoxy and isopropoxy), etc.

Unless otherwise specified, "$C_{3-6}$ cycloalkyl" means a saturated cyclic hydrocarbon group consisting of 3 to 6 carbon atoms, which is a monocyclic or bicyclic system. The $C_{3-6}$ cycloalkyl includes $C_{3-5}$, $C_{4-5}$ and $C_{5-6}$ cycloalkyl, etc.; it can be monovalent, divalent or multivalent. Examples of $C_{3-6}$ cycloalkyl include, but are not limited to, cyclopropyl, cyclobutyl, cyclopentyl, cyclohexyl, etc.

Unless otherwise specified, the term "4-8 membered heterocycloalkyl" alone or in combination with other terms means a saturated cyclic group consisting of 4 to 8 ring atoms, 1, 2, 3 or 4 ring atom of which are independently selected from heteroatoms of O, S, and N, the rest being carbon atoms, wherein the nitrogen atoms are optionally quaternized, and the nitrogen and sulfur heteroatoms may be optionally oxidized (i.e., NO and $S(O)_p$, p is 1 or 2). It includes monocyclic and bicyclic systems, wherein the bicyclic system includes spiro rings, parallel rings and bridged rings. Furthermore, in the case of the "4-8 membered heterocycloalkyl", heteroatoms may occupy the sites of the heterocycloalkyl connected to the rest of the molecule. The 4-8 membered heterocycloalkyl includes 4-6 membered, 5-6 membered, 4 membered, 5 membered and 6 membered heterocycloalkyl, etc. Examples of 4-8 membered heterocycloalkyl include but are not limited to azetidinyl, oxetanyl, thietidinyl, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, omopiperazinyl, homopiperidinyl or dioxepanyl, etc.

Unless otherwise specified, the term "5-6 membered heterocycloalkyl" alone or in combination with other terms means a saturated cyclic group consisting of 5 to 6 ring atoms, 1, 2, 3 or 4 ring atom of which are independently selected from heteroatoms of O, S, and N, the rest being carbon atoms, wherein the nitrogen atoms are optionally quaternized, and the nitrogen and sulfur heteroatoms may be optionally oxidized (i.e., NO and $S(O)_p$, p is 1 or 2). It includes monocyclic and bicyclic systems, wherein the bicyclic system includes spiro rings, parallel rings and bridged rings. Furthermore, in the case of the "5-6 membered heterocycloalkyl", heteroatoms may occupy the sites of the heterocycloalkyl connected to the rest of the molecule. The 5-6 membered heterocycloalkyl includes 5-membered and 6-membered heterocycloalkyl. Examples of 5-6 membered heterocycloalkyl include but are not limited to pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, etc.

Unless otherwise specified, the terms "5-6 membered heteroaromatic ring" and "5-6 membered heteroaryl" can be used interchangeably in the present disclosure. The term "5-6 membered heteroaryl" means a monocyclic group consisting of 5 to 6 ring atoms with a conjugated π electron system, 1, 2, 3 or 4 ring atoms of which are heteroatoms independently selected from O, S and N, and the rest are carbon atoms. The nitrogen atoms are optionally quaternized, and the nitrogen and sulfur heteroatoms are optionally oxidized (i.e., NO and $S(O)_p$, p is 1 or 2). 5-6 membered heteroaryl can be connected to the rest of the molecule through heteroatoms or carbon atoms. The 5-6 membered heteroaryl includes 5-membered heteroaryl and 6-membered heteroaryl. Examples of the 5-6 membered heteroaryl include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2, 4-triazolyl, etc.), tetrazolyl, isoxazolyl (3-isoxazolyl, 4-isoxazolyl, 5-isoxazolyl, etc.), thiazolyl (including 2-thiazolyl, 4-thiazolyl and 5-thiazolyl, etc.), furyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl, 4-pyrimidinyl, etc.).

Unless otherwise specified, the term “halogenated” or “halogen” alone or as part of another substituent means a fluorine, chlorine, bromine or iodine atom.

The compounds of the present disclosure can be prepared by a variety of synthetic methods well known to those skilled in the art, including the specific embodiments listed below, embodiments formed by combining them with other chemical synthesis methods, and equivalent alternatives well known to those skilled in the art. Preferred embodiments include, but are not limited to, the examples of the present disclosure.

The structural characterization of the compound of the present disclosure can be performed by conventional methods well known to those skilled in the art. If the present disclosure involves an absolute configuration of a compound, the absolute configuration can be characterized by conventional technical means in the art. For example, by single crystal X-ray diffraction (SXRD) method, the cultured single crystal is used to collect diffraction intensity data using a Bruker D8 venture diffractometer, the light source is CuKα radiation, and the scanning mode is p/@ scanning. After collecting relevant data, the direct method (Shelxs97) is further used to parse the crystal structure, thus the absolute configuration can be characterized.

The solvent used in the present disclosure is commercially available.

Compounds are named according to conventional naming principles in the art or using ChemDraw® software, and commercially available compounds adopt the names in the supplier catalog.

Following abbreviations are used in the present disclosure: EDTA represents ethylenediaminetetraacetic acid; cAMP represents cyclic adenosine monophosphate; TMS represents trimethylsilyl; DCM represents dichloromethane; THF represents tetrahydrofuran; TFA represents trifluoroacetic acid; TEA represents triethylamine; NaBH(OAc) 3 represents sodium borohydride acetate; Me represents methyl.

DETAILED DESCRIPTION

The present disclosure will be described in detail hereafter in conjunction with examples which do not constitute any adverse limitations to the present disclosure. The present disclosure has been described in detail herein, and specific embodiments thereof are also disclosed. For those skilled in the art, it will be apparent to make various changes and improvements to the embodiments of present disclosure without departing from the spirit and scope of the present disclosure.

Reference Example 1

Intermediate 1

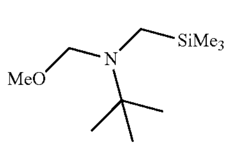

Synthetic Route:

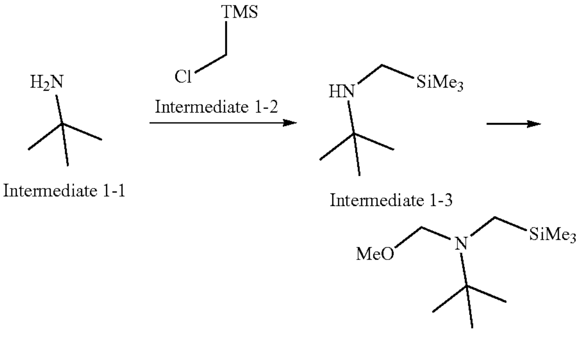

Intermediate 1-1 Intermediate 1-3 Intermediate 1

Step 1: Synthesis of Intermediate 1-3

Tert-butylamine (33.41 g, 456.79 mmol, 2.24 eq) and intermediate 1-2 (25 g, 203.8 mmol, 1 eq) in DMSO (200 mL) solution was added into a dry flask, stirred at 90° C. for 12 hours. The reaction ended when the reaction solution became turbid and no condensate dripped. The reaction solution was allowed to stand for liquid separation, and the upper layer was washed with water (100 mL). The organic phase after liquid separation was dried over anhydrous sodium sulfate, filtered, and concentrated under reduced pressure to obtain intermediate 1-3. $^1H$ NMR (400 MHz, $CD_3OD$) δ: 1.97 (s, 2H), 1.09 (s, 9H), 0.07 (s, 9H).

Step 2: Synthesis of Intermediate 1

37% formaldehyde aqueous solution (16.52 g, 203.52 mmol, 1.41 eq) and the intermediate 1-3 (23 g, 114.34 mmol, 1 eq) were added into a dry flask, potassium carbonate (11.97 g, 86.61 mmol, 0.6 eq) and methanol (13.87 g, 433.03 mmol, 3 eq) were added at 0° C., then slowly heated to room temperature and stirred continually for 1 hour, and then the aqueous phase was removed, the residue was added with potassium carbonate (5.98 g, 43.3 mmol, 0.3 eq) for reaction at 20° C. under stirring for 12 hours. The reaction solution was filtered, and the filtrate was added with 50 mL of water, stirred for 0.5 hours, and then allowed to stand for liquid separation. The organic phase was dried and then concentrated under reduced pressure to obtain intermediate 1. $^1H$ NMR (400 MHz, $CD_3OD$) δ: 4.18 (s, 2H), 3.35 (s, 3H), 2.28 (s, 2H), 1.12 (s, 9H), 0.05 (s, 9H).

Reference Example 2

Intermediate 2

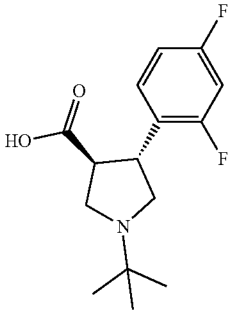

or

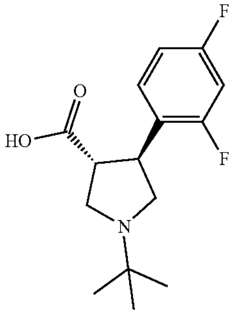

Synthetic Route:

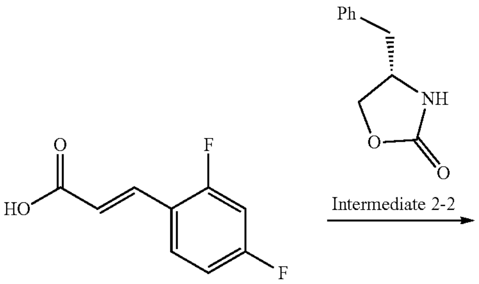

Intermediate 2-1

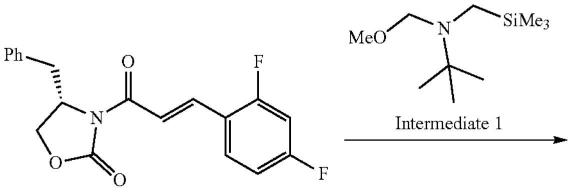

Intermediate 2-3

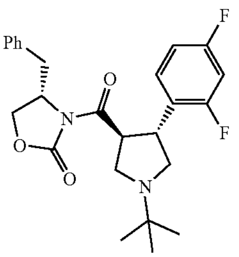

or

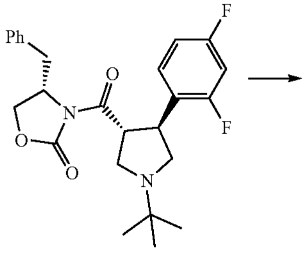

Intermediate 2-4

-continued

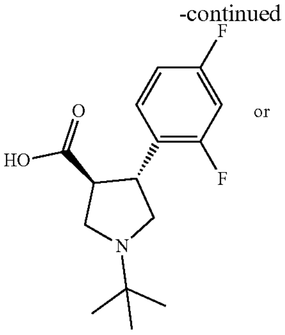

or

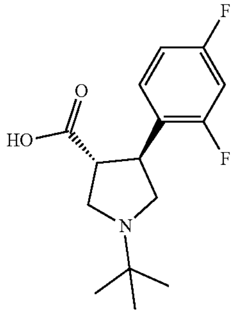

Intermediate 2

Step 1: Synthesis of Intermediate 2-3

A solution of intermediate 2-1 (50 g, 271.53 mmol, 1 eq) in dichloromethane (500 mL) was added into a dry flask, oxalyl chloride (75.82 g, 597.37 mmol, 52.29 mL, 2.2 eq) and DMF (0.99 g, 13.58 mmol, 1.04 mL, 0.05 eq) were added at 0° C. Reaction was conducted at 15° C. under stirring for 1 hour. The reaction solution was concentrated under reduced pressure, then added with dichloromethane (600 mL) for dissolution, lithium chloride (57.55 g, 1.36 mol, 5 eq) and triethylamine (137.36 g, 1.36 mol, 188.94 mL, 5 eq) were added at 0° C., and finally added with a solution of intermediate 2-2 (48.11 g, 271.49 mmol, 1 eq) in dichloromethane. The reaction was conducted at 20° C. with stirring for 12 hours. The reaction solution was adjusted to a pH of about 7 with a 5%-10% citric acid aqueous solution, allowed to stand for liquid separation, then the aqueous phase was extracted with dichloromethane (200 mL×2). The organic phase was dried over anhydrous sodium sulfate and concentrated under reduced pressure. The residue was added with methyl tert-butyl ether (100 mL) and homogenized for 1 hour, and then filtered to obtain intermediate 2-3. $^{1}H$ NMR (400 MHz, $CDCl_3$) δ: 8.08-7.95 (m, 2H), 7.76-7.70 (m, 1H), 7.41-7.28 (m, 5H), 7.00-6.89 (m, 2H), 4.88-4.82 (m, 1H), 4.33-4.25 (m, 2H), 3.44-3.30 (m, 1H), 2.92-2.87 (m, 1H).

Step 2: Synthesis of Intermediate 2-4

The intermediate 2-3 (40 g, 116.51 mmol, 1 eq) and the intermediate 1 (47.39 g, 139.81 mmol, 1.2 eq) were dissolved in dichloromethane (400 mL), added dropwise with trifluoroacetic acid (13.28 g, 116.51 mmol, 8.63 mL, 1 eq) slowly under stirring. Reaction was conducted at 15° C. under stirring for 1 hour. After the compilation of reaction, 200 mL of saturated sodium bicarbonate solution was added, and allowed to stand for liquid separation, and then the aqueous phase was extracted with dichloromethane (200 mL×2). The organic phase was dried over anhydrous sodium sulfate and concentrated under reduced pressure. The residue was added with methyl tert-butyl ether (100 mL) and homogenized to obtain intermediate 2-4. $^{1}H$ NMR (400 MHz, $CDCl_3$) δ=7.49-7.43 (m, 1H), 7.29-7.23 (m, 3H), 7.11-7.09 (m, 2H), 6.89-6.85 (m, 1H), 6.82-6.79 (m, 1H), 4.73-4.67 (m, 1H), 4.34-4.28 (m, 1H), 4.23-4.12 (m, 3H), 3.39-3.35 (m, 1H), 3.24-3.20 (m, 2H), 2.87-2.81 (m, 2H), 2.76-2.71 (m, 1H), 1.12 (s, 9H).

Step 3: Synthesis of Intermediate 2

The intermediate 2-4 (23 g, 51.98 mmol, 1 eq) was dissolved in tetrahydrofuran (160 mL), and then added with lithium hydroxide monohydrate (5.45 g, 129.94 mmol, 2.5 eq) and water (80 mL). The reaction was conducted at 15° C. under stirring for 12 hours. The reaction solution was directly concentrated under reduced pressure, and then extracted with water (50 mL) and ethyl acetate (30 mL×3).

The aqueous phase was adjusted to pH~2 with 2 N hydrochloric acid and then directly concentrated under reduced pressure. The residue was dissolved with dichloromethane (50 mL) and filtered, and the organic phase was concentrated under reduced pressure to obtain intermediate 2. $^1$H NMR (400 MHz, DMSO) δ=12.48 (s, 1H), 7.82 (s, 1H), 7.28-7.23 (m, 1H), 7.16-7.12 (m, 1H), 3.98-3.64 (m, 3H), 3.50-3.40 (m, 2H), 3.23-3.17 (m, 1H), 1.36 (s, 9H).

Reference Example 3

Intermediate 3

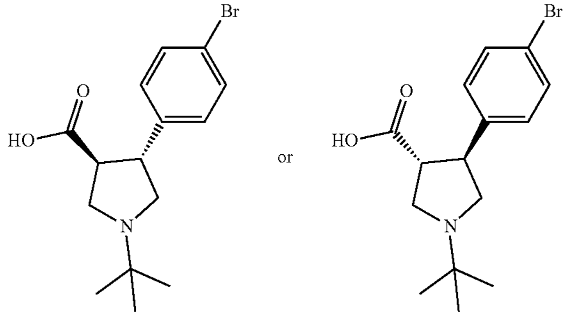
or

Synthetic Route:

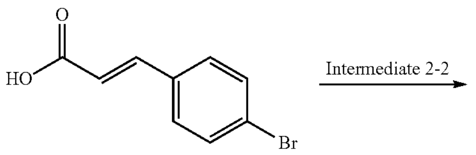

Intermediate 3-1

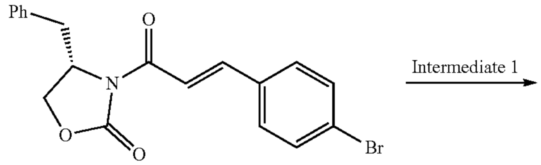

Intermediate 3-2

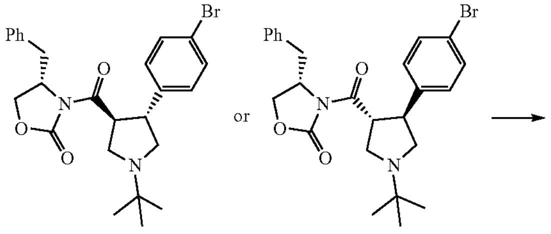
or
Intermediate 3-3

-continued

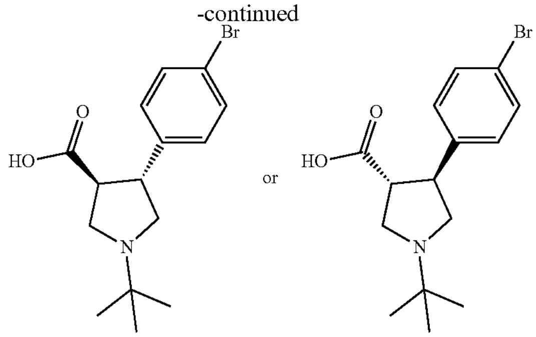
or
Intermediate 3

Step 1: Synthesis of Intermediate 3-2

Compound 3-1 (2.0 g, 8.81 mmol, 1 eq) and dichloromethane (2 mL) were added into a reaction flask, oxalyl chloride (2.46 g, 19.38 mmol, 1.70 mL, 2.2 eq) and DMF (32.19 mg, 440.42 μmol, 33.88 μL, 0.05 eq) were added at 0° C. The reaction solution was stirred at 25° C. for 1 hour. The reaction solution was concentrated under reduced pressure to obtain crude acyl chloride, which was dissolved in 22 mL of dry dichloromethane. The aforementioned solution was added with LiCl (1.90 g, 44.81 mmol, 917.56 μL, 5 eq) and triethylamine (4.53 g, 44.81 mmol, 6.24 mL, 5 eq), and then added dropwise with a solution of intermediate 2-2 (1.59 g, 8.96 mmol, 1 eq) in dichloromethane (10 mL), and the reaction solution was stirred at 25° C. for 1 hour. The reaction solution was adjusted to pH~7 with a 5%-10% citric acid aqueous solution, and allowed to stand for liquid separation, then the aqueous phase was extracted with dichloromethane (200 ml×2) and the organic phase was dried over anhydrous sodium sulfate and concentrated under reduced pressure. The crude product was beaten with tert-methyl ether at room temperature (100 mL) and filtered to obtain an intermediate 3-2. $^1$H NMR (400 MHz, $CDCl_3$) δ7.83-7.92 (m, 2H), 7.47-7.51 (m, 4H), 7.31-7.331 (m, 2H), 7.21-7.24 (m, 3H), 4.76-4.80 (m, 1H), 4.18-4.21 (m, 1H), 3.35 (dd, 1H, J=2.8, 13.2 Hz), 3.08-3.10 (m, 1H), 2.83 (dd, 1H, J=9.6, 13.2 Hz).

Step 2: Synthesis of Intermediate 3-3

The intermediate 3-2 (1.0 g, 2.59 mmol, 1 eq), the intermediate 1 (2.63 g, 7.77 mmol, 3.0 eq) and dichloromethane (10 mL) were added into a reaction flask, and then added dropwise with trifluoroacetic acid (295.21 mg, 2.59 mmol, 191.69 μL, 1 eq) slowly at 25° C. The reaction solution was stirred at 25° C. for 1 hour. The reaction solution was then poured into a saturated aqueous solution of sodium bicarbonate (30 mL) and stirred for 10 minutes, and allowed to stand for phase separation. The aqueous phase was extracted with dichloromethane (30 mL×3). The organic phase was combined and dried over anhydrous sodium sulfate, and concentrated under reduced pressure to obtain a crude product. The crude product was separated and purified by preparative HPLC (chromatographic column: Waters Xbridge BEH C18 250*50 mm*10 um; mobile phase: [water (10 mM ammonium bicarbonate)-acetonitrile]; acetonitrile %: 45%-85%, 10 min) to obtain intermediate 3-3. $^1$H NMR (400 MHz, $CDCl_3$) δ 7.39-7.41 (m, 2H), 7.17-7.23 (m, 5H), 6.94-6.97 (m, 2H), 4.61-4.65 (m, 1H), 4.08-4.10 (m, 1H), 3.84-3.86 (m, 1H), 3.34-3.36 (m, 1H), 3.05-3.33 (m, 2H), 2.71-2.81 (m, 3H), 2.51-2.69 (m, 2H).

Step 3: Synthesis of Intermediate 3

The intermediate 3-3 (0.8 g, 1.65 mmol, 1 eq) and tetrahydrofuran (8 mL) were added into a reaction flask, and then lithium hydroxide monohydrate (207.46 mg, 4.94 mmol, 3.0 eq) and water (4 mL) were added at 0° C. The reaction solution was stirred at 25° C. for 4 hours. The reaction solution was concentration under reduced pressure, and extracted with water (50 mL) and ethyl acetate (30 mL×3). The organic phase was discarded, and the aqueous phase was adjusted to pH~2 with 2 N hydrochloric acid and concentrated under reduced pressure. The residue was dissolved in dichloromethane (50 mL) and filtered. The resulting filtrate was concentrated under reduced pressure to obtain intermediate 3, which was used directly in the next step without further purification. MS m/z (ESI): 326.0 [M+H]⁺.

Reference Example 4

Intermediate 4

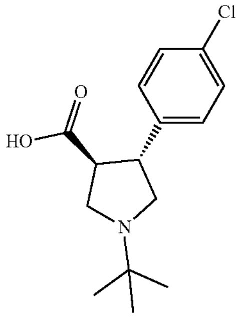

or

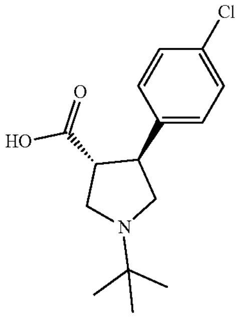

Synthetic Route:

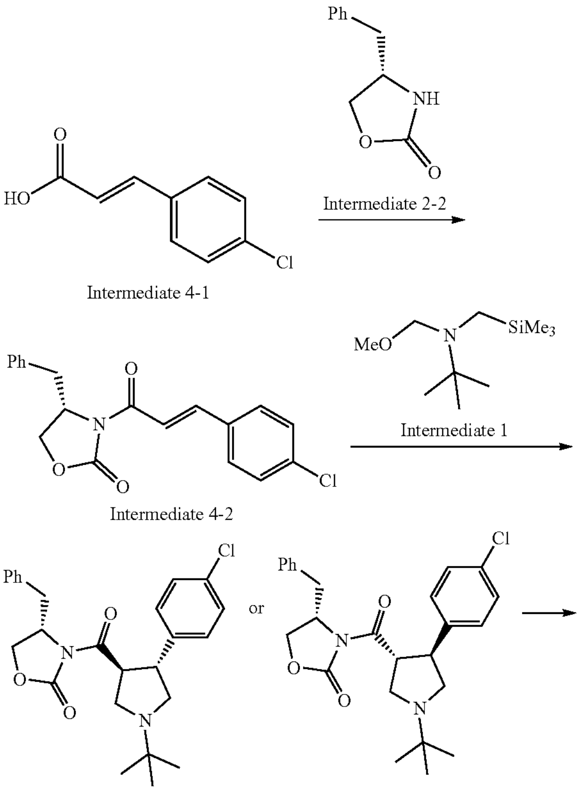

-continued

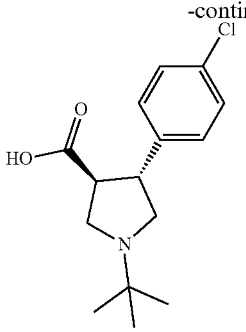

or

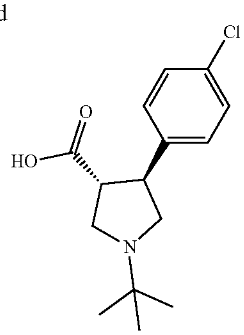

Intermediate 4

Step 1: Synthesis of Intermediate 4-2

The intermediate 4-1 (5 g, 27.38 mmol) and DCM (50 mL) were added into a reaction flask, then oxalyl chloride (7.65 g, 60.24 mmol) and DMF (200.13 mg, 2.74 mmol) were added sequentially at 0° C., and slowly heated to 20° C. for 1 hour. The reaction solution was concentrated under reduced pressure to obtain crude acyl chloride, which was dissolved in 55 mL of dichloromethane to obtain a solution. The resulting solution was cooled to 0° C., then added sequentially with LiCl (5.80 g, 136.78 mmol, 2.80 mL, 5 eq), triethylamine (13.84 g, 136.78 mmol, 19.04 mL, 5 eq) and the intermediate 2-2 (4.85 g, 27.36 mmol, 1 eq), and naturally heated to about 20° C. and stirred for 12 hours. The solution was adjusted to pH~7, allowed to stand for liquid separation, then the aqueous phase was added with dichloromethane (20 mL×3) for extraction, dried over anhydrous sodium sulfate, and concentrated under reduced pressure, and then purified by flash silica gel column chromatography (petroleum ether:ethyl acetate=1:0-4:1) to obtain intermediate 4-2. MS m/z (ESI): 342.1 [M+H]+.

Step 2: Synthesis of Intermediate 4-3

The intermediate 4-2 (2 g, 5.85 mmol) and the intermediate 1 (2.38 g, 7.02 mmol) in solution of DCM (20 mL) were added into a reaction flask, then triethylamine (333.60 mg, 2.93 mmol) and 500 mg of trifluoroacetic acid were added slowly via a syringe at 0° C. The reaction was conducted at 15° C. under stirring for 12 hours, 20 mL of saturated sodium bicarbonate solution was poured into the reaction solution until the pH was about 7. After allowed to stand for liquid separation, the aqueous phase was added with 10 mL of dichloromethane (×2) for extraction, and the organic phase was dried over anhydrous sodium sulfate and concentrated under reduced pressure, separated and purified by flash silica gel column chromatography (dichloromethane:methanol=1:0-10:1) to obtain intermediate 4-3, 1H NMR (400 MHz, $CDCl_3$) δ ppm 7.12-7.25 (m, 7H), 6.93 (dd, J=1.2, 6.8 Hz, 2H), 4.62 (m, 1H), 4.05-4.21 (m, 3H), 3.85 (q, J=8.0 Hz, 1H), 3.33 (t, J=9.2 Hz, 1H), 3.18 (t, J=8.0 Hz, 1H), 3.04 (dd, J=3.20, 13.60 Hz, 1H), 2.80 (br t, J=7.60 Hz, 1H), 2.73 (t, J=8.80 Hz, 1H), 2.66 (dd, J=8.8, 13.20 Hz, 1H), 1.05 (s, 9H). MS m/z (ESI): 441.3 [M+H]+.

Step 3: Synthesis of Intermediate 4

The intermediate 4-3 (300 mg, 680.33 μmol) in solution of THF (2.4 mL) were added into a reaction flask, then $LiOH \cdot H_2O$ (71.37 mg, 1.70 mmol) and $H_2O$ (1.2 mL) were added sequentially, and stirred at 15° C. for 3 hours. The reaction solution was concentrated under reduced pressure, added with 5 mL of water, added with 2 N hydrochloric acid to adjust the pH of the reaction solution to 2, and then extracted with ethyl acetate (10 mL×3). The organic phase was dried and directly concentrated under reduced pressure to obtain intermediate 4. MS m/z (ESI): 282.1 [M+H]⁺.

Reference Example 4

Intermediate 5

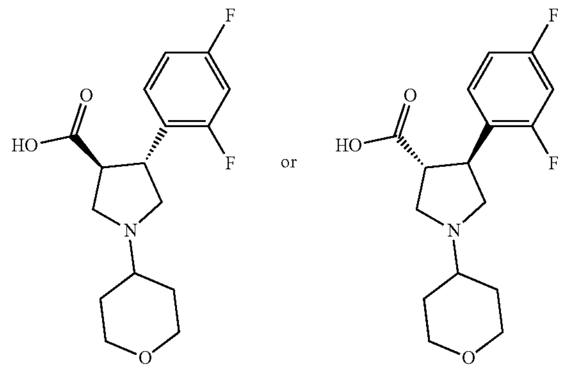

or

Synthetic Route:

Step 1: Synthesis of Intermediate 5-1

Compound 11-1 (1.6 g, 2.15 mmol, 52% purity, 1 eq), tetrahydropyran-4-one (431.15 mg, 4.31 mmol, 395.55 μL, 2 eq), dichloromethane (16 mL) and acetic acid (0.5 mL) were added into a reaction flask. The reaction was conducted at 20° C. under stirring for 2 hours, then added with $NaBH(OAc)_3$ (684.54 mg, 3.23 mmol, 1.5 eq) and kept at 20° C. for 16 hours, slowly added with 10 mL of a saturated aqueous solution of sodium bicarbonate until the pH was about 7, and extracted with dichloromethane (10 mL×3). The organic phases were combined, dried and concentrated under reduced pressure, and separated and purified by silica gel column chromatography (DCM:MeOH=1:0-19:1) to obtain intermediate 5-1. MS m/z (ESI): 471.2 $[M+H]^+$.

Step 2: Synthesis of Intermediate 5

Intermediate 5-1 (1.58 g, 1.98 mmol, purity of 59%, 1 eq) and THF (15 mL) were added into a reaction flask, and then lithium hydroxide monohydrate (207.83 mg, 4.95 mmol, 2.5 eq) and water (5 mL) were added. The reaction was conducted at 20° C. under stirring for 12 hours. The reaction mixture was concentrated under reduced pressure to remove

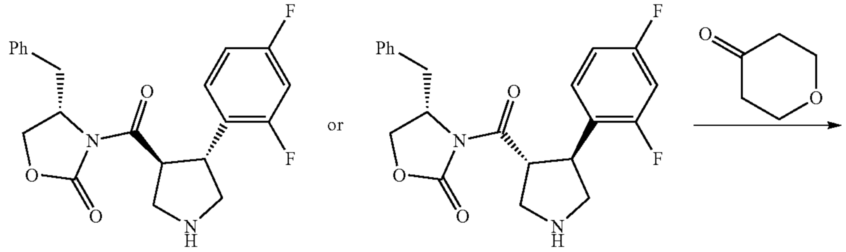

or

Compound 11-1

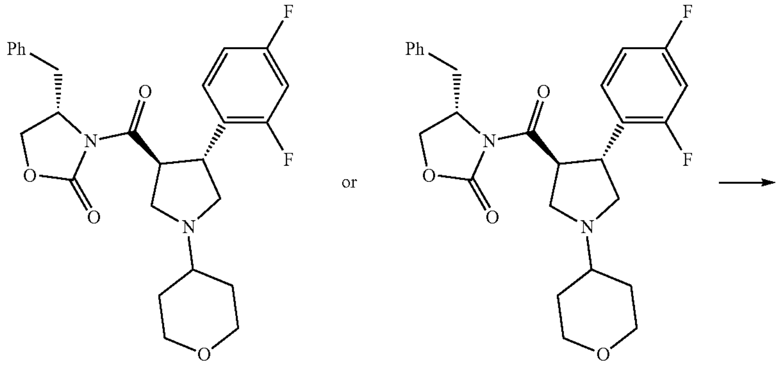

or

Intermediate 5-1

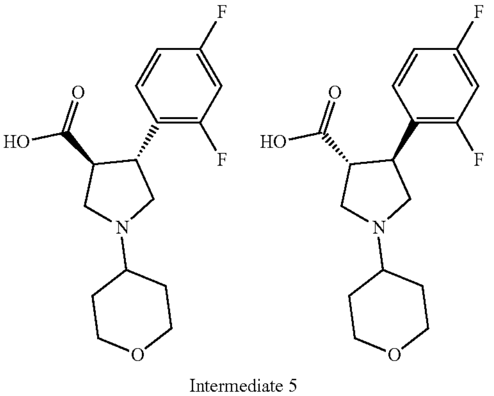

Intermediate 5

THE, and added with ethyl acetate (10 mL×3) for extraction. The organic phase was discarded, and the aqueous phase was adjusted to pH~5 with 2 N hydrochloric acid, and concentrated under reduced pressure to dryness. The residue was extracted with 5 mL of dichloromethane and filtered, and the resulting filtrate was concentrated under reduced pressure to obtain intermediate 5, MS m/z (ESI): 312.2 $[M+H]^+$.

Example 1

Compound 1

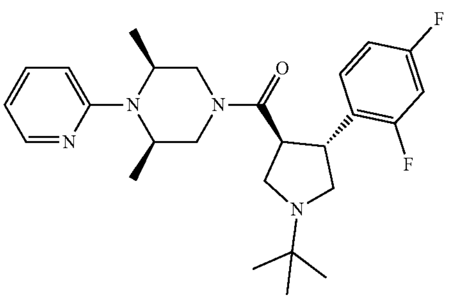

or

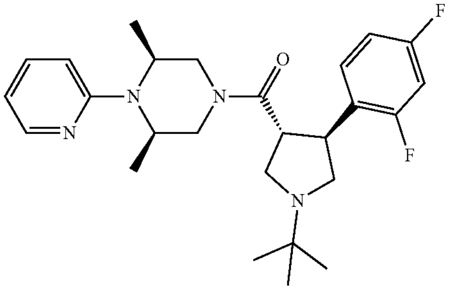

Synthetic Route:

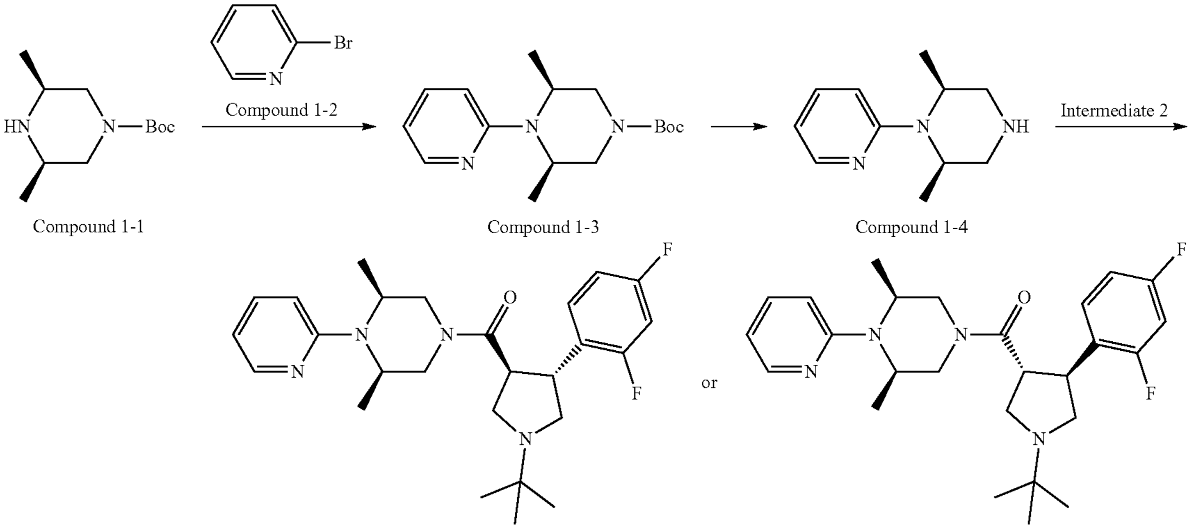

Compound 1-1

Compound 1-3

Compound 1-4 or

Compound 1

Step 1: Synthesis of Compound 1-3

Compound 1-1 (1.00 g, 4.67 mmol, 1 eq) and a compound 1-2 (737.25 mg, 4.67 mmol, 444.13 μL, 1 eq) in solution of toluene (20 mL) were added into a reaction flask, then sodium tert-butoxide (672.66 mg, 7.00 mmol, 1.5 eg) and tri-tert-butylphosphine palladium (238.47 mg, 466.62 μmol, 0.1 eq) were added, and stirred at 100° C. for 12 hours. The reaction solution was added into water (50 mL), and extracted with ethyl acetate (30 mL×3). The organic phase was dried over anhydrous sodium sulfate and filtered. The residue was separated and purified by column chromatography (gradient elution: petroleum ether:ethyl acetate (v/v)=100:0 to 80:20) to obtain compound 1-3. $^1H$ NMR (400 MHz, $CDCl_3$) δ: 8.21 (dd, J=4.8, 1.2 Hz, 1H), 7.50-7.45 (m, 1H), 6.61-6.59 (m, 1H), 6.55 (d, J=8.8 Hz, 1H), 4.51-4.32 (m, 2H), 4.11-3.87 (m, 2H), 3.22-3.03 (m, 2H), 1.51 (s, 9H), 1.22 (d, J=6.8 Hz, 6H).

Step 2: Synthesis of a Trifluoroacetate Salt of Compound 1-4

Compound 1-3 (0.30 g, 1.03 mmol, 1 eq) and dichloromethane (5 mL) were added into a reaction flask, then trifluoroacetic acid (1.54 g, 13.51 mmol, 1 mL, 13.12 eq) was added, and stirred at 15° C. for 2 hours. The reaction solution was concentrated under reduced pressure to obtain a trifluoroacetate salt of compound 1-4, which was used directly in the next step without further purification. MS m/z (ESI): 192.3 $[M+1]^+$. $^1H$ NMR (400 MHz, $CDCl_3$) δ: 9.19-9.05 (m, 1H), 8.02 (s, 1H), 7.21-7.02 (m, 2H), 4.48 (s, 2H), 3.47 (s, 4H), 1.50-1.26 (m, 6H).

Step 3: Synthesis of Compound 1

The compound 1-4 (300 mg, 1.06 mmol, 1 eq) and the intermediate 2 (251.27 mg, 823.05 μmol, 0.78 eq) were dissolved in dichloromethane (10 mL), and added with triethylamine (214.30 mg, 2.12 mmol, 294.77 μL, 2 eq) and tri-n-propylphosphonic anhydride (673.84 mg, 1.06 mmol, 629.76 μL, a 50% solution in ethyl acetate, 1 eq). The reaction was conducted under stirring at 15° C. for 1 hour. The reaction solution was concentrated under reduced pressure to obtain a crude product, which was separated and purified by preparative HPLC (column: Phenomenex Gemini-NX C18 250*50 mm*10 μm; mobile phase: [water (0.05% ammonia+10 mM ammonium bicarbonate)-acetonitrile]; acetonitrile %: 50%-70%, 10 min) to obtain compound 1. MS m/z (ESI): 457.2 $[M+1]^+$. $^1H$ NMR (400 MHz, DMSO) δ: 8.14-8.09 (m, 1H), 7.61-7.48 (m, 2H), 7.19-7.01

(m, 2H), 6.68-6.56 (m, 2H), 4.45-4.27 (m, 3H), 4.03-3.83 (m, 2H), 3.53-3.17 (m, 4H), 3.10-3.01 (m, 1H), 2.89-2.78 (m, 2H), 1.06 (m, 9H), 1.04-1.01 (m, 3H), 0.88-0.78 (m, 3H).

Example 2

Compound 2

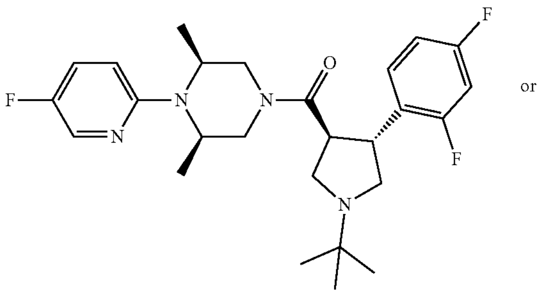

or

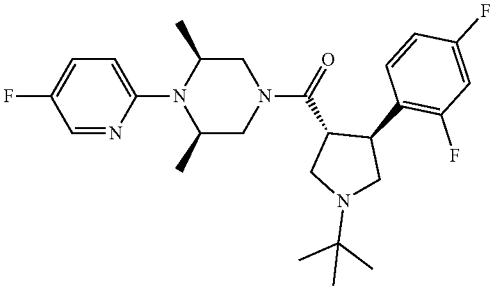

Synthetic Route:

Step 1: Synthesis of Compound 2-3

Compound 1-1 (0.50 g, 2.33 mmol, 1 eq) and an compound 2-1 (492.72 mg, 2.80 mmol, 266.48 μL, 1.2 eq) in solution of toluene (10 mL) were added into a reaction flask, then sodium tert-butoxide (336.32 mg, 3.50 mmol, 1.5 eq) and tri-tert-butylphosphine palladium (119.24 mg, 233.31 μmol, 0.1 eq) were added, and stirred at 100° C. for 12 hours. The reaction solution was filtered, the resulting filtrate was concentrated under reduced pressure, and the residue was separated and purified by column chromatography (gradient elution: petroleum ether:ethyl acetate (v/v)=100:0 to 80:20) to obtain compound 2-2. $^1$H NMR (400 MHz, $CDCl_3$) δ=8.09 (d, J=2.8 Hz, 1H), 7.29-7.24 (m, 1H), 6.54-6.51 (m, 1H), 4.23 (s, 2H), 4.08-3.78 (m, 2H), 3.18 (s, 2H), 1.51 (s, 9H), 1.16 (d, J=6.8 Hz, 6H).

Step 2: Synthesis of a Hydrochloride Salt of Compound 2-3

Compound 2-2 (0.40 g, 1.29 mmol, 1 eq) and ethyl acetate (4 mL) were added into a reaction flask, then hydrochloric acid/ethyl acetate (4M, 4 mL, 12.38 eq) was added and stirred at 15° C. for 1 hour. The reaction solution was concentrated under reduced pressure to obtain a hydrochloride salt of compound 2-3, which was directly used in the next reaction without purification. MS m/z (ESI): 210.3 [M+H]$^+$.

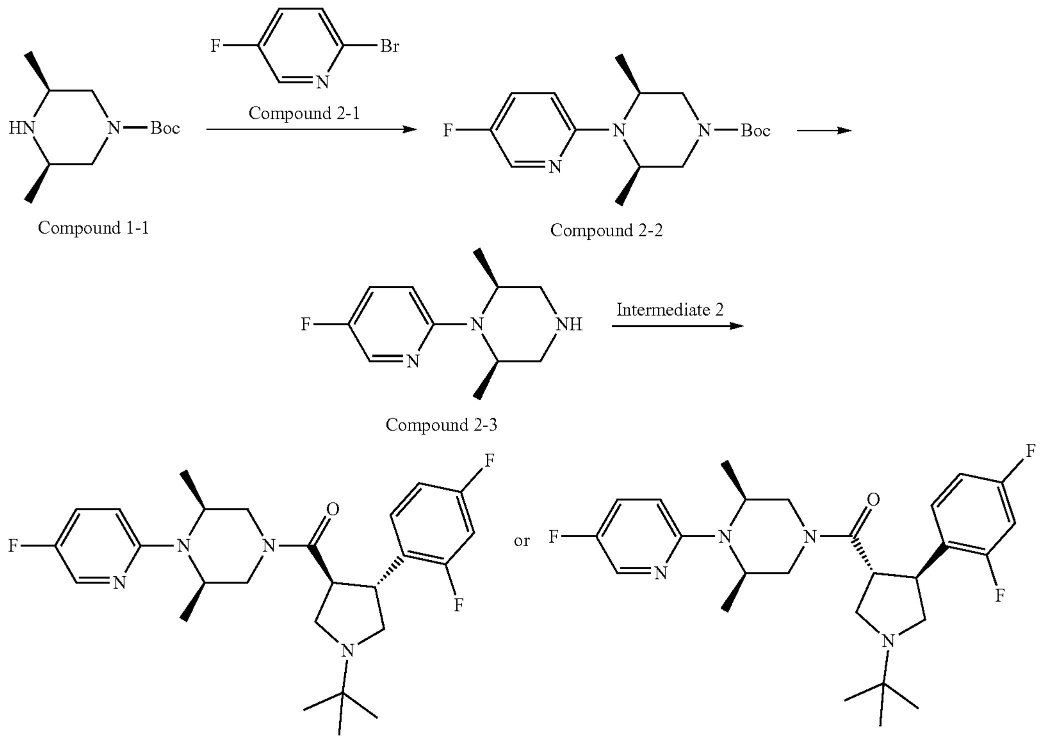

Compound 2

Step 3: Synthesis of Compound 2

The hydrochloride salt of the compound 2-3 (400 mg, 1.91 mmol, 1 eq) and the intermediate 2 (541.55 mg, 1.91 mmol, 1 eq) were dissolved in dichloromethane (10 mL), and added with triethylamine (386.84 mg, 3.82 mmol, 532.11 μL, 2 eq) and tri-n-propylphosphonic anhydride (1.22 g, 1.91 mmol, 1.14 mL, a 50% solution in ethyl acetate, 1 eq). The reaction was conducted under stirring at 15° C. for 1 hour. The reaction solution was concentrated under reduced pressure, and the obtained crude product was separated and purified by preparative HPLC (chromatographic column: Phenomenex Gemini-NX 80*40 mm*3 μm; mobile phase: [water (10 mM ammonium bicarbonate)-acetonitrile]; acetonitrile %: 35%-65%, 8 minutes) to obtain compound 2. MS m/z (ESI): 475.2 $[M+H]^+$. $^1H$ NMR (400 MHz, DMSO) δ=8.12-8.08 (m, 1H), 7.61-7.45 (m, 2H), 7.16-7.00 (m, 2H), 6.72-6.65 (m, 1H), 4.34-4.21 (m, 3H), 4.03-3.84 (m, 2H), 3.52-3.43 (m, 1H), 3.30-3.19 (m, 2H), 3.07-3.02 (m, 1H), 2.87-2.79 (m, 3H), 1.06 (s, 9H), 1.04-0.98 (m, 2H), 0.86 (d, J=6.8 Hz, 2H), 0.77 (d, J=6.8 Hz, 2H).

Example 3

Compound 3

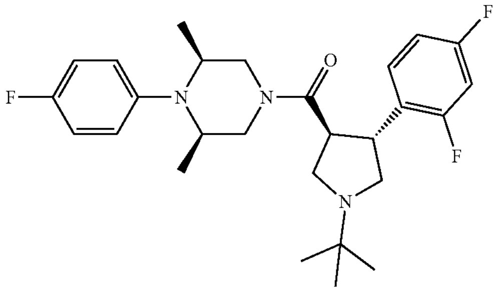

or

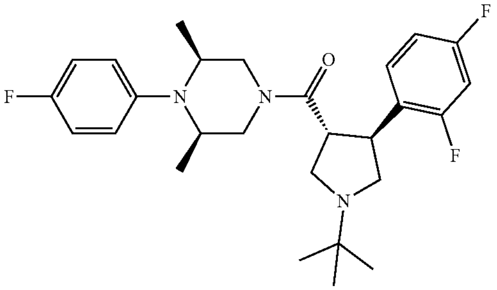

Synthetic Route:

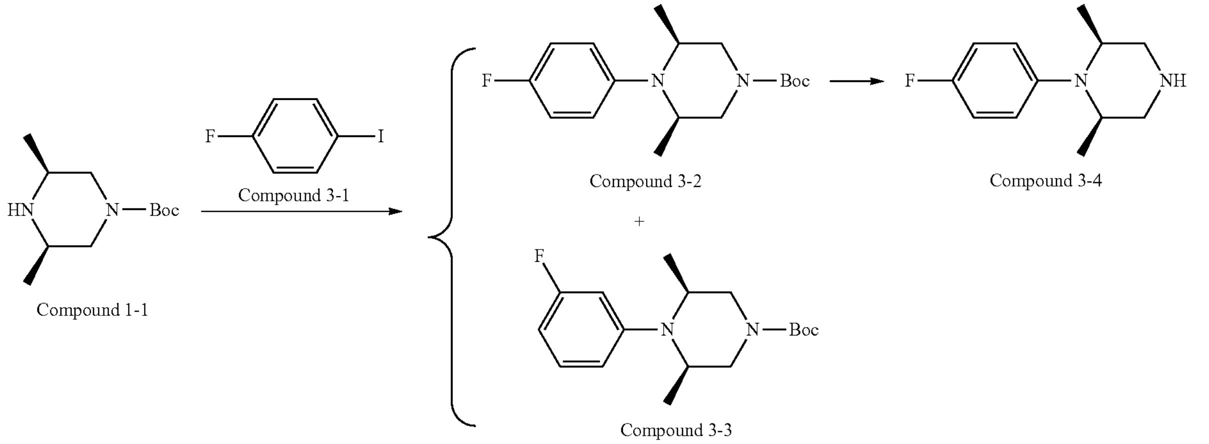

Compound 1-1

Compound 3-1

Compound 3-2

+

Compound 3-3

Compound 3-4

Compound 3-4

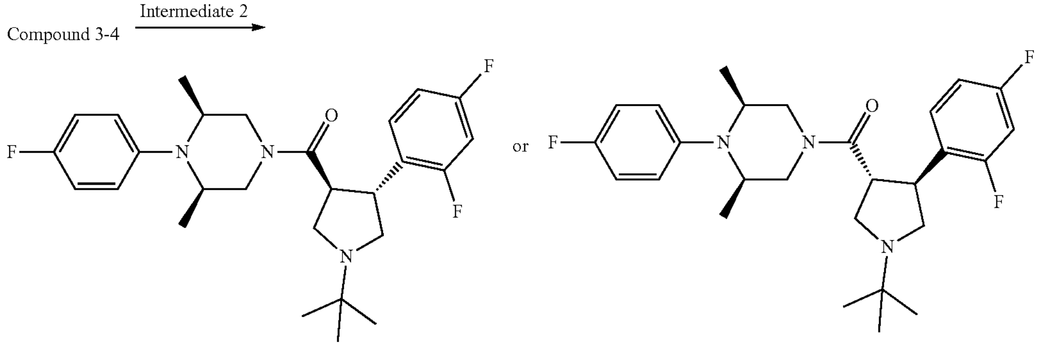

or

Compound 3

Step 1: Synthesis of Compounds 3-2 and 3-3

The compound 1-1 (1.74 g, 8.11 mmol, 1.2 eq), the compound 3-1 (1.5 g, 6.76 mmol, 777.20 μL, 1 eq) and dioxane (15 mL) were added into a sealed tube, and KHMDS (1 M, 8.11 mL, 1.2 eq) was added at 25° C. under nitrogen protection. The reaction solution was heated to 100° C. and stirred for 16 hours. Then the reaction solution was cooled and poured into 100 mL of saturated aqueous ammonium chloride solution, extracted with dichloromethane (150 mL×3), the organic phases were combined and dried over anhydrous sodium sulfate, and concentrated under reduced pressure to obtain a crude product. Then the crude product was purified by silica gel column chromatography (eluent: petroleum ether:ethyl acetate=1:0 to 1:1) to obtain compound 3-2 and compound 3-3. MS m/z (ESI): 309 $[M+H]^+$.

Compound 3-2: $^1H$ NMR (400 MHz, $CDCl_3$) δ ppm 7.06-7.15 (m, 2H), 6.95-7.05 (m, 2H), 4.01 (td, J=4.7, 2.3 Hz, 2H), 2.89 (ddd, J=9.5, 6.2, 3.2 Hz, 2H), 2.69 (br s, 2H), 1.50 (s, 9H), 0.72 (d, J=6.3 Hz, 6H);

Compound 3-3: $^1H$ NMR (400 MHz, $CDCl_3$) δ ppm 7.28-7.35 (m, 1H), 7.00-7.20 (m, 0.5H), 6.77-6.93 (m, 2.5H), 3.81 (br, 0.3H+1.7H=2H), 3.24 (br s, 1.7H), 3.11 (br dd, J=12.8, 7.9 Hz, 1.7H), 2.88-3.01 (m, 0.3H), 2.75 (br s, 0.3H), 1.56 (s, 9H), 0.93 (d, J=6.4 Hz, 5H), 0.78 (d, J=6.1 Hz, 1H).

Step 2: Synthesis of a Hydrochloride Salt of Compound 3-4

Compound 3-2 (300 mg, 972.79 μ mol, 1 eq) and dichloromethane (5 mL) were added into a reaction flask, and then a hydrogen chloride/ethyl acetate solution (4 M, 12.16 mL) was added at 0° C. The reaction solution was stirred at 25° C. for 1 hour. Then the reaction solution was concentrated under reduced pressure to obtain a hydrochloride salt of compound 3-4, which was used directly in the next step without further purification. MS m/z (ESI): 209 $[M+H]^+$.

Step 3: Synthesis of Compound 3

The intermediate 2 (150 mg, 529.45 μ mol, 1 eq), the hydrochloride of the compound 3-4 (275.68 mg) and dichloromethane (5 mL) were added into a reaction flask, and then triethylamine (267.88 mg, 2.65 mmol, 368.47 μL, 5 eq) and tri-n-propylphosphonic anhydride (505.38 mg, 794.18 μ mol, 472.32 μL, a 50% solution in ethyl acetate, 1.5 eq) were added. The reaction solution was stirred at 25° C. for 16 hours, added with 50 mL of water and 150 mL of dichloromethane, and allowed to stand for phase separation; then the aqueous phase was extracted with dichloromethane (10 mL×3). The organic phases were combined and dried over anhydrous sodium sulfate, and concentrated under reduced pressure to obtain a crude product. The crude product was separated and purified by preparative HPLC (chromatographic column; Phenomenex luna C18 250*50 mm*10 μm; mobile phase: [water (HCl)-acetonitrile]; acetonitrile %: 10%-40%, 10 min) to obtain a hydrochloride salt of compound 3. MS m/z (ESI): 474.4 $[M+H]^+$; $^1H$ NMR (400 MHz, DMSO-d6) δ ppm 7.67-8.13 (m, 3H), 7.16-7.45 (m, 4H), 4.55-4.58 (m, 1H), 4.00-4.07 (m, 6H), 3.61-3.67 (m, 2H), 3.25-3.30 (m, 3H), 1.39 (d, J=10 Hz, 9H), 0.92-0.97 (m, 6H).

Example 4

Compound 4

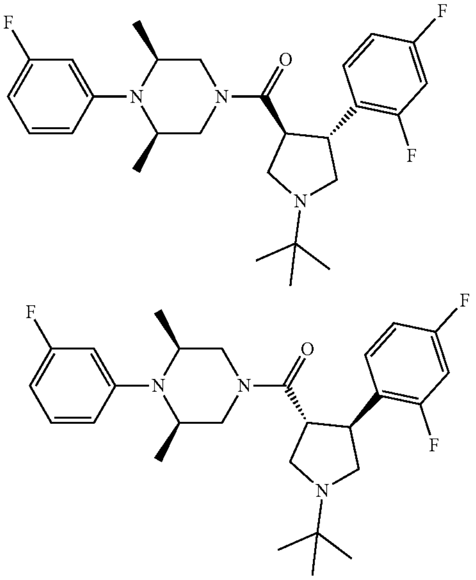

or

Synthetic Route:

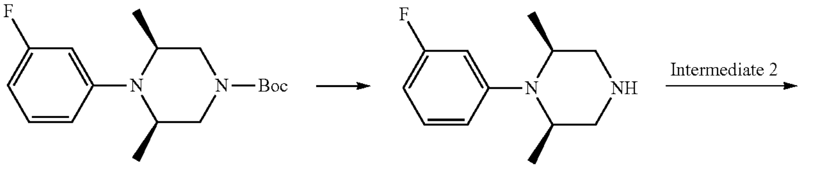

Compound 3-3

Compound 4-1

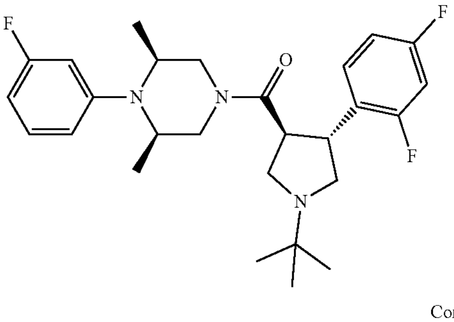

or

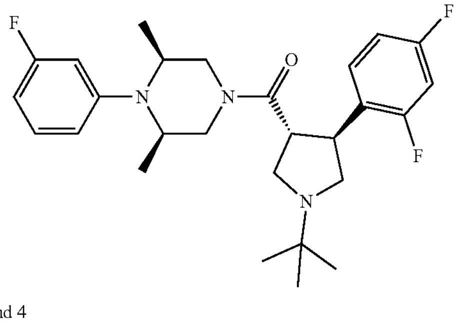

Compound 4

Step 1: Synthesis of a Hydrochloride Salt of Compound 4-1

Compound 3-3 (300 mg, 972.79 μmol, 1 eq) and dichloromethane (5 mL) were added into a reaction flask, and then hydrogen chloride/ethyl acetate solution (4 M, 12.16 mL) was added at 0° C. The reaction solution was stirred at 25° C. for 1 hour. Then the reaction solution was concentrated under reduced pressure to obtain a hydrochloride of compound 4-1, which was used directly in the next step without further purification. MS m/z (ESI): 209 $[M+H]^+$.

Step 2: Synthesis of Compound 4

Intermediate 2 (150 mg, 529.45 μmol, 1 eq), the hydrochloride salt of the compound 4-1 (250 mg) and dichloromethane (5 mL) were added into a reaction flask, and then triethylamine (267.88 mg, 2.65 mmol, 368.47 μL, 5 eq) and tri-n-propylphosphonic anhydride (505.38 mg, 794.18 μmol, 472.32 μL, a 50% solution in ethyl acetate, 1.5 eq) were added. The reaction solution was stirred at 25° C. for 16 hours, then added with 50 mL of water and 150 mL of dichloromethane, and allowed to stand for phase separation. The aqueous phase was extracted with dichloromethane (10 mL×3). The organic phases were combined and dried over anhydrous sodium sulfate, and concentrated under reduced pressure to obtain a crude product. The crude product was purified by preparative HPLC (chromatographic column: Phenomenex luna C18 250*50 mm*10 μm; mobile phase: [water (HCl)-acetonitrile]; acetonitrile %: 10%-40%, 10 min) to obtain a hydrochloride of compound 4. MS m/z (ESI): 474.4 $[M+H]^+$; $^1H$ NMR (400 MHz, DMSO-d6) δ ppm 7.68-7.86 (m, 2H), 7.08-7.34 (m, 5H), 3.97-4.05 (m, 6H), 3.48-3.52 (m, 3H), 3.28-3.49 (m, 3H), 1.39 (d, J=5.2 Hz, 9H), 0.81-0.95 (m, 6H)).

Example 5

Compound 5

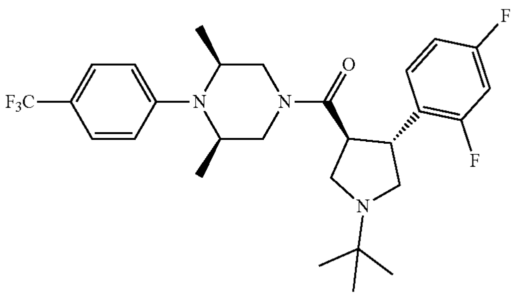

or

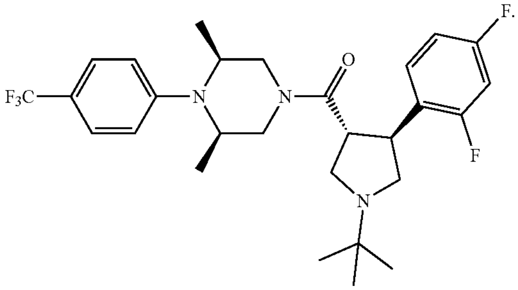

Synthetic Route:

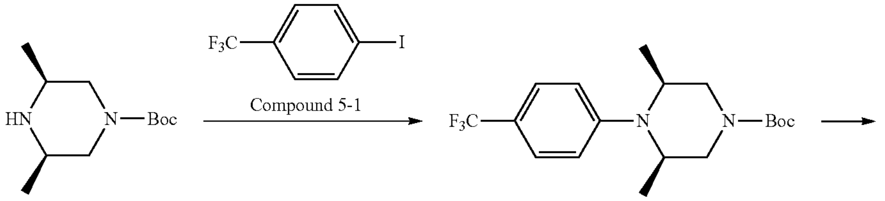

Compound 1-1

Compound 5-2

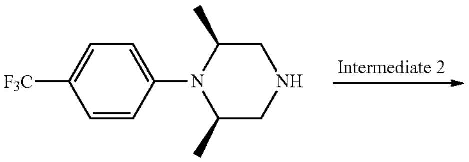

Compound 5-3

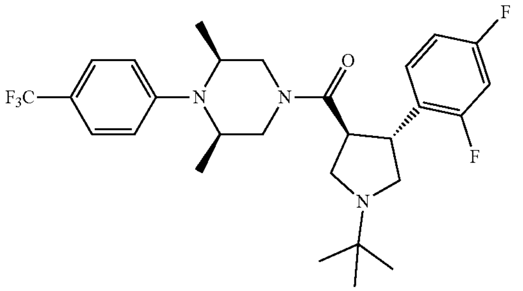

or

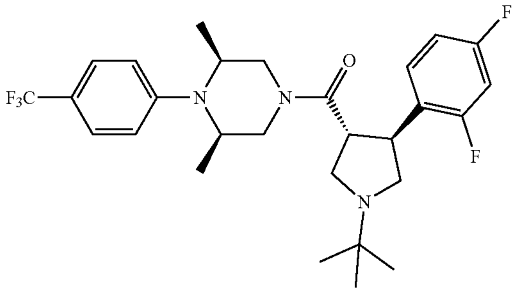

Compound 5

Step 1: Synthesis of Compound 5-2

The compound 1-1 (500 mg, 2.33 mmol, 1 eq), the compound 5-1 (1.27 g, 4.67 mmol, 686.08 μL, 2 eq), sodium tert-butoxide (448.43 mg, 4.67 mmol, 2) and toluene (5 mL) were added into a reaction flask, and then bis(tri-tert-butylphosphine) palladium (238.47 mg, 466.63 μmol, 0.2 eq) were added under nitrogen atmosphere. The reaction solution was stirred at 100° C. for 16 hours. After the end of reaction, the reaction solution was filtered, the filtrate was added with 10 mL of water and dichloromethane (10 mL), the aqueous phase was separated and extracted with dichloromethane (10 mL×2), and the organic phases were combined and dried over anhydrous sodium sulfate, and concentrated under reduced pressure to obtain a crude product. The crude product was separated by silica gel column chromatography (gradient elution: petroleum ether:ethyl acetate=1:0 to 10:1) to obtain compound 5-2. $^1$H NMR (400 MHz, $CDCl_3$) δ ppm 7.53 (d, J=8.80 Hz, 2H), 7.00 (br d, J=8.40 Hz, 2H), 3.42-3.59 (m, 6H), 1.51 (s, 9H), 1.01 (d, J=6.40 Hz, 6H).

Step 2: Synthesis of a Hydrochloride Salt of Compound 5-3

The compound 5-2 (300 mg, 837.06 μmol, 1 eq) and dichloromethane (2 mL) were added into a reaction flask, and then an ethyl acetate solution of hydrogen chloride (4 M, 33.66 mL, 160.86 eg) were added into a reaction flask. The reaction solution was stirred at 25° C. for 1 hour. After the raw materials disappeared, the reaction solution was concentrated under reduced pressure to obtain a crude hydrochloride salt product of compound 5-3, which was used directly in the next step without purification. MS m/z (ESI): 259 [M+H]$^+$.

Step 3: Synthesis of Compound 5

The intermediate 2 (192.24 mg, 542.85 μmol, 1 eq), the hydrochloride salt of the compound 5-3 (240 mg, 814.27 μmol, 1.5 eq) and dichloromethane (10 mL) were added into a reaction flask, and then triethylamine (274.65 mg, 2.71 mmol, 5 eq) and tri-n-propylphosphonic anhydride (518.17 mg, 814.27 μmol, a 50% solution in ethyl acetate, 1.5 eq) were added. The reaction solution was stirred at 25° C. for 1 hour. After completion, the reaction solution was added with 20 mL of water and 20 mL of dichloromethane, and allowed to stand for phase separation. Then the aqueous phase was extracted with dichloromethane (50 mL×3). The organic phases were combined and dried over anhydrous sodium sulfate, and concentrated under reduced pressure to obtain a crude product. The crude product was separated and purified by preparative HPLC (chromatographic column: Waters Xbridge BEH C18 250*50 mm*10 um; mobile phase: [water (10 mM ammonium bicarbonate)-acetonitrile]; acetonitrile %: 55%-75%, 10 min) to obtain compound 5. $^1$H NMR (400 MHz, $CDCl_3$) δ ppm 7.38-7.57 (m, 3H), 6.98 (br dd, J=12, 8.8 Hz, 2H), 6.70-6.91 (m, 2H), 3.33-4.06 (m, 6H), 2.81-3.32 (m, 6H), 1.14 (s, 9H), 0.89 (br d, J=5.2 Hz, 3H), 0.80 (d, J=6.4 Hz, 3H). MS m/z (ESI): 524 [M+H]$^+$.

Example 6

Compound 6

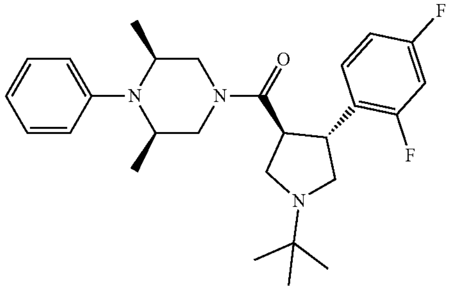

or

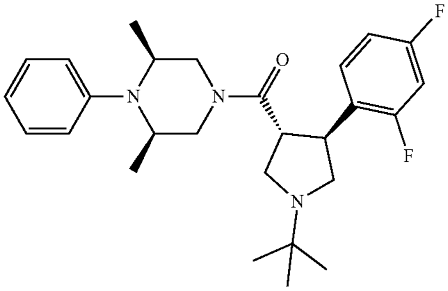

Synthetic Route:

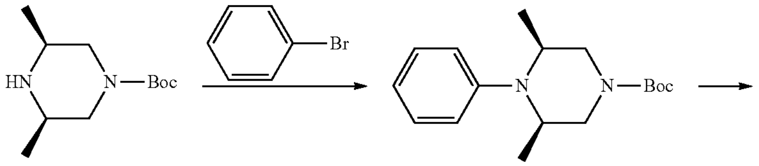

Compound 1-1

Compound 6-1

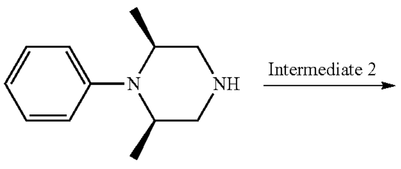

Compound 6-2

-continued

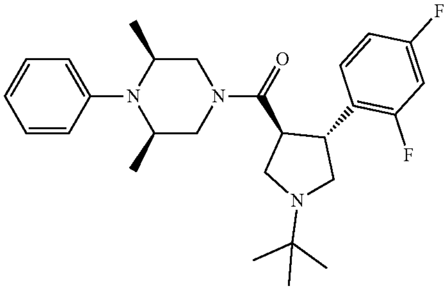

or

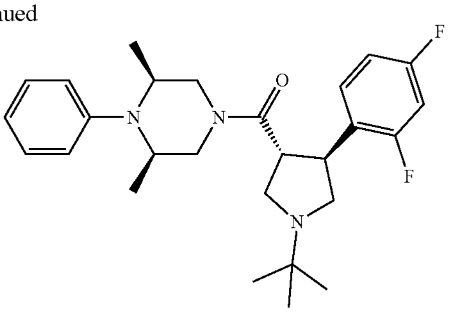

Compound 6

Step 1: Synthesis of Compound 6-1

Bromobenzene (1.10 g, 7.00 mmol, 738.15 μL, 1.5 eq), the compound 1-1 (1.0 g, 4.67 mmol, 1 eq), potassium tert-butoxide (785.40 mg, 7.00 mmol, 1.5 eq), and dimethyl sulfoxide (10 mL) were added into a microwave tube, and stirred at 120° C. for 0.5 h. After completion, the reaction solution was filtered, and the filtrate was added with 50 mL of water and ethyl acetate (10 mL) for extraction and separation. The aqueous phase was extracted with ethyl acetate (10 mL×3). The organic phases were combined and dried over anhydrous sodium sulfate, and concentrated under reduced pressure to obtain a crude product. The crude product was separated by silica gel column chromatography (gradient elution: petroleum ether:ethyl acetate=1:0 to 10:1) to obtain compound 6-1. $^1$H NMR (400 MHz, $CDCl_3$) δ ppm 7.28-7.33 (m, 2H), 7.09-7.18 (m, 3H), 3.80-4.06 (m, 2H), 2.99-3.16 (m, 2H)), 2.72-2.92 (m, 2H), 1.50 (s, 9H), 0.78 (d, J=6.4 Hz, 6H), Step 2: Synthesis of a Hydrochloride Salt of Compound 6-2

The compound 6-1 (120 mg, 413.22 μmol, 1 eq) and dichloromethane (5 mL) were added into a reaction flask, and then an ethyl acetate solution of hydrogen chloride-(4 M, 16.62 mL, 160.86 eq) were added. The reaction solution was stirred at 25° C. for 1 hour. The reaction solution was concentrated under reduced pressure to obtain a crude hydrochloride salt product of compound 6-2, which was used directly in the next step without further purification. MS m/z (ESI): 191.2 [M+H]$^+$.

Step 3: Synthesis of a Hydrochloride Salt of Compound 6

The hydrochloride salt of the compound 6-2 (94 mg, 494.00 μmol, 1 eq), the intermediate 2 (139.96 mg, 494.00 μmol, 1 eq) and dichloromethane (2 mL) were added into a reaction flask, and then triethylamine (249.94 mg, 2.47 mmol, 5 eq) and a tri-n-propylphosphonic anhydrideethyl acetate solution at a concentration of 50% (471.54 mg, 741.00 μmol, 1.5 eq) were added. The reaction solution was stirred at 25° C. for 1 hour, then added with 20 mL of water and 20 mL of dichloromethane, and allowed to stand for phase separation. Then the aqueous phase was extracted with dichloromethane (20 mL×3). The organic phases were combined and dried over anhydrous sodium sulfate, and concentrated under reduced pressure to obtain a crude product. The crude product was separated and purified by preparative HPLC (chromatographic column: Phenomenex luna C18 250*50 mm*10 μm; mobile phase: [water (HCl)-acetonitrile]; acetonitrile %: 10%-40%, 10 min) to obtain a hydrochloride salt of compound 6. $^1$H NMR ($CDCl_3$, 400 MHz) δ 7.30-7.39 (m, 1H), 7.21 (br d, 2H, J=7.6 Hz), 7.08 (br d, 1H, J=6.4 Hz), 6.9-7.0 (m, 2H), 6.6-6.9 (m, 2H), 4.2-4.5 (m, 1H), 3.8-4.0 (m, 1H), 3.5-3.7 (m, 1H), 3.10-3.35 (m, 1H), 3.0-3.2 (m, 2H), 2.3-3.0 (m, 6H), 1.06 (br s, 9H), 0.4-0.7 (m, 6H). MS m/z (ESI): 456.4 [M+H]$^+$.

Example 7

Compound 7

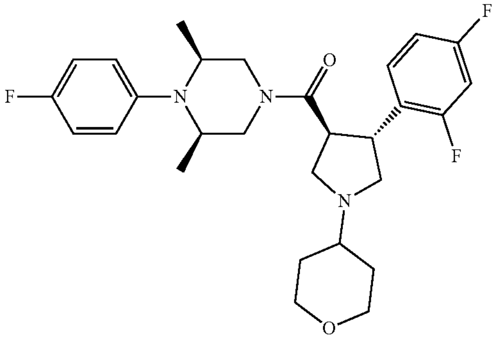

or

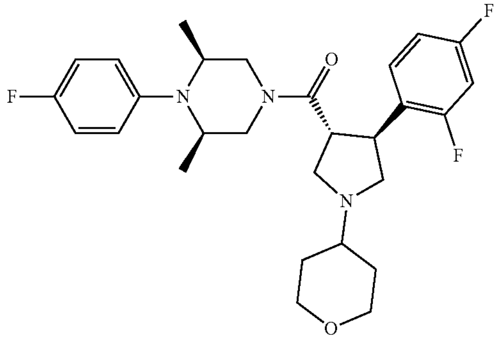

Synthetic Route:
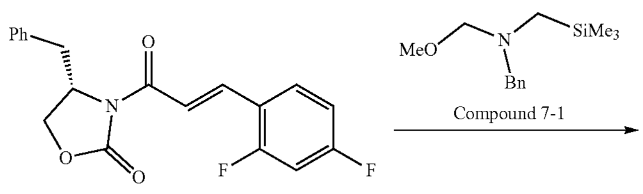
Intermediate 2-3
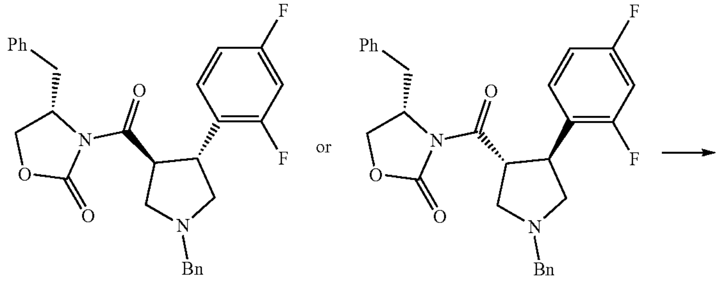
Compound 7-2
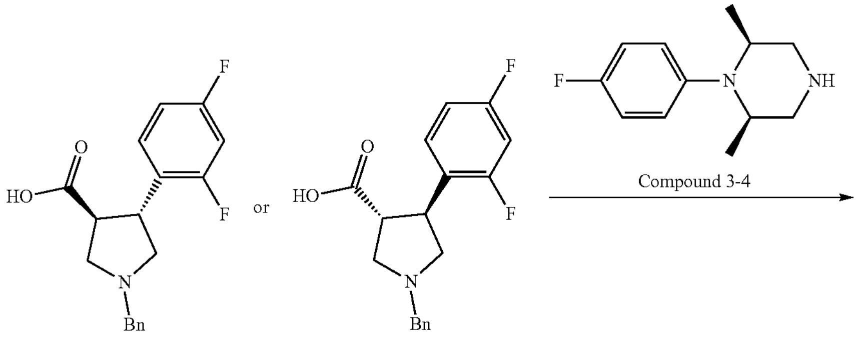
Compound 7-3
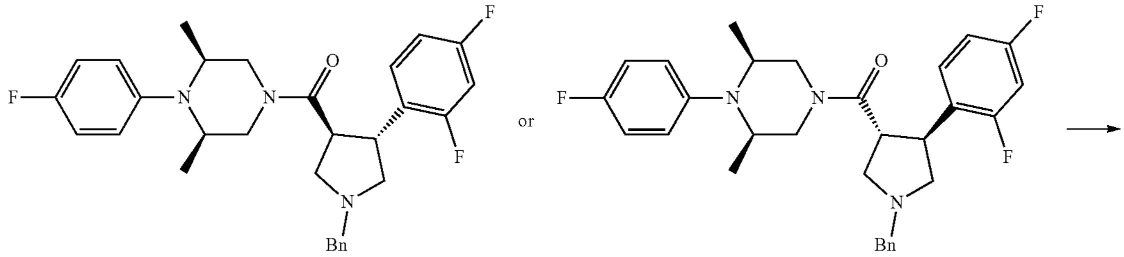
Compound 7-4
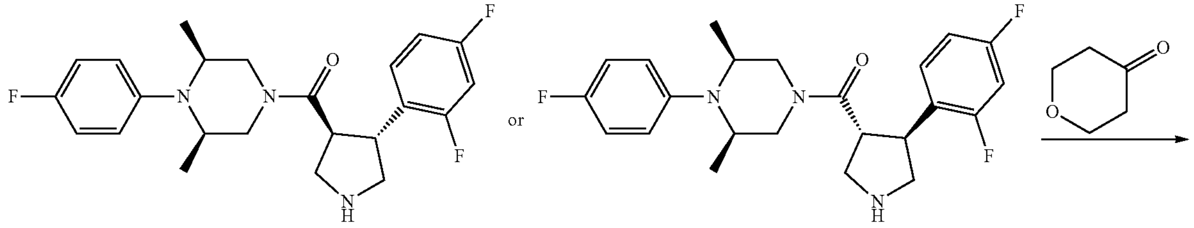
Compound 7-5

-continued

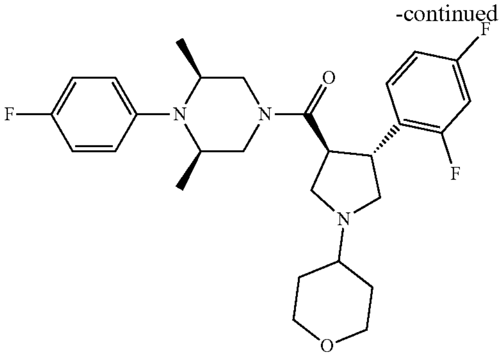

or

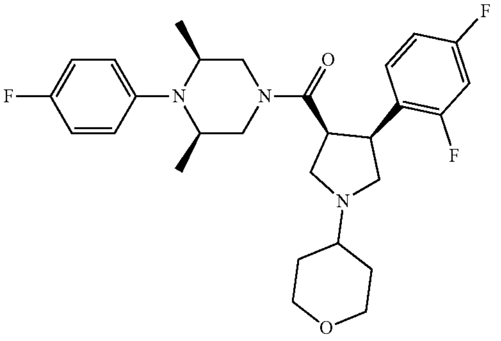

Compound 7

Step 1: Synthesis of Compound 7-2

The intermediate 2-3 (2.0 g, 5.83 mmol, 1 eq), the compound 7-1 (1.66 g, 6.99 mmol, 1.2 eq) and DCM (20 mL) were added into a reaction flask, and then TFA (132.84 mg, 1.17 mmol, 86.26 μL, 0.2 eq) were added dropwise slowly at 25° C. After the dropwise addition, the reaction solution was stirred at 25° C. for 1 hour. After completion of reaction, the reaction solution was poured into a saturated aqueous solution of sodium bicarbonate (20 mL) and stirred for 10 minutes, and allowed to stand for phase separation. The aqueous phase was extracted with dichloromethane (100 mL×3). The organic phases were combined and dried over anhydrous sodium sulfate, and concentrated under reduced pressure to obtain a crude product. The crude product was separated and purified by silica gel column chromatography (petroleum ether:ethyl acetate=5:1) to obtain compound 7-2. $^1$H NMR (400 MHz, $CDCl_3$) δ 7.25-7.28 (m, 5H), 7.19-7.20 (m, 4H), 7.07-7.19 (m, 2H), 6.70-6.78 (m, 2H), 4.60-4.61 (m, 1H), 407-4.18 (m, 4H), 3.56-3.68 (m, 2H), 3.04-3.17 (m, 3H), 2.67-2.71 (m, 3H).

Step 2: Synthesis of Compound 7-3

The compound 7-2 (1.3 g, 2.73 mmol, 1 eq) and THF (13 mL) were added into a reaction flask, and then lithium hydroxide monohydrate (343.42 mg, 8.18 mmol, 3.0 eq) and $H_2O$ (6 mL) were added at 0° C. The reaction solution was stirred at 25° C. for 4 hours. Then the reaction solution was concentrated to dryness under reduced pressure, and extracted with water (50 mL) and ethyl acetate (30 mL×3). The aqueous phase was adjusted to pH=2 with 2 N hydrochloric acid, concentrated under reduced pressure; the residue was dissolved with dichloromethane (50 mL) and filtered, and the resulting filtrate was concentrated under reduced pressure to obtain a crude compound 7-3, which was used directly in the next step without further purification. $^1$H NMR (400 MHz, $CDCl_3$) δ ppm 7.57 (br d, J=7.2 Hz, 2H), 7.38-7.47 (m, 4H), 6.73-6.84 (m, 2H), 4.39 (s, 2H), 4.10-4.34 (m, 1H), 3.67-3.74 (m, 3H), 3.26-3.54 (m, 2H).

Step 3: Synthesis of Compound 7-4

The hydrochloride salt of the compound 3-4 (131.11 mg, 535.72 μmol, 1.0 eq), the compound 7-3 (170 mg, 535.72 μmol, 1.0 eq) and DCM (5 mL) were added into a reaction flask, and then triethylamine (271.05 mg, 2.68 mmol, 372.83 μL, 5 eq) and a tri-n-propylphosphonic anhydrideethyl acetate solution (511.37 mg, 803.58 μmol, 1.5 eq) were added at a concentration of 50%. The reaction solution was stirred at 25° C. for 1 hour, then added with 10 mL of water and 20 mL of dichloromethane, and allowed to stand for phase separation. The aqueous phase was extracted with dichloromethane (20 mL×3). The organic phases were combined and dried over anhydrous sodium sulfate, and concentrated under reduced pressure to obtain a crude product, which was purified by silica gel column chromatography (petroleum ether:ethyl acetate=1:0 to 1:1) to obtain compound 7-4. $^1$H NMR ($CDCl_3$, 400 MHz) δ 7.4-7.5 (m, 1H), 7.3 (m, 2H), 7.20-7.26 (m, 2H), 7.2 (m, 1H), 6.9-7.0 (m, 4H), 6.7-6.8 (m, 1H), 6.6-6.7 (m, 1H), 4.48 (tdd, J=2.4, 7.2, 10 Hz, 1H), 3.9-4.0 (m, 1H), 3.6-3.8 (m, 2H), 3.4-3.5 (m, 1H), 3.2-3.4 (m, 1H), 3.0-3.2 (m, 1H), 2.8-3.0 (m, 3H), 2.4-2.7 (m, 4H), 0.40-0.66 (m, 6H).

Step 4: Synthesis of a Hydrochloride Salt of Compound 7-5

Wet Pd/C (0.3 g, with a palladium content of 10%) and anhydrous methanol (20 mL) were added into a reaction flask, then the compound 7-4 (170 mg, 334.92 μmol, 1 eg) and concentrated hydrochloric acid (0.5 mL), were added and stirred at 40° C. for 3 hours under an atmosphere of 40 psi $H_2$. The reaction solution was filtered through diatomaceous earth, and the filter cake was washed with methanol (30 mL×2). The filtrate was concentrated under reduced pressure to obtain a crude hydrochloride salt product of compound 7-5, which was used directly in the next step without purification. MS m/z (ESI): 418.2 $[M+H]^+$.

Step 5: Synthesis of Compound 7

The hydrochloride salt of the compound 7-5 (152 mg, 334.86 μmol, 1 eq), tetrahydropyran-4-one (67.05 mg, 669.71 μmol, 61.51 μL, 2 eq), triethylamine (67.77 mg, 669.71 μmol, 93.22 μL, 2 eq), DCM (10 mL) and AcOH (0.1 mL) were added into a reaction flask. The reaction solution was stirred at 25° C. for 2 hours, then NaBH(OAc) 3 (106.45 mg, 502.28 μmol, 1.5 eg) were added, and stirred continually at 25° C. for 16 hours. Then the reaction solution was extracted by adding 5 mL of a saturated aqueous solution of sodium bicarbonate and dichloromethane (10 mL×3). The organic phases were combined, dried over anhydrous sodium sulfate and concentrated under reduced pressure to obtain a crude product. The crude product was separated and purified by preparative HPLC (chromatographic column: Waters Xbridge BEH C18 250*50 mm*10 μm; mobile phase: [water (10 mM ammonium bicarbonate)-acetonitrile]; acetonitrile %: 45%-75%, 10 min) to obtain compound 7. $^1$H NMR (400 MHz, $CDCl_3$) δ ppm 7.38-7.55 (m, 1H), 6.93-7.11 (m, 4H), 6.71-6.92 (m, 2H), 4.49-4.63 (m, 1H), 3.89-4.06 (m, 3H), 3.49-3.65 (m, 1H), 3.29-3.47 (m, 3H), 3.10-3.24 (m, 1H), 2.68-3.08 (m, 5.5H), 2.30-2.58 (m, 2.5H), 1.82 (br d, J=11.0 Hz, 2H), 1.62 (br t, J=11.5 Hz, 2H), 0.44-0.77 (m, 6H). MS m/z (ESI): 502.3 $[M+H]^+$.

Example 8

Compound 8

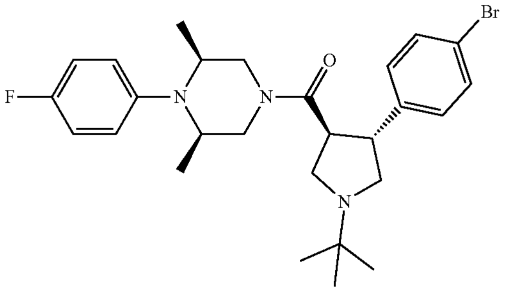

or

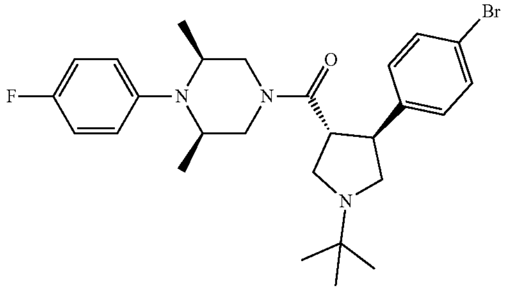

Synthetic Route:

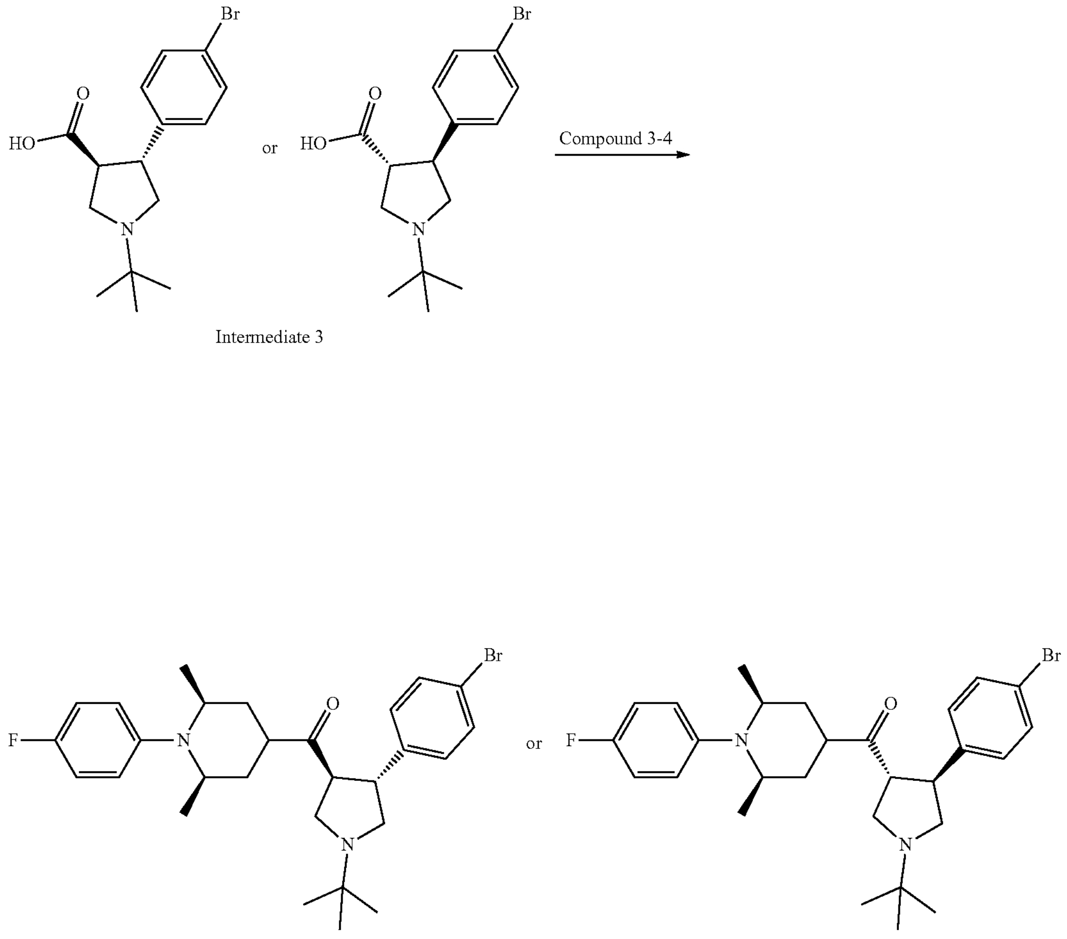

or

Intermediate 3 or

Compound 8

Step 1: Synthesis of a Hydrochloride Salt of Compound 8

The hydrochloride salt of the compound 3-4 (90.02 mg, 367.84 μmol), the intermediate 3 (200 mg, 367.84 μmol) and dichloromethane (5 mL) were added into a reaction flask, and then TEA (186.11 mg, 1.84 mmol) and a solution of n-propyl phosphoric anhydride 50% ethyl acetate (351.12 mg, 551.76 μmol) were added. The reaction solution was stirred at 25° C. for 1 hour. After completion of reaction, the reaction solution was added with 10 mL of water, and extracted with dichloromethane (3× 10 mL). The organic phases were combined and dried over anhydrous sodium sulfate, and concentrated under reduced pressure to obtain a crude product. The crude product was separated and purified by preparative HPLC (column: Phenomenex Luna 80*30 mm*3 μm; mobile phase: [water (HCl)-acetonitrile]; acetonitrile %: 1%-35%, 8 min) to obtain a hydrochloride salt of compound 8. $^1H$ NMR (DMSO-d6, 400 MHz) δ 10.8-12.0 (m, 1H), 7.65 (d, 2H, J=8.4 Hz), 7.50-7.56 (m, 3H), 7.35-7.47 (m, 3H), 4.41-4.55 (m, 1H), 3.51-3.90 (m, 11H), 1.38 (s, 9H), 0.56-0.84 (m, 6H). MS m/z (ESI): 516.2 $[M+H]^+$.

Example 9

Compound 9

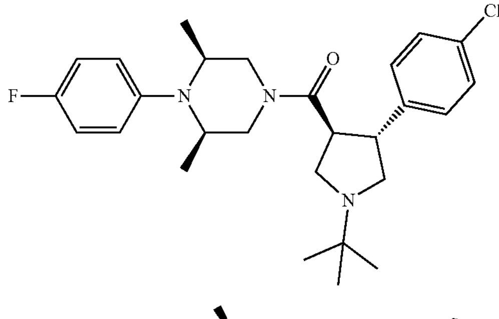

or

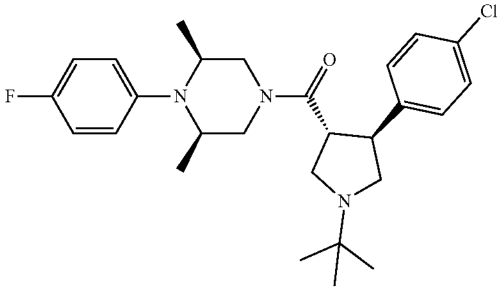

Synthetic Route:

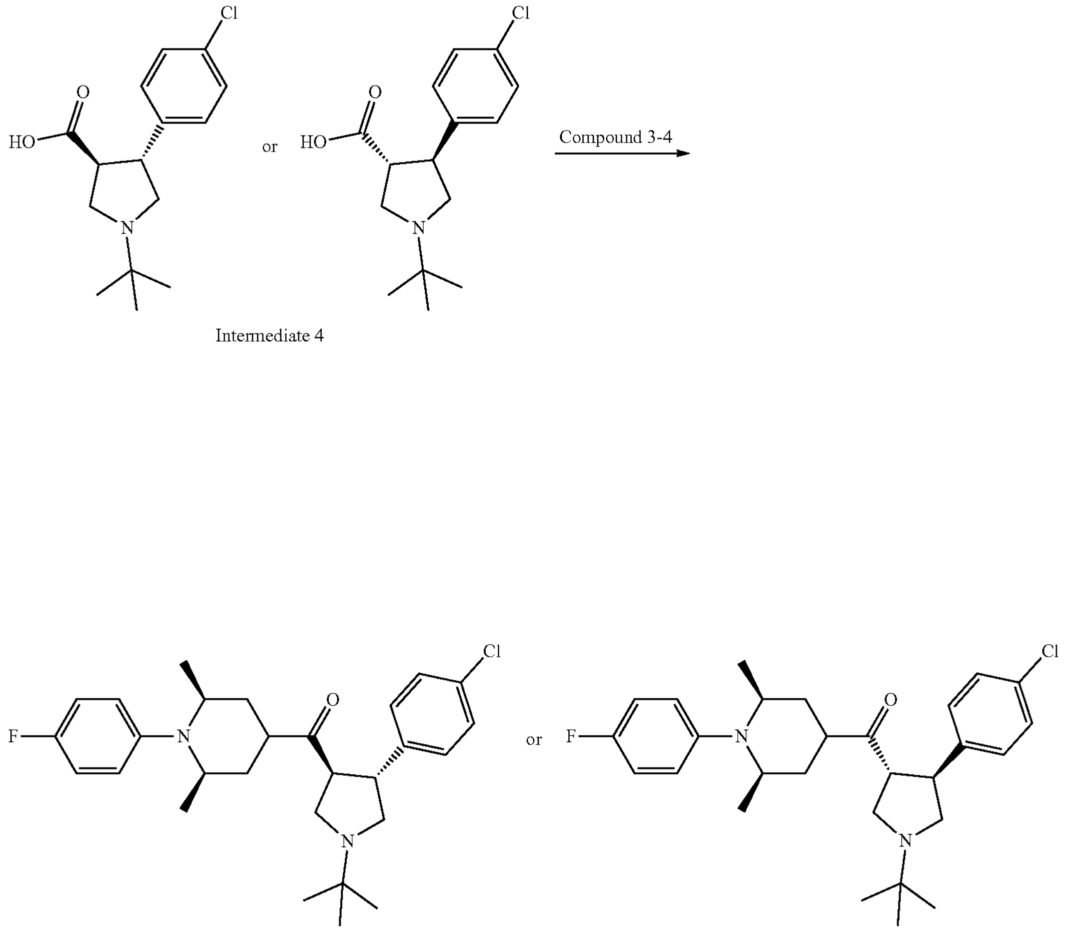

Intermediate 4

Compound 9

Step 1: Synthesis of Compound 9

The intermediate 4 (150 mg, 399.25 μmol), the hydrochloride salt of the compound 3-4 (97.71 mg, 399.25 μmol) and dichloromethane (5 mL) were added into a reaction flask, then triethylamine (121.20 mg, 1.20 mmol) and a solution of tri-n-propylphosphonic anhydride in ethyl acetate (381.10 mg, 598.88 μmol, 50%) were added, and stirred at 25° C. for 12 hours. The reaction solution was extracted by adding 5 mL of water and 5 mL of dichloromethane for 3 times; the organic phase was dried over anhydrous sodium sulfate and concentrated under reduced pressure. The crude product was separated by preparative HPLC (chromatographic column: Phenomenex C18 75*30 mm*3 μm; mobile phase: [Water (10 mM ammonium bicarbonate)-acetonitrile]; acetonitrile %: 30%-80%, 8 min) to obtain compound 9. $^1$H NMR (400 MHz, $CD_3OD$) δ ppm 7.36-7.44 (m, 3H), 7.31 (s, 1H), 6.90-7.16 (m, 4H), 4.36-4.48 (m, 1H), 3.63-3.72 (m, 1H), 3.40-3.58 (m, 2H), 3.08-3.27 (m, 2H), 2.62-3.05 (m, 3H), 2.40-2.57 (m, 2H), 1.52-1.65 (m, 1H), 1.18 (s, 9H), 0.71 (d, J=6.0 Hz, 1H), 0.62-0.69 (m, 3H), 0.46 (d, J=6.4 Hz, 2H). MS m/z (ESI): 472.3 $[M+H]^+$.

Example 10
Compound 10
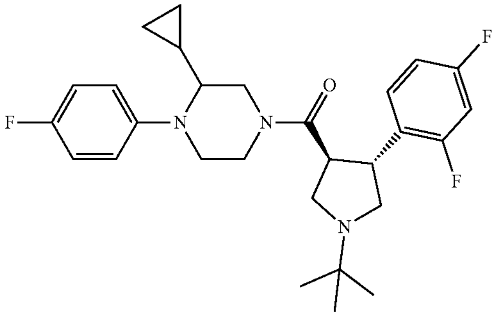
or
-continued
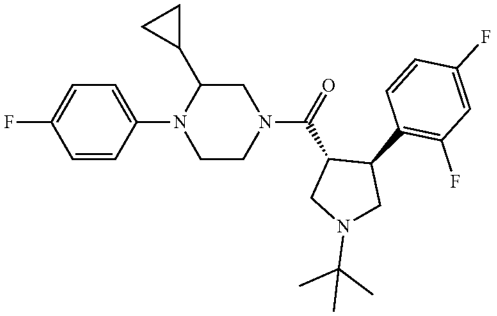
Synthetic Route:
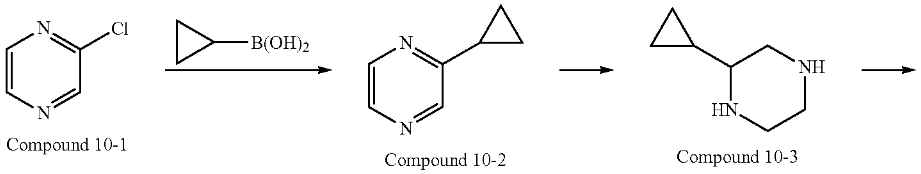
Compound 10-1 Compound 10-2 Compound 10-3
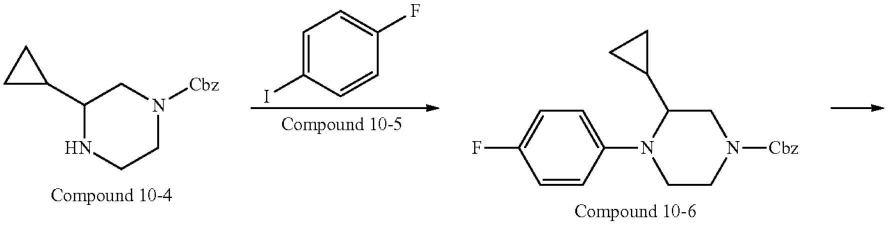
Compound 10-4 Compound 10-6
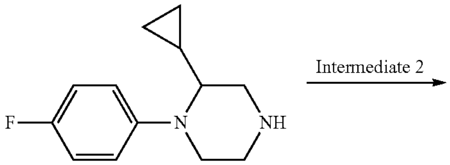
Compound 10-7
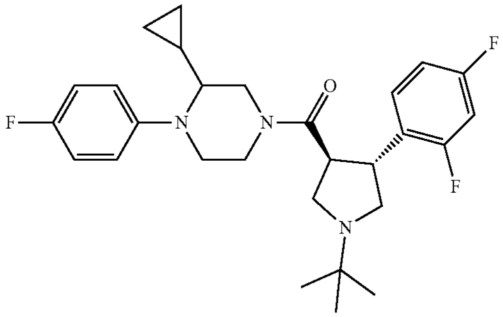
or
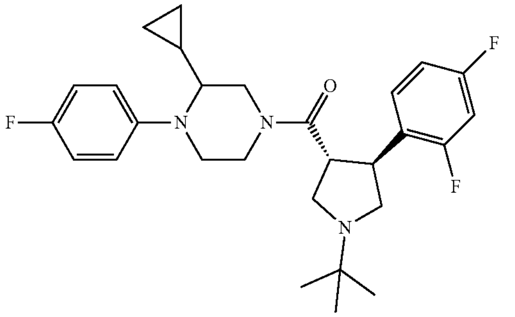
Compound 10

Step 1: Synthesis of Compound 10-2

The compound 10-1 (2.0 g, 17.46 mmol, 1.56 mL, 1 eq), cyclopropylboronic acid (1.50 g, 17.46 mmol, 1 eq) and toluene-$H_2O$ (22 mL, 10:1) were added into a reaction flask, then $Cs_2CO_3$ (17.07 g, 52.39 mmol, 3 eq), and Pd(dppf)$Cl_2$ (1.28 g, 1.75 mmol, 0.1 eq) were added under $N_2$ atmosphere, and stirred at 110° C. for 16 hours. After completion of reaction, the reaction solution was concentrated under reduced pressure, added with 20 ml of water and 20 mL of ethyl acetate, and allowed to stand for phase separation. The aqueous phase was extracted with ethyl acetate (3×10 mL). The organic phases were combined and dried over anhydrous sodium sulfate, and concentrated under reduced pressure to obtain a crude product. The crude product was subjected to flash silica gel column chromatography (petroleum ether:ethyl acetate=1:0 to 10:1) to obtain compound 10-2. MS m/z (ESI): 121.1 $[M+H]^+$.

Step 2: Synthesis of Compound 10-3

$PtO_2$ (75.60 mg, 332.91 μmol, 0.05 eq) and acetic acid (44 mL) were added into a reaction flask, and then the compound 10-2 (0.8 g, 6.66 mmol, 1 eq) was added. The reaction solution was stirred at 25° C. for 16 hours under $H_2$ (15 PSI) atmosphere. After completion of reaction, the reaction solution was filtered through diatomaceous earth, and the filter cake was washed with methanol (30 mL×2) and the filtrate was concentrated under reduced pressure to obtain a crude acetate product of compound 10-3, which was used directly in the next step without purification. MS m/z (ESI): 127.1 $[M+H]^+$.

Step 3: Synthesis of Compound 10-4

The crude acetate product of the compound 10-3 (1.64 g, 8.81 mmol, 1 eq) and 1,4-dioxane (50 mL) and $H_2O$) (25 mL) were added into a reaction flask, and then odium bicarbonate (4.44 g, 52.83 mmol, 2.05 mL, 6 eq) and benzyl chloroformate (751.05 mg, 4.40 mmol, 625.88 μL, 0.5 eq) were added at 0° C. The reaction solution was stirred at 25° C. for 1 hour, added with ethyl acetate (10 mL), and allowed to stand for phase separation. The aqueous phase was extracted with ethyl acetate (3×10 mL). The organic phases were combined and dried over anhydrous sodium sulfate, and concentrated under reduced pressure to obtain a crude product. The crude product was purified by flash silica gel column chromatography (petroleum ether:ethyl acetate=1:0 to 1:1) to obtain compound 10-4. $^1H$ NMR ($CDCl_3$, 400 MHz) δ 7.31-7.50 (m, 6H), 5.10-5.18 (m, 2H), 4.01-4.05 (m, 2H), 2.91-2.97 (m, 2H), 2.67-2.78 (m, 2H), 1.77 (br s, 1H), 0.71-0.75 (m, 1H), 0.49-0.51 (m, 2H), 0.18-0.30 (m, 2H).

Step 4: Synthesis of Compound 10-6

The compound 10-4 (500 mg, 1.92 mmol, 1 eq), the compound 10-5 (852.75 mg, 3.84 mmol, 441.84 μL, 2 eq), sodium tert-butoxide (369.15 mg, 3.84 mmol, 2 eq) and toluene (5 mL) were added into a reaction flask, and then bis(tri-tert-butylphosphine) palladium (196.31 mg, 384.13 μmol, 0.2 eq) was added under nitrogen atmosphere, and the reaction solution was stirred at 100° C. for 16 hours. The reaction solution was concentrated under reduced pressure, then added with 20 mL of dichloromethane and 20 mL of water, and allowed to stand for phase separation. The aqueous phase was extracted with dichloromethane (20 mL×3). The organic phases were combined and dried over anhydrous sodium sulfate, filtered and concentrated under reduced pressure to obtain a crude product, which was purified by flash silica gel column chromatography (petroleum ether:ethyl acetate=1:0 to 5:1) to obtain compound 10-6. $^1H$ NMR ($CDCl_3$, 400 MHz) δ 7.33-7.39 (m, 5H), 6.95 (br d, J=6.8 Hz, 4H), 5.13-5.23 (m, 2H), 3.40-3.91 (m, 4H), 3.00-3.30 (m, 2H), 2.51-2.54 (m, 1H), 0.89-0.90 (m, 1H), 0.21-0.50 (m, 1H), 0.18-0.20 (m, 1H), −0.08-0.1 (m, 1H), −0.28-0.26 (m, 1H).

Step 5: Synthesis of Compound 10-7

Pd/C (0.3 g, palladium content of 10%) and ethyl acetate (20 mL) were added into a reaction flask, and then the compound 10-6 (0.15 g, 423.23 μmol, 1 eq) was added. The reaction solution was stirred at 25° C. for 4 hours under $H_2$ (15 psi) atmosphere. The reaction solution was filtered through diatomaceous earth, and the resulting filter cake was washed with methanol (100 mL×2), and the resulting filtrate was concentrated under reduced pressure to obtain a crude product of compound 10-7, which was used directly in the next step without purification. MS m/z (ESI): 221.1 $[M+H]^+$.

Step 6: Synthesis of Compound 10

The compound 10-7 (81 mg, 367.71 μmol, 1.0 eq), the intermediate 2 (130.22 mg, 367.71 μmol, 1 eq) and dichloromethane (3 mL) were added into a reaction flask, and then a solution of triethylamine (186.04 mg, 1.84 mmol, 5 eq) and 50% tripropylphosphonic anhydride ethyl acetate (350.99 mg, 551.56 μmol, 1.5 eq) were added. The reaction solution was stirred at 25° C. for 1 hour, added with 20 ml of water and 20 mL of dichloromethane after completion of reaction, and allowed to stand for phase separation. The aqueous phase was extracted with dichloromethane (20 mL×3). The organic phases were combined and dried over anhydrous sodium sulfate, and concentrated under reduced pressure to obtain a crude product. The crude product was separated by preparative HPLC (chromatographic column: Waters Xbridge Prep OBD C18 150*40 mm*10 μm; mobile phase: [water (10 mM ammonium bicarbonate)-acetonitrile]; acetonitrile %: 55%-75%, 8 min) to obtain compound 10. $^1H$ NMR (CDCB, 400 MHz) δ 7.4-7.5 (m, 1H), 6.9-7.0 (m, 2H), 6.7-6.9 (m, 4H), 3.8-4.1 (m, 2H), 3.4-3.7 (m, 4H), 3.1-3.3 (m, 3H), 2.8-3.0 (m, 3H), 2.2-2.5 (m, 1H), 1.1-1.2 (m, 9H), 0.6-0.9 (m, 1H), −0.2-0.4 (m, 3H), −0.4–−0.2 (m, 1H). MS m/z (ESI): 486.3 $[M+H]^+$.

Example 11

Compound 11

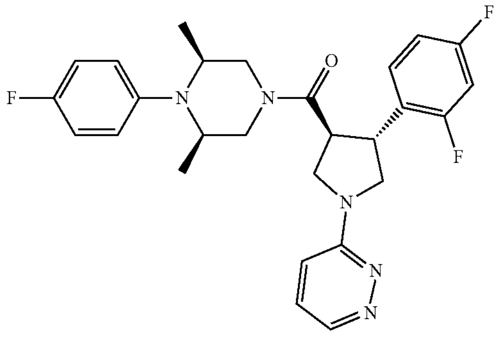

or

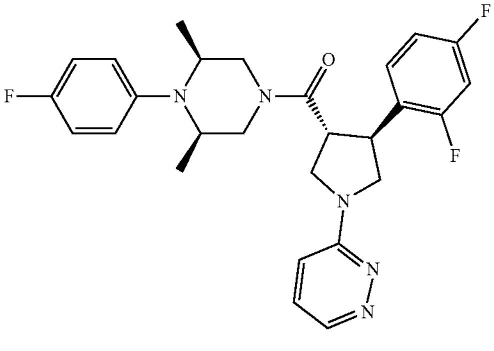

Synthetic Route:
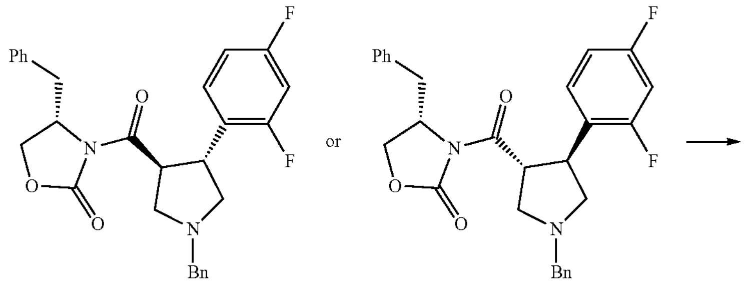
or
Compound 7-2
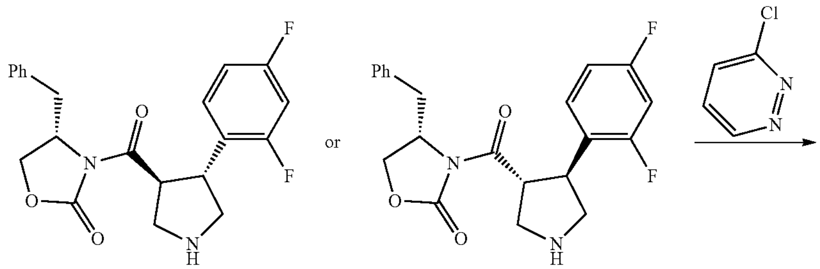
or
Compound 11-1
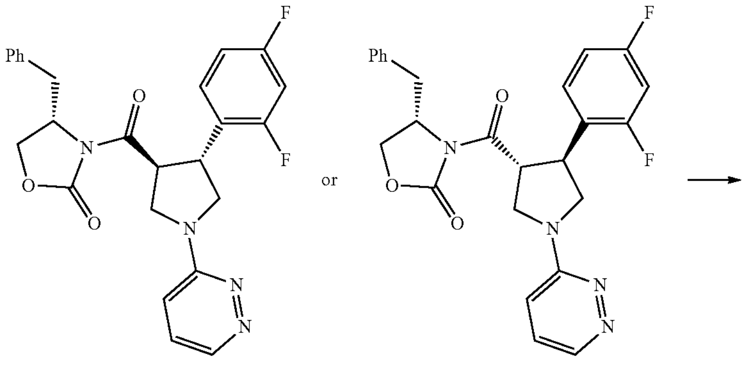
or
Compound 11-2
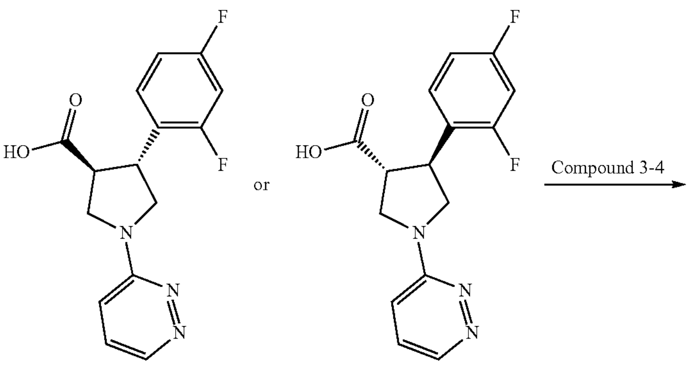
or
Compound 11-3

-continued

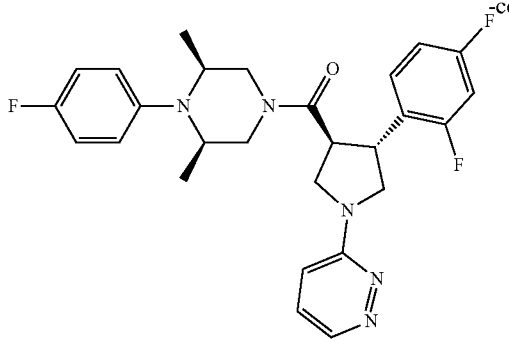

or

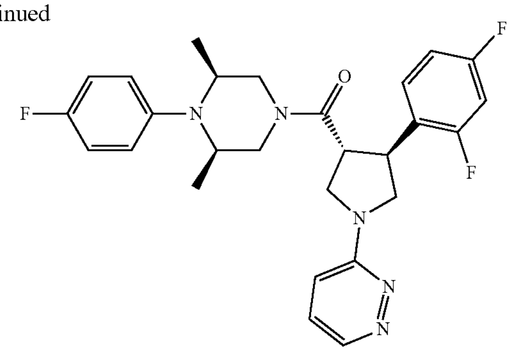

Compound 11

Step 1: Synthesis of Compound 11-1

Palladium carbon catalyst (1.0 g, palladium content of 10%) and methanol (30 mL) were added into a reaction flask, then the compound 7-2 (1.0 g, 2.10 mmol, 1 eq) and 2 mol/L hydrochloric acid (0.5 mL) were added, and stirred at 40° C. for 16 hours under the action of $H_2$ (40 PSI). The reaction solution was filtered through diatomaceous earth, the filter cake was washed with methanol (200 mL×2), and the filtrate was concentrated under reduced pressure to obtain compound 11-1. MS m/z (ESI): 387.1 $[M+H]^+$.

Step 2: Synthesis of Compound 11-2

The compound 11-1 (500 mg, 1.29 mmol, 1 eq), hydrochloride salt of 3-chloropyridazine (976.95 mg, 6.47 mmol, 5 eq) and DMSO (5 mL) were added into a reaction flask, and then N,N-diisopropylethylamine (1.00 g, 7.76 mmol, 1.35 mL, 6 eq) and cesium fluoride (196.56 mg, 1.29 mmol, 1 eq) were added. The reaction solution was stirred at 100° C. for 16 hours, and extracted with 150 mL of water and ethyl acetate (50 mL×3) after completion of reaction. The organic phases were combined and washed with 100 mL of water, then dried over anhydrous sodium sulfate, filtered and concentrated under reduced pressure to obtain a crude product. The crude product was purified by silica gel column chromatography (petroleum ether:ethyl acetate=1:0 to 0:1) to obtain compound 11-2. $^1H$ NMR ($CDCl_3$, 400 MHz) δ 8.51-8.52 (m, 1H), 7.14-7.41 (m, 5H), 7.00-7.01 (m, 2H), 6.80-6.82 (m, 2H), 6.57-6.59 (m, 1H), 4.62-4.66 (m, 2H), 4.04-4.27 (m, 5H), 3.63-3.80 (m, 2H), 3.06-3.10 (m, 1H), 2.64-2.69 (m, 1H). MS m/z (ESI): 465.2 $[M+H]^+$.

Step 3: Synthesis of Compound 11-3

The compound 11-2 (110 mg, 236.83 μmol, 1 eq) and tetrahydrofuran (4 mL) were added into a reaction flask, and then lithium hydroxide monohydrate (29.81 mg, 710.50 μmol, 3.0 eq) and $H_2O$ (2 mL) were added at 0° C. The reaction solution was stirred at 25° C. for 4 hours, then concentrated under reduced pressure, and extracted by adding water (10 mL) and ethyl acetate (10 mL×3). The aqueous phase was adjusted to a pH of about 5 with 2 N hydrochloric acid and then concentrated under reduced pressure directly to obtain compound 11-3, which was used directly in the next step without further purification. MS m/z (ESI): 306.1 $[M+H]^+$.

Step 4: Synthesis of Compound 11

The compound 3-4 (100 mg, 480.14 μmol, 1 eg), the compound 11-3 (146.58 mg, 480.14 μmol, 1.0 eq) and DCM (2 mL) were added into a reaction flask, and then triethylamine (242.92 mg, 2.40 mmol, 334.15 μL, 5 eq) and a 50% solution of tripropylphosphonic anhydride in ethyl acetate (458.31 mg, 720.20 μmol, 1.5 eq) were added. The reaction solution was stirred at 25° C. for 2 hours, then added with 20 mL water and 20 mL dichloromethane, and allowed to stand for phase separation. Then the aqueous phase was extracted with dichloromethane (20 mL×3). The organic phases were combined and dried over anhydrous sodium sulfate, and concentrated under reduced pressure to obtain a crude product. The crude product was separated and purified by preparative HPLC (chromatographic column: Waters Xbridge Prep OBD C18 150*40 mm*10 μm; mobile phase: [water (10 mM ammonium bicarbonate)-acetonitrile]; acetonitrile %: 35%-65%, 8 min) to obtain compound 11. $^1H$ NMR ($CDCl_3$, 400 MHz) δ 8.59-8.61 (m, 1H), 7.21-7.26 (m, 2H), 7.00-7.02 (m, 1H), 6.95-6.98 (m, 5H), 6.68-6.69 (m, 1H), 4.54-4.57 (m, 1H), 4.05-4.13 (m, 3H), 3.69-3.90 (m, 4H), 2.90-2.98 (m, 2H), 2.17-2.7 (m, 1H), 2.42-2.60 (m, 1H), 0.65-0.77 (m, 6H). MS m/z (ESI): 496.3 $[M+H]^+$.

Example 12

Compound 12

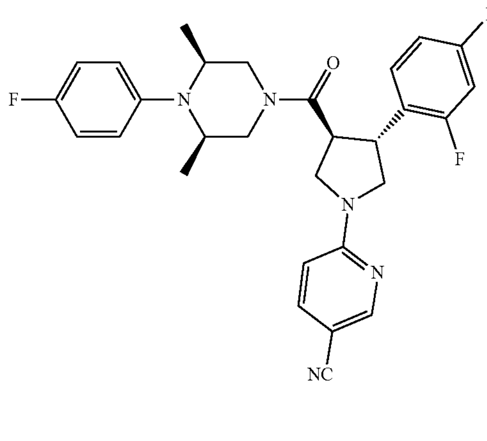

or

-continued
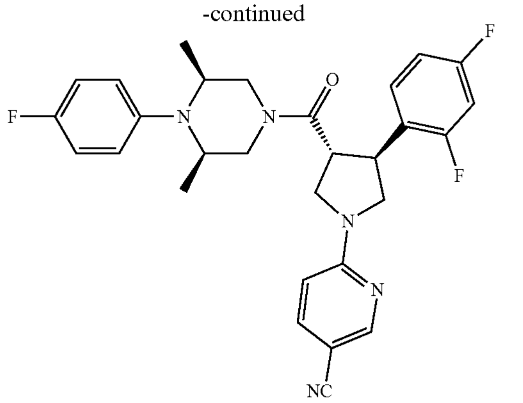
Synthetic Route:
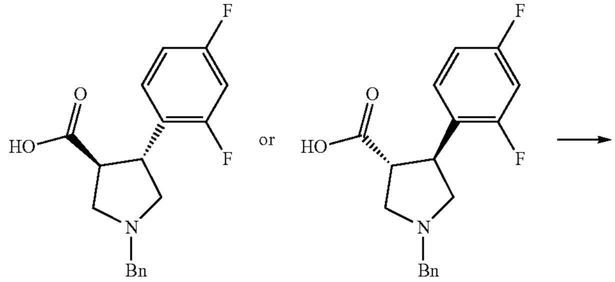
Compound 7-3
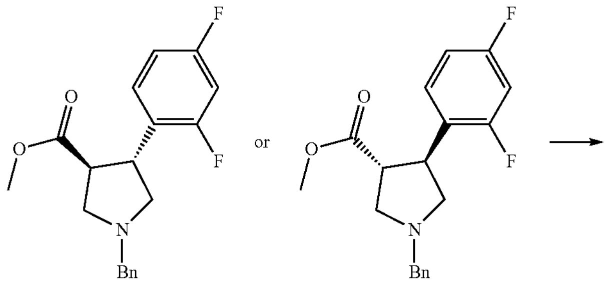
Compound 12-1
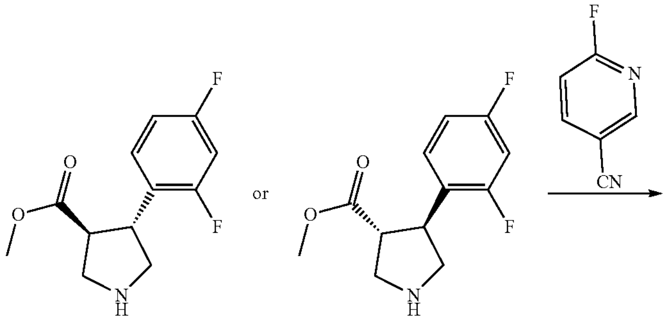
Compound 12-2

-continued

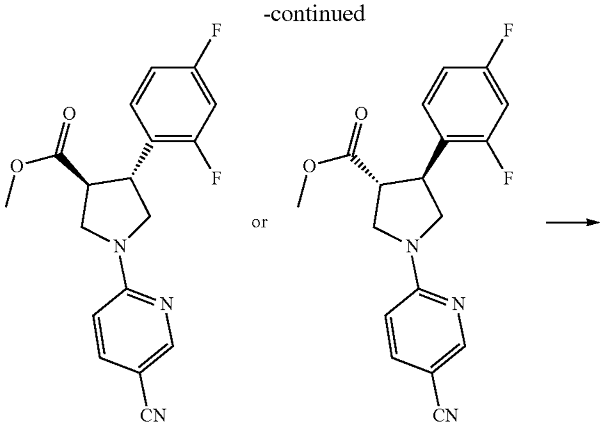

or

Compound 12-3

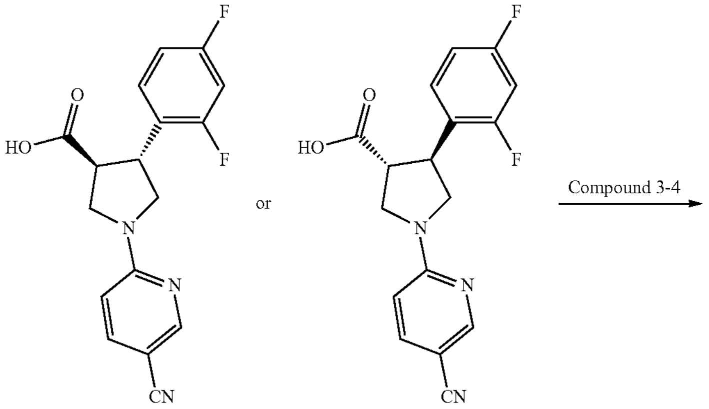

or

Compound 12-4

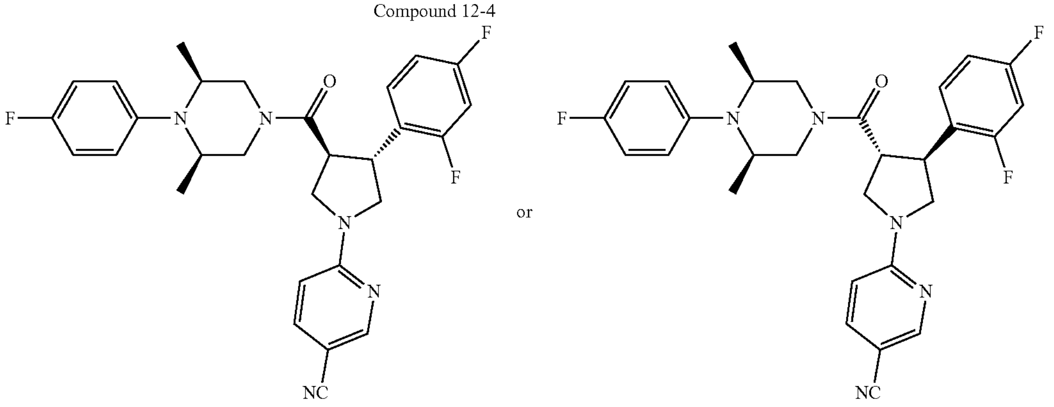

or

Compound 12

Step 1: Synthesis of Compound 12-1

The compound 7-3 (1.2 g, 3.78 mmol, 1 eq), toluene (9 mL) and methanol (1 mL) were added into a reaction flask, and the solution was added with trimethylsilyldiazomethane (2 M, 5.67 mL, 3 eq) dropwise. The reaction solution was stirred at 25° C. for 1 hour, added with glacial acetic acid dropwise until colorless, and directly concentrated under reduced pressure. Then the reaction solution was extracted by adding water (20 mL) and dichloromethane (10 mL×3). The organic phase was collected and concentrated under reduced pressure to obtain a crude acetate product of compound 12-1, which was used directly in the next step without further purification. MS m/z (ESI): 332.1 $[M+H]^+$.

Step 2: Synthesis of Compound 12-2

The acetate of the compound 12-1 (0.61 g, 1.56 mmol, 1 eq) and Pd/C catalyst (1 g, palladium content of 10%) were added into a reaction flask, and then methanol (10 mL) and ethyl acetate (10 mL) were added. The reaction was conducted under stirring at 40° C. for 4 hours under $H_2$ (40 psi) atmosphere. The reaction solution was filtered through diatomaceous earth, the filter cake was washed with methanol (200 mL×2), and the filtrate was concentrated under reduced pressure to obtain a crude product of compound 12-2. MS m/z (ESI): 242.0 $[M+H]^+$.

Step 3: Synthesis of Compound 12-3

The compound 12-2 (80 mg, 265.53 μmol, 1 eq) and hydrochloride salt of 2-fluoro-5-cyanopyridine (126.40 mg, 1.04 mmol, 5 eq) were added into a reaction flask, then toluene (1 mL) and N,N-diisopropylethylamine (1 mL) were added, and stirred in microwave at 80° C. for 1 hour. The reaction solution was concentrated under reduced pressure and then extracted by adding water (20 mL) and dichloromethane (10 mL×3). The organic phases were combined, concentrated under reduced pressure to obtain a crude product, which was purified through by silica gel column chromatography (petroleum ether:ethyl acetate=10:0 to 2:1) to obtain compound 12-3, MS m/z (ESI): 344.1 $[M+H]^+$.

Step 4: Synthesis of Compound 12-4

The compound 12-3 (113 mg, 329.13 μmol, 1 eq) and tetrahydrofuran (3 mL) were added into a reaction flask, and then lithium hydroxide monohydrate (41.43 mg, 987.40 μmol, 3.0 eq) and $H_2O$ (1.5 mL) were added. The reaction solution was stirred at 25° C. for 4 hours, and then extracted by adding 10 mL of water and dichloromethane (10 mL×3). The organic phase was discarded, and the aqueous phase was adjusted to a pH of 2 with 2 M dilute hydrochloric acid, and concentrated under reduced pressure. The obtained solid was extracted with a mixed solvent of dichloromethane and methanol (10:1, 10 mL×3), and filtered. The filtrate was collected and spin-dried under reduced pressure to obtain a crude product of compound 12-4, which was used directly in the next step without further purification. $^1H$ NMR (400 MHz, DMSO-d6) δ 8.52-8.48 (m, 1H), 7.85 (dd, J=2.1, 9.0 Hz, 1H), 7.57-7.50 (m, 1H), 7.28-7.21 (m, 1H), 7.13-7.07 (m, 1H), 6.64 (br d, J=9.1 Hz, 1H), 4.07-3.61 (m, 6H). MS m/z (ESI): 330.1 $[M+H]^+$.

Step 5: Synthesis of Compound 12

The compound 12-4 (80 mg, 242.94 μmol, 1 eq), the compound 3-4 (83.94 mg, 291.53 μmol, 1.2 eq) and dichloromethane (1 mL) were added into a reaction flask, then triethylamine (122.92 mg, 1.21 mmol, 169.07 μL, 5 eq) and a 50% solution of tri-n-propylphosphonic anhydride in ethyl acetate (231.90 mg, 364.41 μmol, 1.5 eq) were added, and stirred at 25° C. for 16 hours. The reaction solution was concentrated under reduced pressure, and the obtained crude product was separated and purified by preparative HPLC (chromatographic column: Waters Xbridge Prep OBD C18 150*40 mm*10 μm; mobile phase: [water (10 mM ammonium bicarbonate)-acetonitrile]; acetonitrile %: 50%-80%, 8 min) to obtain compound 12. $^1H$ NMR (400 MHz, DMSO-d6) δ 8.54-8.48 (m, 1H), 7.90-7.84 (m, 1H), 7.67-7.45 (m, 1H), 7.40-7.21 (m, 1H), 7.20-7.06 (m, 4H), 7.04-6.97 (m, 1H), 6.70-6.61 (m, 1H), 4.31-4.14 (m, 1H), 4.12-3.92 (m, 4H), 3.89-3.78 (m, 1H), 3.67-3.43 (m, 2H), 3.04-2.82 (m, 2H), 2.64-2.55 (m, 2H), 0.68-0.50 (m, 6H). MS m/z (ESI): 520.3 $[M+H]^+$.

Example 13

Compound 13

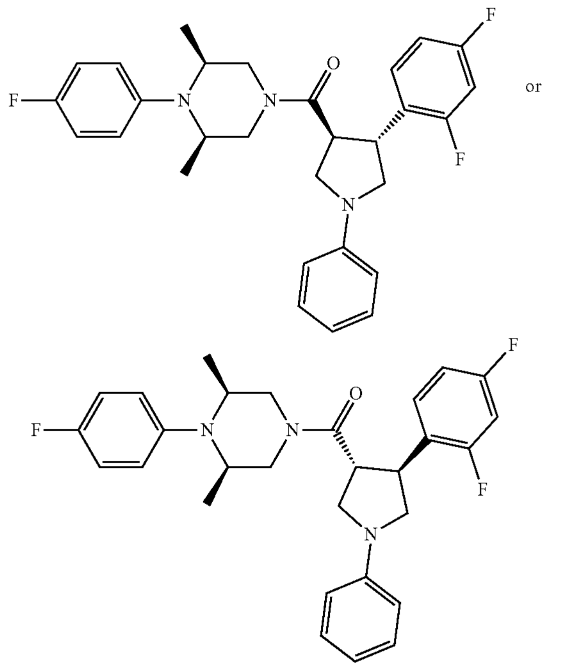

or

Synthetic Route:

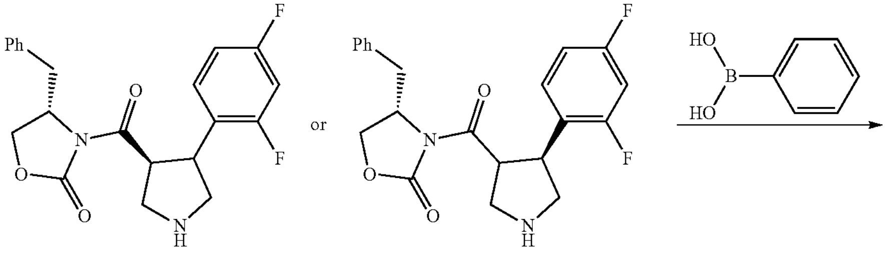

or

Compound 11-1

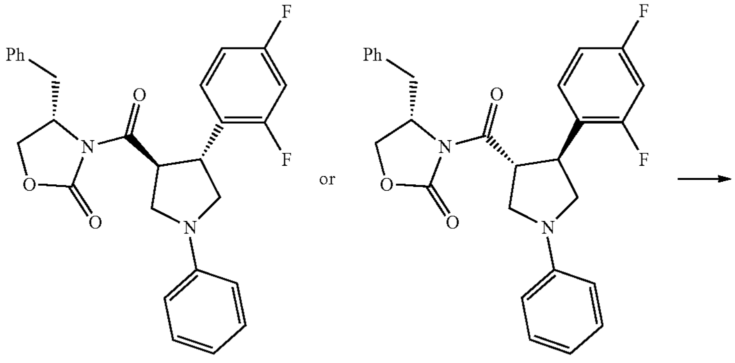

or

Compound 13-1

-continued

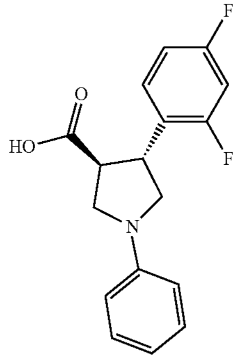

or

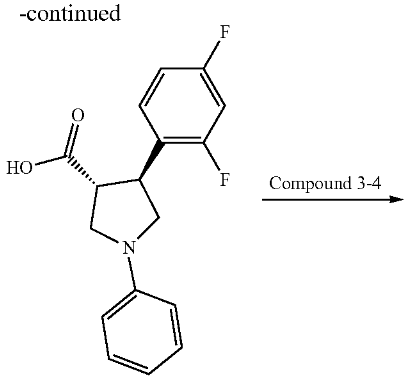

Compound 13-2

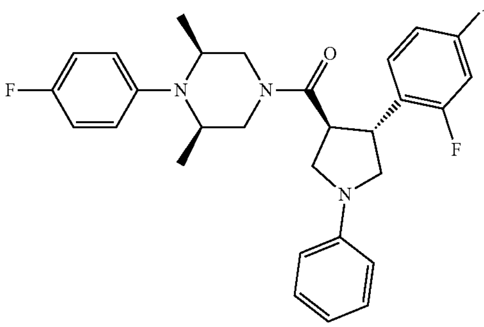

or

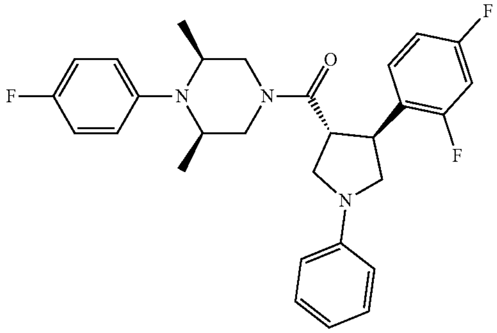

Compound 13

Step 1: Synthesis of Compound 13-1

Dichloromethane (20 mL) was added into a reaction flask, and then the compound 11-1 (600 mg, 1.55 mmol, 1 eq), phenylboronic acid (378.67 mg, 3.11 mmol, 2 eq), Cu(OAc) 2 (564.08 mg, 3.11 mmol, 2 eq) and triethylamine (1.26 g, 12.42 mmol, 1.73 mL, 8 eq) were added sequentially. The reaction solution was stirred at 25° C. for 6 hours, filtered, and extracted with dichloromethane (20 mL×3). The organic phases were combined and dried over anhydrous sodium sulfate and concentrated to obtain a crude product. The crude product was purified by flash silica gel column chromatography (petroleum ether:ethyl acetate=1:0 to 10:1) to obtain compound 13-1. MS m/z (ESI): 463.2 $[M+H]^+$.

Step 2: Synthesis of Compound 13-2

Tetrahydrofuran (1 mL) and $H_2O$ (0.5 mL) was added into a reaction flask, then the compound 13-1 (93 mg, 201.09 μmol, 1 eq) and lithium hydroxide monohydrate (25.31 mg, 603.26 μmol, 3 eq) were added sequentially, and then stirred at 25° C. for 2 hours. The reaction solution was concentrated under reduced pressure, and extracted by adding ethyl acetate (6 mL×3). Then the organic phase was discarded, and the aqueous phase was adjusted to a pH of about 5 with 2 mol/L hydrochloric acid and concentrated to dryness to obtain a hydrochloride salt of compound 13-2, which was used directly in the next step without further purification. MS m/z (ESI): 304.2 $[M+H]^+$.

Step 3: Synthesis of Compound 13

Dichloromethane (5 mL) was added into a reaction flask, and then added with the hydrochloride salt of the compound 13-2 (53 mg, 174.74 μmol), the compound 3-4 (53.46 mg, 205.33 μmol, 1.18 eq), triethylamine (88.41 mg, 873.71 μmol, 121.61 μL, 5 eg) and a 50% solution of tri-n-propylphosphonic anhydride in ethyl acetate (166.80 mg, 262.11 μmol, 1.5 eq) were added. The reaction was conducted under stirring at 25° C. for 16 hours. The reaction solution was extracted by adding 10 mL of water and 10 mL of dichloromethane. The organic phases were combined, dried over anhydrous sodium sulfate, and concentrated under reduced pressure to obtain a crude product. The crude product was separated and purified by HPLC (chromatographic column: Phenomenex C18 80*40 mm*3 μm; mobile phase: [water (10 mM ammonium bicarbonate)-acetonitrile]; acetonitrile %: 40%-70%, 8 min) to obtain compound 13. $^1H$ NMR (400 MHz, $CDCl_3$) δ 7.38-7.24 (m, 3H), 7.08-6.75 (m, 7H), 6.62-6.59 (m, 2H), 4.58-4.51 (m, 1H), 4.25-4.09 (m, 1H), 3.81-3.61 (m, 6H), 3.05-2.81 (m, 2H), 2.62-2.15 (m, 2H), 0.81-0.61 (m, 6H). MS m/z (ESI): 494.3 $[M+H]^+$.

Example 14

Compound 14

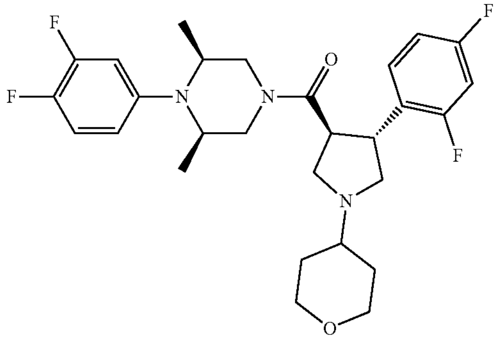

or

-continued

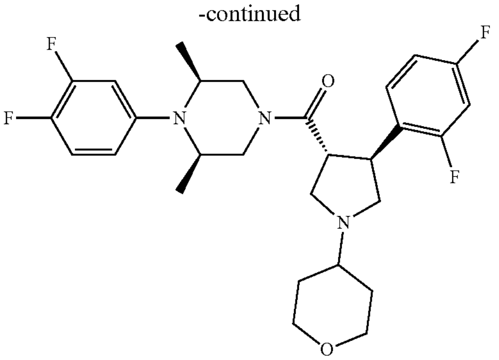

Synthetic Route:

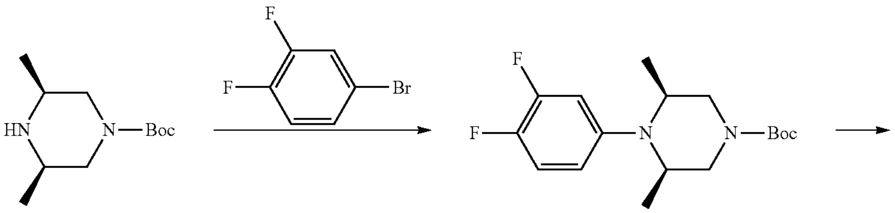

Compound 1-1

Compound 14-1

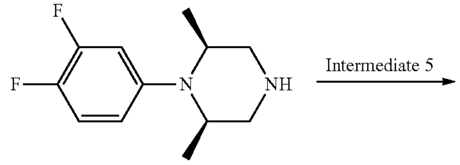

Compound 14-2

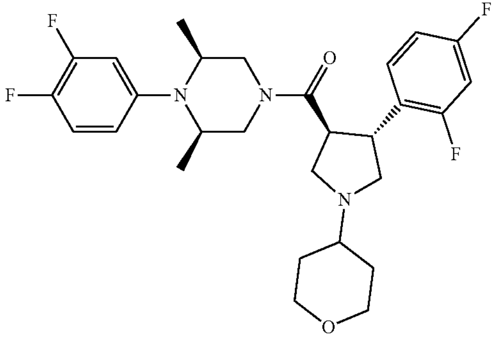

or

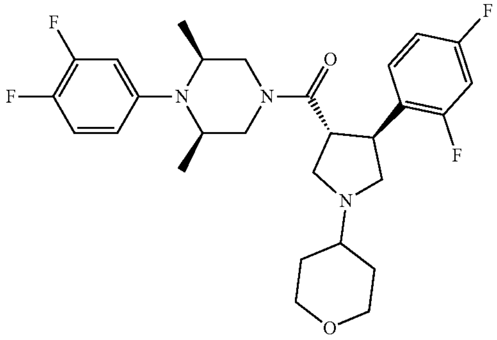

Compound 14

Step 1: Synthesis of Compound 14-1

The compound 1-1 (0.5 g, 2.33 mmol, 1 eq), 4-bromo-1,2-difluorobenzene (540.32 mg, 2.80 mmol, 1.2 eq) and tetrahydrofuran (10 mL) were added into a reaction flask, and then added with KHMDS solution (1 M, 2.80 mL, 1.2 eq) slowly at 0° C. under nitrogen atmosphere. The reaction solution was slowly heated to 25° C. and stirred continuously for 4 hours. The reaction solution was spun to dryness under reduced pressure, and extracted by adding 30 mL of water and dichloromethane (20 mL×3). The organic phases were combined and dried over anhydrous sodium sulfate, concentrated under reduced pressure to obtain a crude product, which was separated and purified by silica gel column chromatography (petroleum ether:ethyl acetate=100:1-20:1) to obtain compound 14-1. MS m/z (ESI): 327.2 $[M+H]^+$.

Step 2: Synthesis of Compound 14-2

The compound 14-1 (750 mg, 2.30 mmol, 1 eq) and dichloromethane (3 mL) were added into a reaction flask, then a solution of hydrogen chloride in ethyl acetate (4 M, 11.49 mL, 20 eq) was added at 0° C. The reaction solution was stirred at 25° C. for 4 hours. The reaction solution was concentrated under reduced pressure to obtain a hydrochloride salt of compound 14-2, which was used directly in the next step without further purification. $^1H$ NMR (400 MHz, DMSO-d6) δ 9.71-9.21 (m, 1H), 7.52-7.36 (m, 1H), 7.34-7.16 (m, 1H), 7.14-6.94 (m, 1H), 3.49-2.65 (m, 6H), 0.89-0.53 (m, 6H). MS m/z (ESI): 227.1 $[M+H]^+$.

Step 3: Synthesis of Compound 14

The hydrochloride salt of the compound 14-2 (150 mg, 448.09 μmol, 1 eq), the intermediate 5 (220.73 mg, 537.71 μmol, 1.2 eq), triethylamine (226.71 mg, 2.24 mmol, 311.84 μL, 5 eq), a 50% solution of tripropylphosphonic anhydride in ethyl acetate (427.72 mg, 672.13 μmol, 1.5 eq) and dichloromethane (4 mL) were added into a reaction flask, and then stirred at 25° C. for 1 hour. The reaction solution was concentrated under reduced pressure, and the crude product was separated and purified by preparative HPLC (chromatographic column: Waters Xbridge Prep OBD C18 150*40 mm*10 μm; mobile phase: [water (10 mM ammonium bicarbonate)-acetonitrile]; acetonitrile %: 40%-75%, 8 min) to obtain compound 14. $^1H$ NMR (400 MHz, DMSO-d6) δ 7.64-7.51 (m, 1H), 7.37-7.26 (m, 1H), 7.23-7.02 (m, 3H), 6.83 (br d, J=4.5 Hz, 1H), 4.06-3.97 (m, 1H), 3.95-3.79 (m, 3H), 3.69-3.61 (m, 1H), 3.54-3.39 (m, 1H), 3.32-3.25 (m, 2H), 3.23-3.04 (m, 3H), 3.03-2.89 (m, 2H), 2.83-2.58 (m, 3H), 2.34-2.27 (m, 1H), 1.77 (br s, 2H), 1.47-1.32 (m, 2H), 0.72 (dd, J=4.6, 5.6 Hz, 3H), 0.64 (dd, J=6.1, 12.6 Hz, 3H). MS m/z (ESI): 520.3 $[M+H]^+$.

Example 15
Compound 15
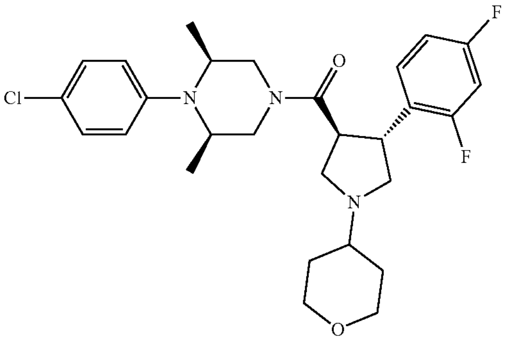
or
-continued
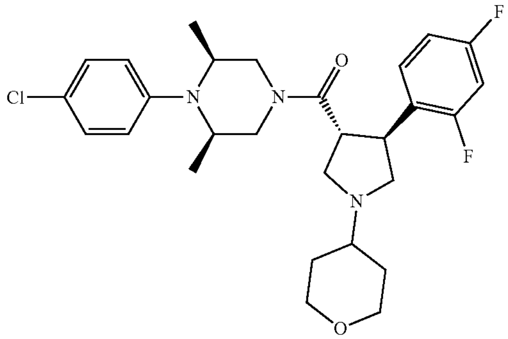
Synthetic Route:
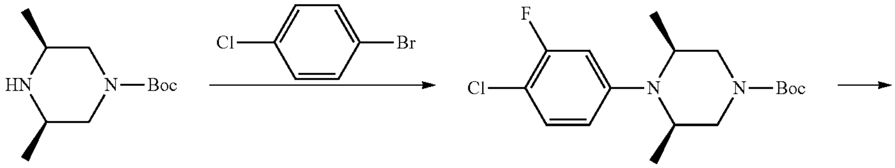
Compound 1-1
Compound 15-1
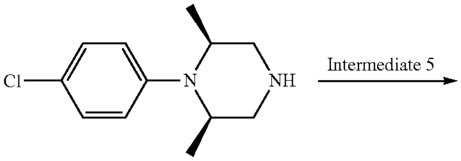
Compound 15-2
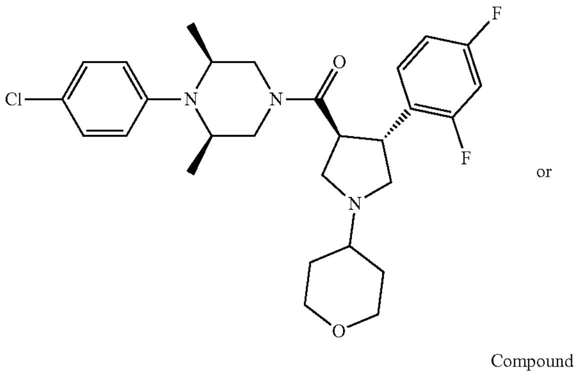
or
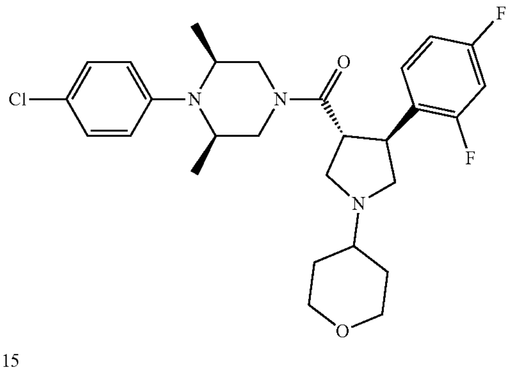
Compound 15

Step 1: Synthesis of Compound 15-1

The compound 1-1, p-chlorobromobenzene (1.34 g, 5.60 mmol, 1.2 eq), sodium tert-butoxide (896.86 mg, 9.33 mmol, 2 eq) and toluene (10 mL) were added into a reaction flask, and bis(tri-tert-butylphosphine) palladium (476.94 mg, 933.26 μmol, 0.2 eq) was added under nitrogen atmosphere, and reaction was conducted under stirring at 110° C. for 20 hours. After cooled to room temperature, the reaction solution was filtered through diatomaceous earth, the filter cake was washed with ethyl acetate, and the filtrate was concentrated under reduced pressure. The crude product was separated and purified by flash silica gel column chromatography (petroleum ether:ethyl acetate=1:0-9:1) to obtain compound 15-1. MS m/z (ESI): 325.2 $[M+H]^+$.

Step 2: Synthesis of Compound 15-2

The compound 15-1 (255 mg, 400.35 μmol) and dichloromethane (5 mL) were added into a reaction flask, and stirred for dissolution. After cooled to 0° C., the solution was added with a solution of hydrogen chloride in ethyl acetate (4 M, 5 mL), and the reaction was conducted under stirring at 20° C. for 1 hour. The reaction solution was concentrated under reduced pressure to obtain a hydrochloride salt of compound 15-2. MS m/z (ESI): 225.1 $[M+H]^+$.

Step 3: Synthesis of Compound 15

The intermediate 5 (166.62 mg, 497.72 μmol), the hydrochloride salt of the compound 15-2 (200 mg, 497.72 μmol, 1 eq), dichloromethane (2 mL) were added into a reaction flask, and finally triethylamine (151.09 mg, 1.49 mmol, 3 eq) and a 50% solution of tripropylphosphonic anhydride in ethyl acetate (475.10 mg, 746.58 μmol, 1.5 eq) was added, stirred and reacted at 20° C. for 12 hours, and then added with 10 mL of water. The aqueous phase was extracted with (5 mL×3) dichloromethane for 3 times. The organic phases were combined, dried and concentrated under reduced pressure to obtain a crude product, which was then purified by preparative HPLC (chromatographic column: Waters Xbridge BEH C18 100*30 mm*10 μm; organic phase: [water (10 mM ammonium bicarbonate)-acetonitrile]; acetonitrile %: 40%-60%, 8 min) to obtain compound 15. $^1H$ NMR (400 MHz, $CDCl_3$) δ ppm 7.43-7.53 (m, 1H), 7.28 (s, 1H), 6.98 (dd, J=16.0, 8.4 Hz, 2H), 6.75-6.91 (m, 2H), 4.39-4.49 (m, 1H), 3.91-4.01 (m, 3H), 2.80-3.59 (m, 12H), 2.44-2.73 (m, 3H), 1.83 (br d, J=11.6 Hz, 2H), 1.26-1.29 (m, 1H), 0.72-0.77 (m, 3H), 0.53-0.68 (m, 3H). MS m/z (ESI): 518.3 $[M+H]^+$.

Example 16

Compound 16

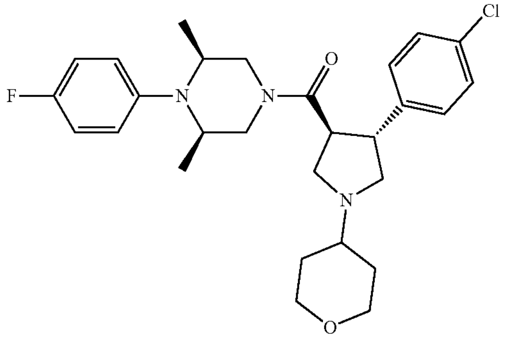

or

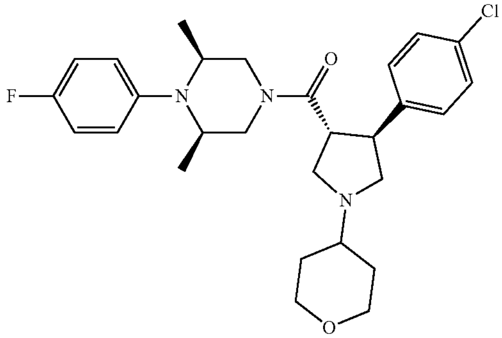

Synthetic Route:

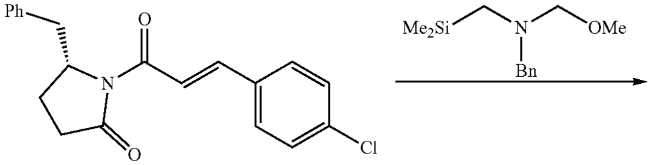

Intermediate 4-2

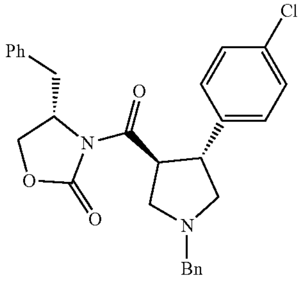

or

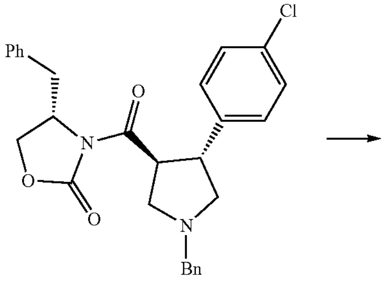

Compound 16-1

-continued

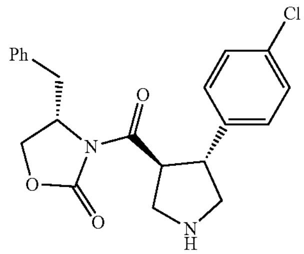

or

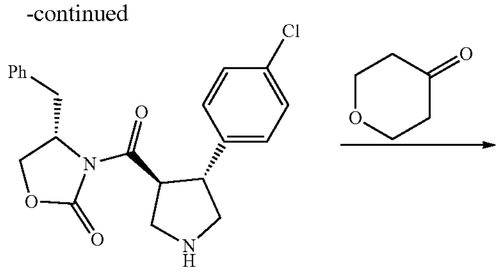

Compound 16-2

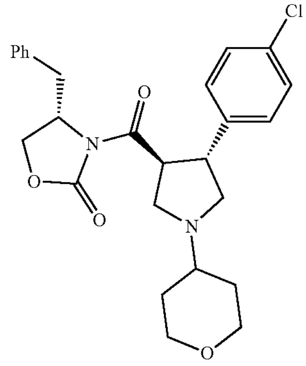

or

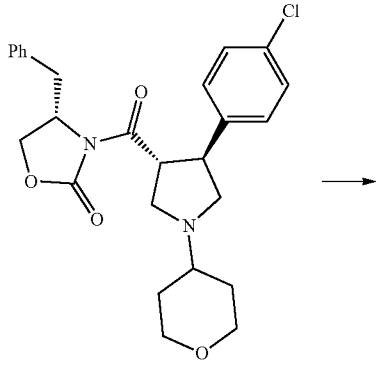

Compound 16-3

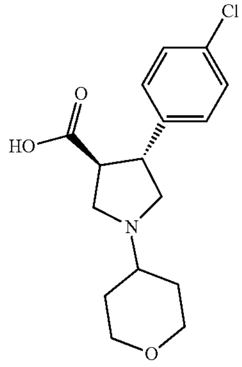

or

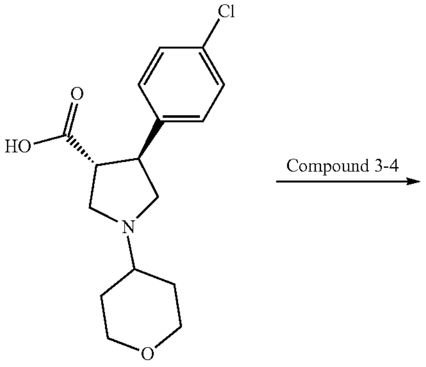

Compound 16-4

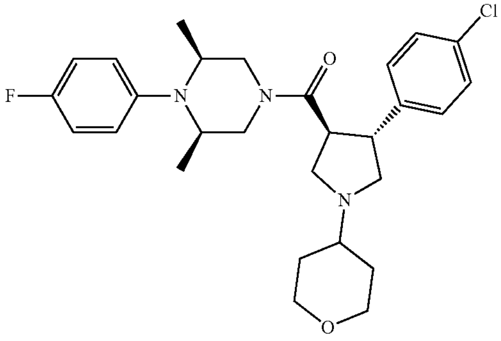

or

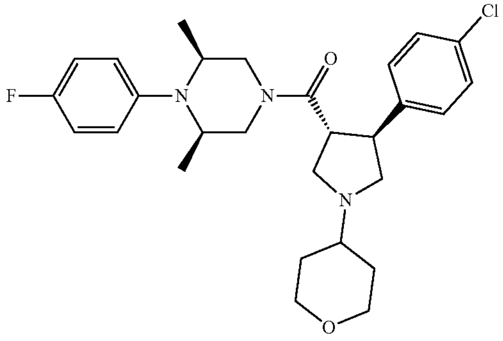

Compound 16

Step 1: Synthesis of Compound 16-1

The intermediate 4-2 (1.6 g, 4.68 mmol, 1 eq), N-methoxymethyl-N-(trimethylsilylmethyl)benzylamine (1.67 g, 7.02 mmol, 1.5 eq) and dichloromethane (16 mL) were added into a reaction flask, and then trifluoroacetic acid (266.88 mg, 2.34 mmol, 173.30 μL, 0.5 eq) was added slowly dropwise at 25° C. After the dropwise addition, the reaction solution was stirred at 25° C. for 16 hours. The reaction solution was poured into a saturated aqueous solution of sodium bicarbonate (20 mL) and stirred for 10 minutes, and allowed to 10 stand for phase separation. The aqueous phase was extracted with dichloromethane (100 mL×3). The organic phases were combined and dried over anhydrous sodium sulfate, and concentrated under reduced pressure to obtain a crude product. The crude product was separated and purified by flash column chromatography (petroleum ether:ethyl acetate=1:0-5:1) to obtain compound 16-1. $^1H$ NMR (400 MHz, $CDCl_3$) δ 7.29-7.32 (m, 5H), 7.21-7.27 (m, 7H), 7.04-7.25 (m, 2H), 4.64-4.66 (m, 1H), 4.01-4.22 (m, 4H), 3.60-3.73 (m, 2H), 3.12-3.20 (m, 3H), 2.66-2.75 (m, 3H). MS m/z (ESI): 475.2 $[M+H]^+$.

Step 2: Synthesis of Compound 16-2

Pd/C catalyst (0.3 g, palladium content of 10%) and ethyl acetate (15 mL) were added into a reaction flask, and then the compound 16-1 (500 mg, 1.05 mmol, 1 eq) and zinc bromide (237.06 mg, 1.05 mmol, 52.68 μL, 1 eq) were added. The reaction solution was stirred at 40° C. for 16 hours under $H_2$ (15 Psi) atmosphere. The reaction solution was filtered through diatomaceous earth, and the filter cake was washed with methanol (200 mL×2), and the filtrate was concentrated under reduced pressure to obtain a crude product of compound 16-2, which was used directly in the next step without purification. MS m/z (ESI): 385.1 $[M+H]^+$.

Step 3: Synthesis of Compound 16-3

The compound 16-2 (0.4 g, 1.04 mmol, 1 eq), tetrahydropyran-4-one (208.11 mg, 2.08 mmol, 190.93 μL, 2 eq), triethylamine (210.34 mg, 2.08 mmol, 289.33 μL, 2 eq), dichloromethane (10 mL) and acetic acid (0.1 mL) were added into a reaction flask. The reaction solution was stirred at 25° C. for 2 hours, and then added with NaBH(OAc) 3 (330.42 mg, 1.56 mmol, 1.5 eq). The reaction solution was stirred continuously at 25° C. for 16 hours, then added with 10 mL of a saturated aqueous solution of sodium bicarbonate, and extracted with dichloromethane (30 mL×3). The organic phases were combined, dried over anhydrous sodium sulfate and concentrated under reduced pressure to obtain a crude product. The crude product was separated by flash column chromatography (dichloromethane:methanol=1:0 to 10:1) to obtain compound 16-3. $^1H$ NMR (400 MHz, $CDCl_3$) δ 7.20-7.31 (m, 7H), 7.02-7.05 (m, 2H), 4.70-4.72 (m, 1H), 4.14-4.24 (m, 3H), 3.97-4.01 (m, 3H), 3.30-3.41 (m, 2H), 3.23-3.25 (m, 3H), 2.80-2.89 (m, 1H), 2.69-2.78 (m, 2H), 2.38-2.44 (m, 1H), 1.78-1.81 (m, 2H), 1.61-1.75 (m, 2H). MS m/z (ESI): 469.2 $[M+H]^+$.

Step 4: Synthesis of Compound 16-4

The compound 16-3 (96 mg, 204.70 μmol, 1 eq) and tetrahydrofuran (4 mL) were added into a reaction flask, and then lithium hydroxide monohydrate (25.77 mg, 614.11 μmol, 3.0 eq) and water (2 mL) were added at 0° C. The reaction solution was stirred at 25° C. for 16 hours. The reaction solution was directly concentrated under reduced pressure, and then extracted by adding water (10 mL) and ethyl acetate (10 mL×3). The aqueous phase was adjusted to a pH of about 2 with 2 N hydrochloric acid and then concentrated under reduced pressure to obtain a crude product of compound 16-4, which was used directly in the next step without further purification. MS m/z (ESI): 310.1 $[M+H]^+$.

Step 5: Synthesis of Compound 16

The compound 16-4 (63 mg, 203.37 μmol, 1.0 eq), the hydrochloride salt of the compound 3-4 (68.62 mg, 244.04 μmol, 1.2 eq) and dichloromethane (5 mL) were added into a reaction flask, and then triethylamine (102.89 mg, 1.02 mmol, 141.53 μL, 5 eq) and a 50% solution of tripropylphosphonic anhydride in ethyl acetate (194.12 mg, 305.05 μmol, 1.5 eq) were added. The reaction solution was stirred at 25° C. for 1 hour, then added with 20 mL of water and 20 mL of dichloromethane, and allowed to stand for phase separation. The aqueous phase was extracted with dichloromethane (100 mL×3). The organic phases were combined and dried over anhydrous sodium sulfate, and concentrated under reduced pressure to obtain a crude product, which was separated and purified by preparative HPLC (chromatographic column: Waters Xbridge Prep OBD C18 150*40 mm*10 μm; mobile phase: [water (10 mM ammonium bicarbonate)-acetonitrile]; acetonitrile %: 40%-75%, 8 min) to obtain compound 16. $^1H$ NMR (400 MHz, DMSO-d6) δ 7.20-7.28 (m, 4H), 6.88-6.92 (m, 4H), 4.44-4.50 (m, 1H), 3.93 (br s, 2H), 3.59-3.80 (m, 1H), 3.32-3.50 (m, 3H), 3.00-3.28 (m, 2H), 2.50-2.85 (m, 5H), 2.35-2.41 (m, 2H), 1.92-2.19 (m, 1H), 1.65-1.82 (m, 2H), 1.52-1.60 (m, 1H), 1.45-1.48 (m, 1H), 0.56-0.65 (m, 4H), 0.39 (d, J=6.0 Hz, 2H). MS m/z (ESI): 500.3 $[M+H]^+$.

Example 17

Compound 17

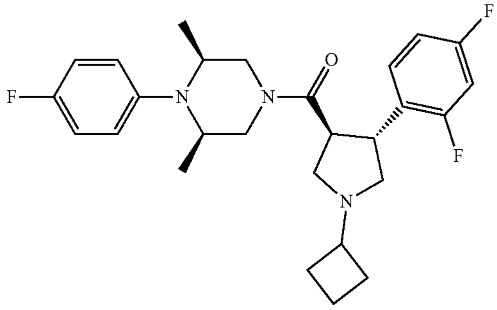

or

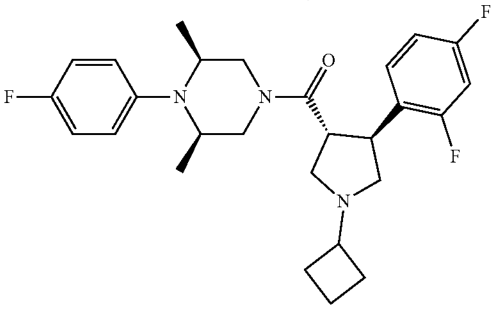

Synthetic Route:

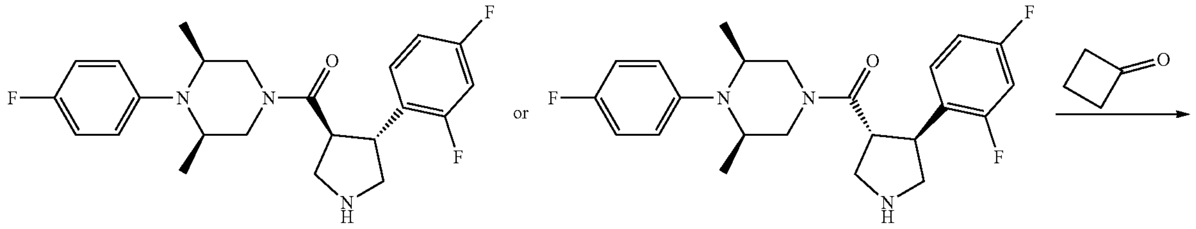

Compound 7-5

-continued

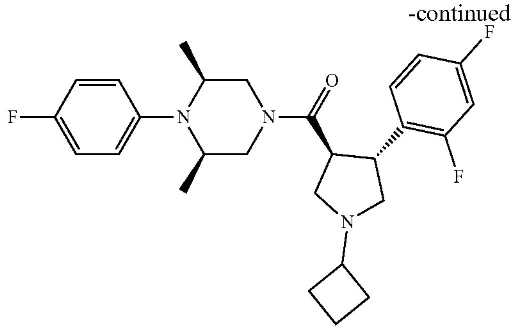

or

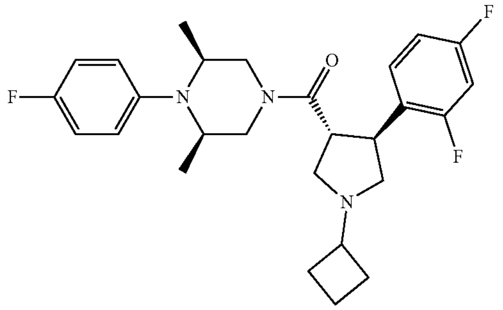

Compound 17

Step 1: Synthesis of Compound 17

The compound 7-5 (300 mg), cyclobutanone (90.66 mg, 1.29 mmol, 96.65 μL), dichloromethane (10 mL) and acetic acid (0.3 mL) were added into a reaction flask, stirred for 2 hours, then added with NaBH(OAc) 3 (205.61 mg, 970.14 μmol), maintained at 20° C. and stirred for 10 hours. Then the reaction solution was added with 10 mL of dichloromethane and mL of water. The aqueous phase was extracted twice with dichloromethane (10 mL×2). The organic phases were combined, dried over anhydrous sodium sulfate and concentrated under reduced pressure, and separated and purified by preparative HPLC (chromatographic 10 column: Waters Xbridge BEH C18 100*30 mm*10 μm; mobile phase: [water (10 mM ammonium bicarbonate)-acetonitrile]; acetonitrile %: 50%-80%, 8 min) to obtain compound 17. $^1H$ NMR (400 MHz, $CDCl_3$, 298 K) δ (ppm)=7.55-7.40 (m, 1H), 7.11-6.94 (m, 4H), 6.92-6.69 (m, 2H), 4.63-4.48 (m, 1H), 4.10-3.92 (m, 1H), 3.65-3.50 (m, 1H), 3.44-3.28 (m, 1H), 3.16-2.68 (m, 8H), 2.58-2.42 (m, 1H), 2.10-1.92 (m, 4H), 1.84-1.66 (m, 2H), 0.76-0.68 (m, 3H), 0.67-0.48 (m, 3H). MS m/z (ESI): 472.1 $[M+H]^+$.

Compound 18

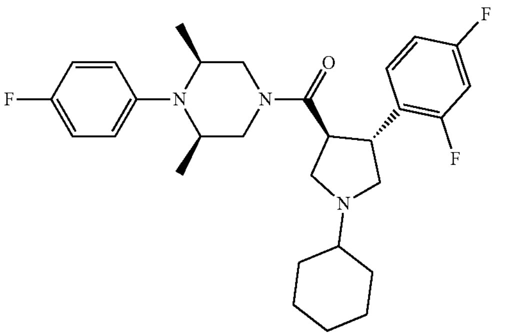

or

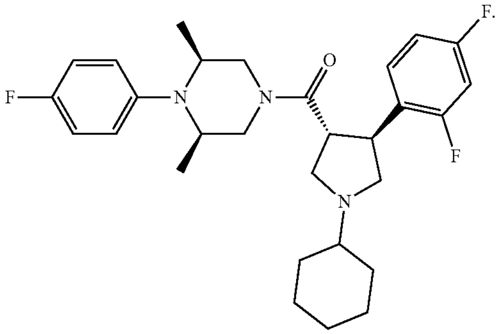

Synthetic Route:

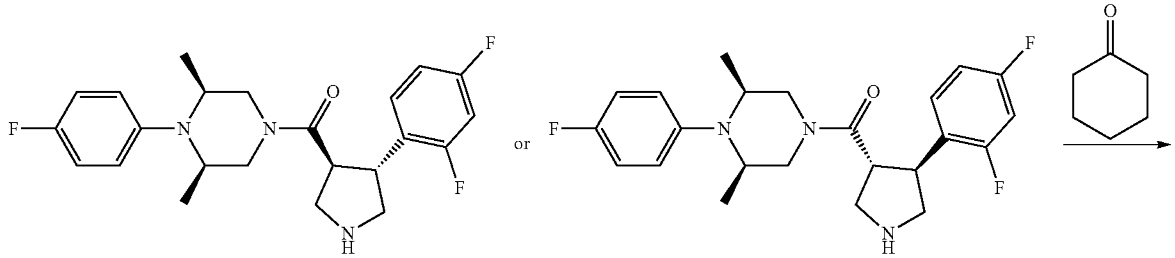

or

Compound 7-5

-continued

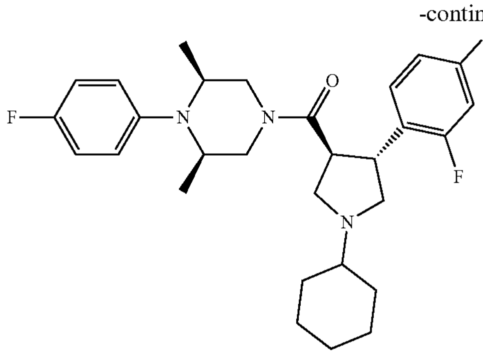

or

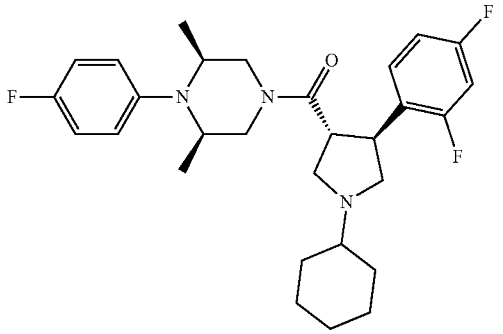

Compound 18

Step 1: Synthesis of Compound 18

The compound 7-5 (100 mg) and cyclohexanone (42.32 mg, 431.17 μmol, 44.68 μL) were dissolved in dichloromethane (10 mL), then acetic acid (0.3 mL) was added and stirred for 2 hours, and then added with NaBH(OAc); (68.54 mg, 323.38 μmol), kept at 20° C. and stirred continuously for 10 hours. The reaction solution was extracted and separated by adding 10 mL of dichloromethane and 10 mL of water. The aqueous phase was extracted twice with dichloromethane (10 mL×2). The organic phases were combined, dried over anhydrous sodium sulfate, concentrated under reduced pressure, and separated and purified by preparative HPLC (chromatographic column: Phenomenex C18 80*40 mm*3 μm; mobile phase: [water (10 mM ammonium bicarbonate)-acetonitrile]; acetonitrile %: 40%-75%, 8 min) to obtain compound 18. $^1$H NMR (400 MHz, $CDCl_3$, 298 K) δ (ppm)=7.58-7.40 (m, 1H), 7.09-6.96 (m, 4H), 6.93-6.70 (m, 2H), 4.61-4.47 (m, 1H), 4.10-3.91 (m, 1H), 3.67-3.52 (m, 1H), 3.46-2.18 (m, 10H), 2.01-1.65 (m, 5H), 1.38-1.15 (m, 5H), 0.75-0.68 (m, 3H), 0.67-0.48 (m, 3H). MS m/z (ESI): 500.3 [M+H]$^+$.

Example 19

Compound 19

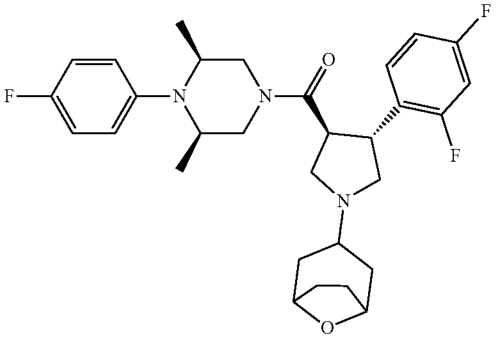

or

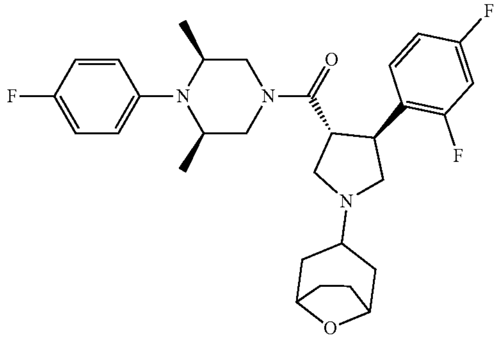

Synthetic Route:

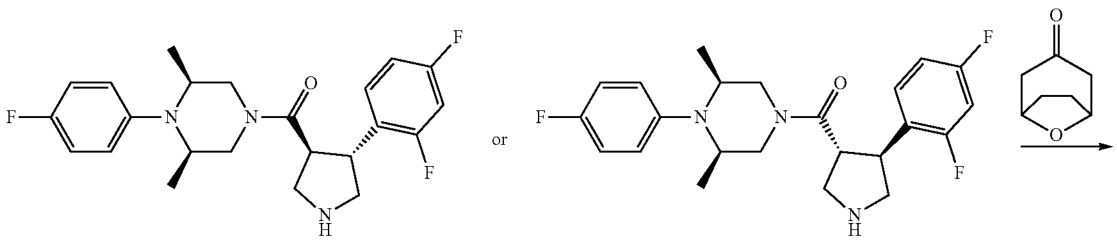

or

Compound 7-5

-continued

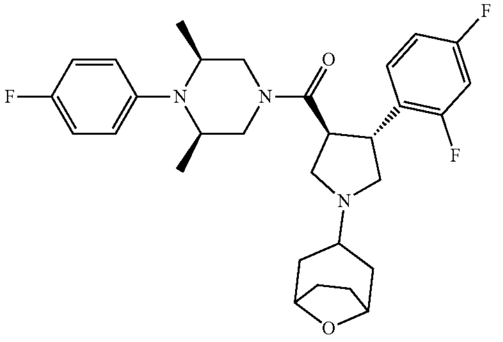

or

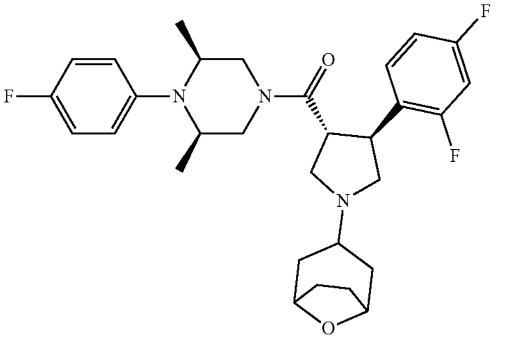

Compound 19

Step 1: Synthesis of Compound 19

The compound 7-5 (300 mg), 8-oxo-bicyclo[3,2,1]octane-3-one (122.39 mg, 970.14 μmol, 1.23 mL) were dissolved in DCM (10 mL) and AcOH (0.3 mL). The reaction solution was stirred at 25° C. for 1 hour, and then added with $NaBH(OAc)_3$ (205.61 mg, 970.14 μmol). The reaction solution was stirred at 25° C. for 16 hours. The reaction solution was extracted by adding 20 mL of saturated aqueous solution of sodium bicarbonate and dichloromethane (10 mL×3). The organic phases were combined, dried over anhydrous sodium sulfate and concentrated under reduced pressure to obtain a crude product. The crude product was purified by flash silica gel column chromatography (petroleum ether: ethyl acetate=1:1 to 0:1) to obtain compound 19. $^1H$ NMR (400 MHz, $CD_3OD$) δ (ppm)=7.44-7.45 (m, 1H), 6.97-7.05 (m, 4H), 6.79-6.89 (m, 2H), 4.48-4.58 (m, 1H), 4.31 (s, 2H), 3.78-4.00 (m, 1H), 3.36-3.46 (m, 2H), 3.08-3.20 (m, 1H), 2.75-2.95 (m, 5H), 2.42-2.60 (m, 2H), 1.70-2.42 (m, 9H), 0.63-0.73 (m, 4H), 0.45-0.46 (m, 2H). MS m/z (ESI): 528.1 $[M+H]^+$.

Example 20

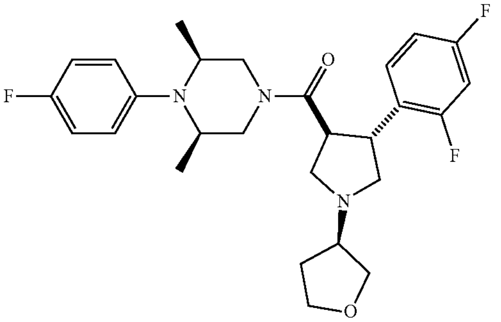

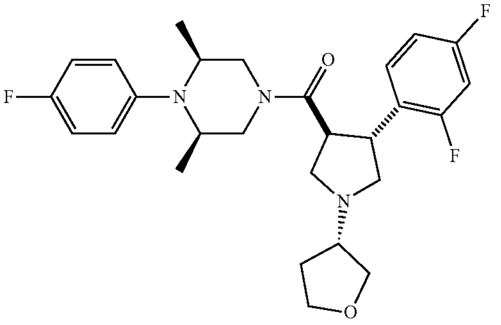

Compound 20a or Compound 20b Compound 20a or Compound 20b

Synthetic Route:

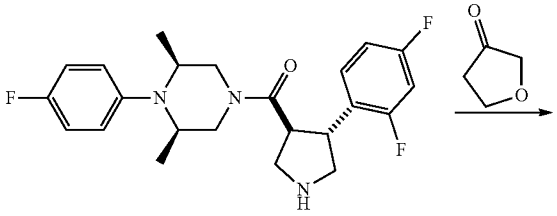

Compound 7-5

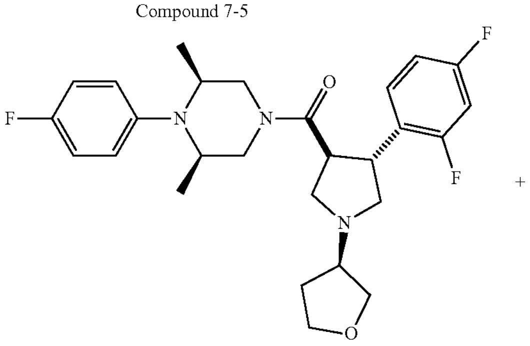

Compound 20a or Compound 20b

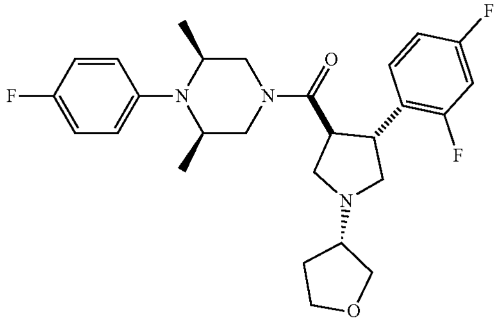

Compound 20a or Compound 20b

Step 1: Synthesis of Compound 20a and compound 20b

The compound 7-5 (500 mg) and 3-tetrahydrofuranone (139.20 mg, 1.62 mmol, 1.23 mL) were dissolved in DCM (10 mL) and AcOH (1 mL). The reaction solution was stirred at 25° C. for 1 hour, and then added with NaBH(OAc) 3 (342.69 mg, 1.62 mmol, 1.5 eq). The reaction solution was stirred at 25° C. for 16 hours. Then the reaction solution was extracted by adding 10 mL of saturated aqueous solution of sodium bicarbonate and dichloromethane (30 mL×3). The organic phases were combined, dried over anhydrous sodium sulfate and concentrated under reduced pressure to obtain a crude product. The crude product was separated and purified by preparative HPLC (chromatographic column: C18 (250*50 mm*10 μm); mobile phase: [water (10 mM ammonium bicarbonate)-acetonitrile]; acetonitrile %: 45%-65%, 10 min), and then separated by SFC (chromatographic column: Phenomenex-Cellulose-2 (250 mm*30 mm, 10 μm); mobile phase: [supercritical $CO_2$-methanol (containing 0.1% ammonia)]; methanol (containing 0.1% ammonia) %: 30%-30%, 5 min) to obtain compound 20a and compound 20b.

SFC analysis method: Chromatographic column: Lux Cellulose-2, 50×4.6 mm I.D., 3 um; mobile phase: [supercritical $CO_2$-methanol (containing 0.1% isopropylamine)]; methanol (containing 0.1% isopropylamine) %: 50%-50%, 3 min.

Compound 20a (retention time=1.102 min, ee=99.7%): $^1$H NMR (400 MHz, $CDCl_3$) δ (ppm)=7.45-7.52 (m, 1H), 6.97-7.04 (m, 4H), 6.74-6.86 (m, 2H), 4.51-4.56 (m, 1H), 4.67-3.96 (m, 5H), 3.01-3.59 (m, 4H), 2.76-2.99 (m, 5H), 2.30-2.55 (m, 2H), 1.86-2.20 (m, 2H), 0.62-0.72 (m, 4H), 0.47-0.49 (m, 2H). MS m/z (ESI): 488.2 $[M+H]^+$.

Compound 20b (retention time=1.236 min, ee=99.5%): $^1$H NMR (400 MHz, $CDCl_3$) δ (ppm)=7.49-7.51 (m, 1H), 6.97-7.04 (m, 4H), 6.74-6.86 (m, 2H), 4.51-4.56 (m, 1H), 4.67-3.96 (m, 5H), 3.01-3.59 (m, 4H), 2.76-2.99 (m, 5H), 2.30-2.55 (m, 2H), 1.86-2.20 (m, 2H), 0.62-0.72 (m, 4H), 0.47-0.48 (m, 2H). MS m/z (ESI): 488.1 $[M+H]^+$.

Example 21

Compound 21a or Compound 21b

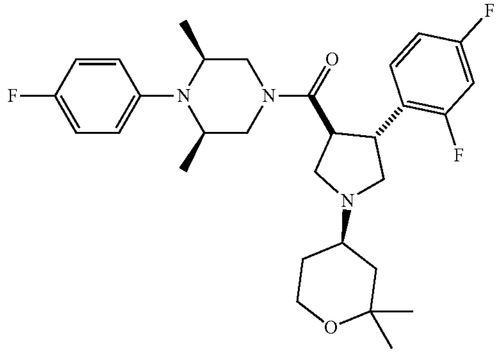

Compound 21a or Compound 21b

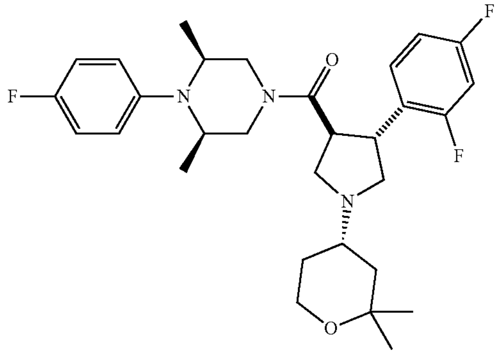

Synthetic Route:

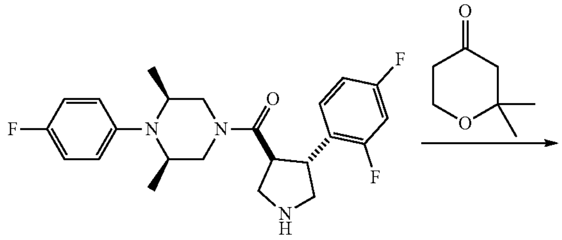

Compound 7-5

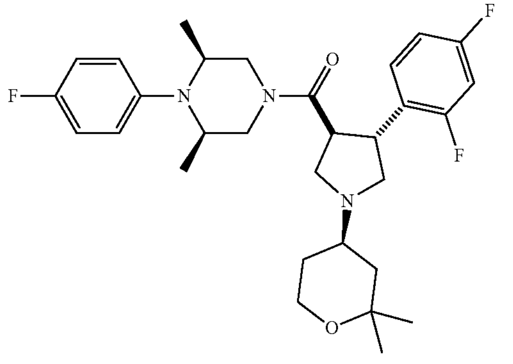

+

Compound 21a or Compound 21b

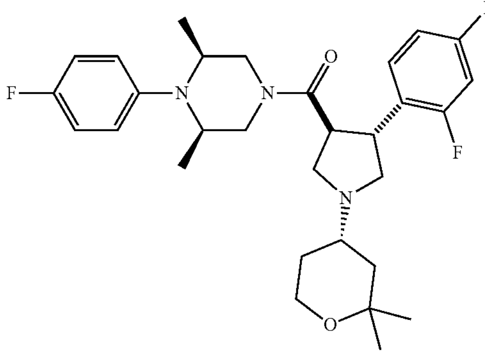

Compound 21a or Compound 21b

Step 1: Synthesis of Compound 21a and Compound 21b

The compound 7-5 (500 mg) and 2,2-dimethyltetrahydropyran-4-one (207.24 mg, 1.62 mmol, 1.23 mL, 1.5 eq) were dissolved in DCM (10 mL) and AcOH (1 mL). The reaction solution was stirred at 25° C. for 1 hour, and then added with NaBH(OAc) 3 (342.69 mg, 1.62 mmol, 1.5 eq). The reaction solution was stirred at 25° C. for 16 hours. Then the reaction solution was extracted by adding 20 mL of saturated aqueous solution of sodium bicarbonate and dichloromethane (30 mL×3). The organic phases were combined, dried over anhydrous sodium sulfate and concentrated under reduced pressure to obtain a crude product. The crude product was separated and purified by preparative HPLC (chromatographic column: C18 (250*50 mm*10 μm); mobile phase: [Water (10 mM ammonium bicarbonate)-acetonitrile]; Acetonitrile %: 50%-70%, 10 min), and then separated by SFC (chromatographic column: DAICEL CHIRALCEL OX (250 mm*30 mm, 10 μm); mobile phase: [supercritical $CO_2$-isopropanol (containing 0.1% ammonia)]; isopropanol (containing 0.1% ammonia) %: 25%-25%, 5 min) to obtain compound 21a and compound 21b.

SFC analysis method: Chromatographic column: Lux Cellulose-2, 50×4.6 mm I.D., 3 μm; mobile phase: [supercritical $CO_2$-methanol (containing 0.1% isopropylamine)]; methanol (containing 0.1% isopropylamine) %: 50%-50%, 3 min).

Compound 21a (retention time=1.027 min, ee=100%): $^1H$ NMR (400 MHz, $CDCl_3$) δ (ppm)=7.48-7.51 (m, 1H), 6.98-7.04 (m, 4H), 6.77-6.87 (m, 2H), 4.53-4.57 (m, 1H), 3.16-4.15 (m, 6H), 2.76-2.93 (m, 8H), 1.76-1.79 (m, 2H), 1.41-1.59 (m, 2H), 1.22-1.25 (m, 6H), 0.62-0.72 (m, 4H), 0.49-0.50 (m, 2H). MS m/z (ESI): 530.2 $[M+H]^+$.

Compound 21b (retention time=1.090 min, ee=96%): $^1H$ NMR (400 MHz, $CDCl_3$) δ (ppm)=7.48-7.51 (m, 1H), 6.98-7.04 (m, 4H), 6.77-6.87 (m, 2H), 4.53-4.57 (m, 1H), 3.16-4.15 (m, 6H), 2.76-2.93 (m, 8H), 1.76-1.79 (m, 2H), 1.41-1.59 (m, 2H), 1.22-1.25 (m, 6H), 0.62-0.72 (m, 4H), 0.49-0.50 (m, 2H). MS m/z (ESI): 530.2 $[M+H]^+$.

Example 22

Compound 21a

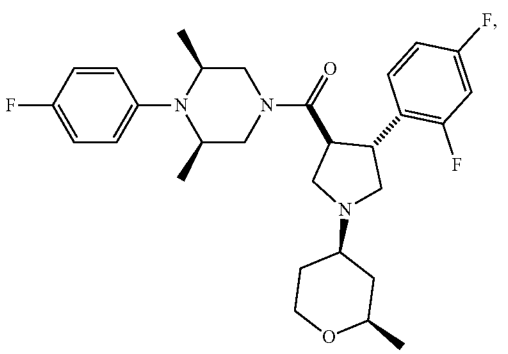

Compound 21b

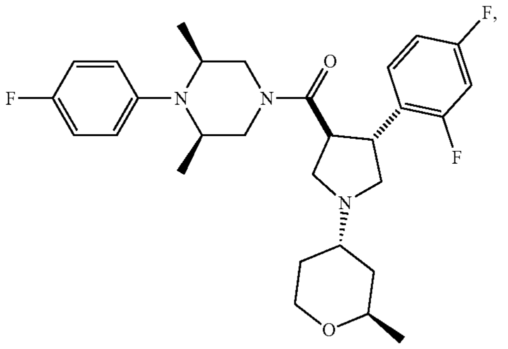

Compound 21c

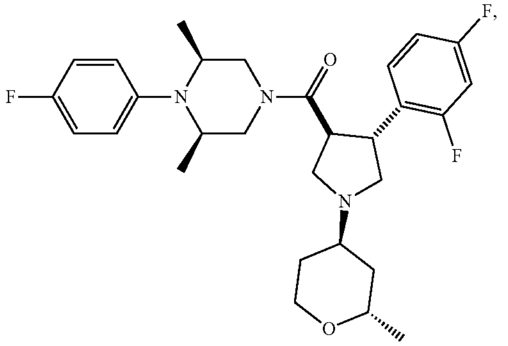

-continued

Compound 22d

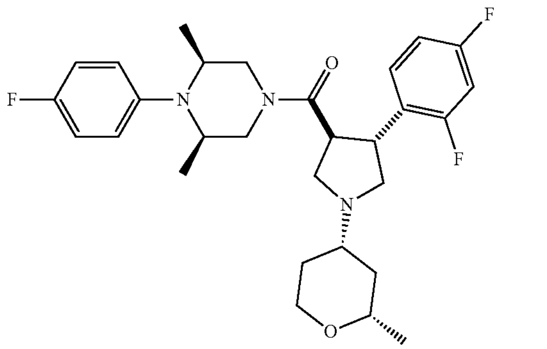

Synthetic Route:

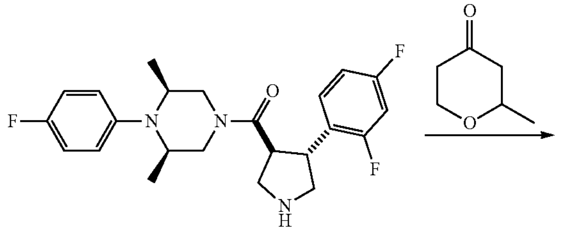

Compound 7-5

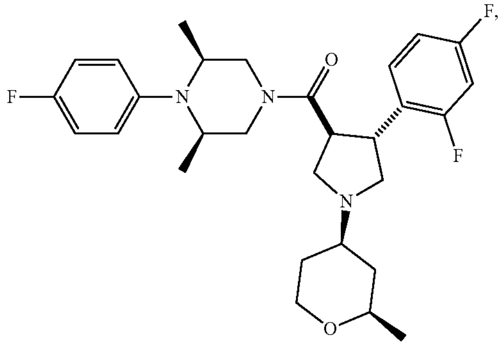

Compound 21a

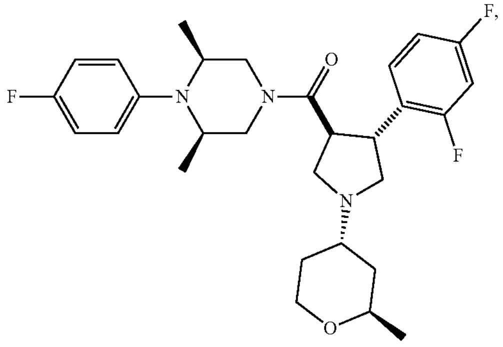

Compound 21b

-continued

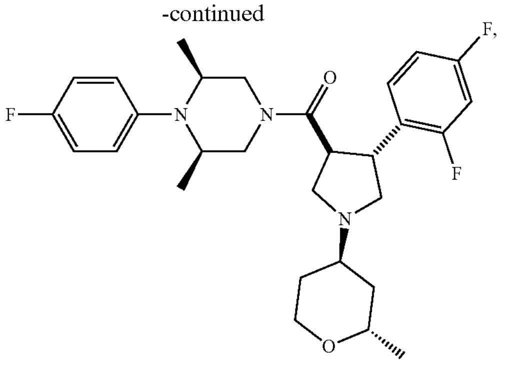

Compound 21c,

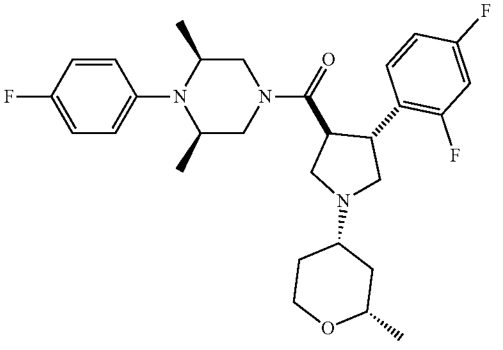

Compound 22d

Step 1: Synthesis of Compound 22a-22d

The compound 7-5 (500 mg) and 2-methyltetrahydropyran-4-one (246.07 mg, 2.16 mmol, 88.01 μL, 2 eq) were dissolved in DCM (5 mL) and AcOH (0.5 mL). The reaction solution was stirred at 25° C. for 1 hour, and then added with $NaBH(OAc)_3$ (342.69 mg, 1.62 mmol, 1.5 eq). The reaction solution was stirred at 25° C. for 16 hours. Then the reaction solution was extracted by adding 20 mL of saturated aqueous solution of sodium bicarbonate and dichloromethane (30 mL×3). The organic phases were combined, dried over anhydrous sodium sulfate and concentrated under reduced pressure to obtain a crude product. The crude product was separated and purified by preparative HPLC (chromatographic column: Phenomenex C18 75*30 mm*3 um; mobile phase: [water (10 mM ammonium bicarbonate)-acetonitrile]; acetonitrile %: 30%-65%, 8 min), Peakl (retention time=2.932 min, chromatographic column: Xbridge C18 5 μm 2.1*50 mm; mobile phase: [water (10 mM ammonium bicarbonate)-acetonitrile]; acetonitrile %: 10%-80%, 4.5 min) and Peak2 (retention time=3.172 min, chromatographic column: Xbridge C18 5 um 2.1*50 mm; mobile phase: [water (10 mM ammonium bicarbonate)-acetonitrile]; acetonitrile %: 10%-80%, 4.5 min).

The chiral HPLC separation of Peak 1 (chromatographic column: DAICEL CHIRALPAK IC (250 mm*30 mm, 10 μm); mobile phase: [n-heptane-ethanol (containing 0.1% isopropylamine)]; ethanol (containing 0.1% isopropylamine) %: 20%-20%, 10 min) was performed to obtain compound 22a and compound 22b.

SFC analysis method: Chromatographic column: Chiralpak IC-3, 100×4.6 mm I.D., 3 μm; Mobile phase: [n-hexane-ethanol (containing 0.1% isopropylamine)]; ethanol (containing 0.1% isopropylamine) %: 20%-20%, 6.0 min).

The SFC separation of Peak2 (chromatographic column: DAICEL CHIRALPAK IC (250 mm*30 mm, 10 μm); mobile phase: [supercritical $CO_2$-isopropanol (containing 0.1% ammonia)]; isopropanol (containing 0.1% ammonia) %: 33%-33%, 8 min] was performed to obtain compound 22c and compound 22d.

SFC analysis method: Chromatographic column: Chiralpak IC-3, 100×4.6 mm I.D., 3 um; mobile phase: [Supercritical $CO_2$-Isopropyl alcohol (containing 0.1% isopropylamine)]; Isopropyl alcohol (containing 0.1% isopropylamine) %: 50%-50%, 4.0 min).

Compound 22a (retention time=3.118 min): $^1H$ NMR (400 MHz, DMSO-d6) δ (ppm)=7.65-7.50 (m, 1H), 7.26-7.02 (m, 6H), 4.32-4.12 (m, 1H), 4.02-3.81 (m, 2H), 3.81-3.66 (m, 1H), 3.57-3.43 (m, 1H), 3.25-3.04 (m, 1H), 3.02-2.78 (m, 3H), 2.78-2.58 (m, 4H), 2.46-2.26 (m, 2H), 1.93-1.70 (m, 2H), 1.39-1.13 (m, 2H), 1.13-1.06 (m, 3H), 1.06-0.97 (m, 1H), 0.70-0.46 (m, 6H). MS m/z (ESI): 516.2 $[M+H]^+$.

Compound 22b (retention time=4.100 min): $^1H$ NMR (400 MHz, DMSO-d6) δ (ppm)=7.65-7.50 (m, 1H), 7.25-7.01 (m, 6H), 4.32-4.12 (m, 1H), 4.00-3.82 (m, 2H), 3.81-3.67 (m, 1H), 3.55-3.33 (m, 2H), 3.29 (br s, 1H), 3.23-3.03 (m, 1H), 3.02-2.78 (m, 3H), 2.77-2.61 (m, 3H), 2.46-2.25 (m, 2H), 1.92-1.69 (m, 2H), 1.36-1.21 (m, 1H), 1.16-0.97 (m, 4H), 0.71-0.45 (m, 6H). MS m/z (ESI): 516.2 $[M+H]^+$.

Compound 22c (retention time=1.861 min): $^1H$ NMR (400 MHz, DMSO-d6) δ (ppm)=7.70-7.57 (m, 1H), 7.25-7.04 (m, 6H), 4.33-4.11 (m, 1H), 4.01-3.79 (m, 2H), 3.79-3.63 (m, 2H), 3.60-3.40 (m, 2H), 3.27-3.07 (m, 1H), 2.99-2.78 (m, 3H), 2.77-2.57 (m, 3H), 2.47-2.30 (m, 1H), 1.83-1.73 (m, 1H), 1.68-1.54 (m, 2H), 1.40-1.28 (m, 1H), 1.08-1.00 (m, 3H), 0.71-0.44 (m, 6H). MS m/z (ESI): 516.2 $[M+H]^+$.

Compound 22d (retention time=1.984 min): $^1H$ NMR (400 MHz, DMSO-d6) δ (ppm)=7.70-7.57 (m, 1H), 7.26-6.97 (m, 6H), 4.31-4.13 (m, 1H), 4.02-3.84 (m, 1H), 3.84-3.64 (m, 3H), 3.62-3.40 (m, 2H), 3.28-3.07 (m, 1H), 2.99-2.79 (m, 3H), 2.78-2.54 (m, 4H), 2.46-2.30 (m, 1H), 1.78-1.55 (m, 3H), 1.39-1.26 (m, 1H), 1.08-0.99 (m, 3H), 0.69-0.45 (m, 6H). MS m/z (ESI): 516.2 $[M+H]^+$.

Example 23

Compound 23 ↵

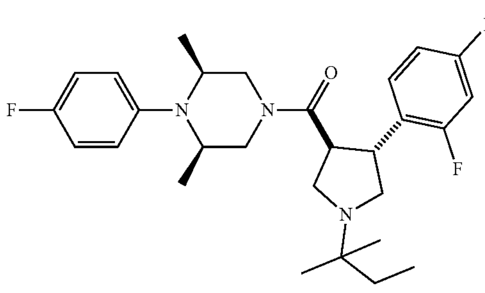

Synthetic Route:

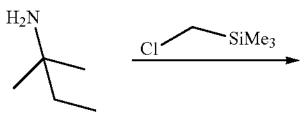

Compound 23-1

-continued

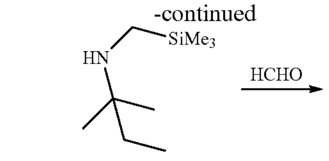

Compound 23-2

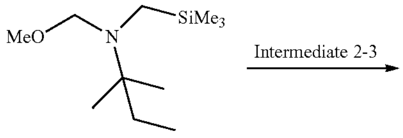

Compound 23-3

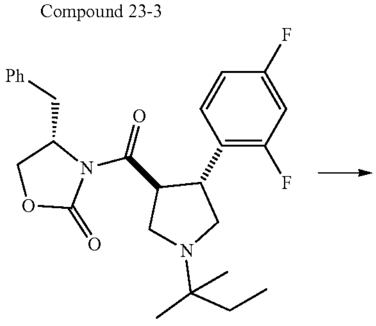

Compound 23-4

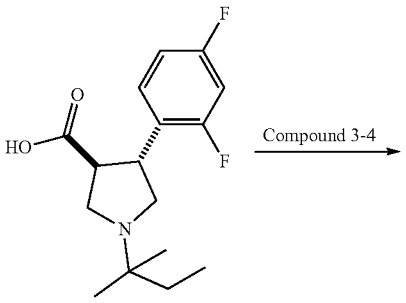

Compound 23-5

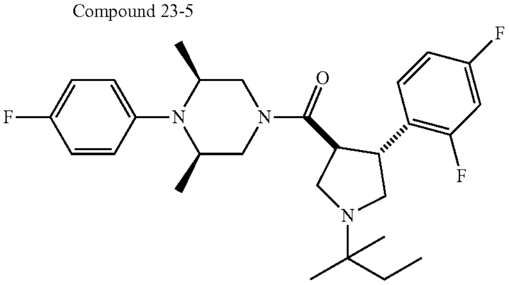

Compound 23

Step 1: Synthesis of Compound 23-2

The compound 23-1 (20 g, 163.04 mmol, 22.75 mL), trimethylchloromethylsilane (532.69 g, 375.00 mmol, 43.81 mL) and DMSO (10 mL) were added into a reaction flask. The reaction solution was heated slowly to 90° C. and stirred continuously for 16 hours. At the end of the reaction, the heating device was removed, and the reaction solution was cooled and allowed to stand naturally for phase separation. The upper layer of organic phase was dissolved in 100 mL of ethyl acetate, and washed with water (100 mL×2). The organic phase was dried over anhydrous sodium sulfate and concentrated under reduced pressure to obtain compound 23-2, $^1$H NMR (400 MHz, $CDCl_3$, 298 K) δ (ppm)=1.90-1.85 (m, 2H), 1.40-1.32 (m, 2H), 0.96 (s, 6H), 0.81-0.75 (m, 3H), 0.02 (s, 9H).

Step 2: Synthesis of Compound 23-3

A 37% formaldehyde aqueous solution (20.43 g, 251.77 mmol), methanol (8.07 g, 251.77 mmol, 10.19 mL) and potassium carbonate (34.80 g, 251.77 mmol) were added into a dry flask. The reaction system was cooled to 0° C., then added with the compound 23-2 (14.55 g, 83.92 mmol), slowly warmed to room temperature and stirred continuously at 25° C. for 12 hours. The reaction solution was filtered, the filter cake was washed with a small amount of ethyl acetate, and the filtrate was extracted by adding 20 mL of water and ethyl acetate (50 mL×3). The organic phases were combined, dried over anhydrous sodium sulfate, and concentrated under reduced pressure to obtain compound 23-3, which can be directly used in the next reaction without further purification. (The contained unreacted compound 23-2 would not affect the next reaction). $^1$H NMR (400 MHz, $CDCl_3$, 298 K) δ (ppm)=4.19 (s, 2H), 3.34-3.27 (m, 2H), 2.24-2.19 (m, 3H), 1.88-1.87 (m, 3H), 1.37-1.34 (m, 3H), 1.16 (t, J=7.0 Hz, 3H), 1.09-1.07 (m, 2H), 0.02 (s, 9H).

Step 3: Synthesis of Compound 23-4

The compound 23-3 (8.64 g, 13.11 mmol) and the intermediate 2-3 (1.5 g, 4.37 mmol) dissolved in dichloromethane (15 mL) were added into a dry three-necked flask, and trifluoroacetic acid (1.49 g, 13.11 mmol, 970.44 μL) was added dropwise slowly, and then reaction was conducted under stirring at 15° C. for 1 hour. Then the reaction solution was added with 50 mL of a saturated sodium bicarbonate solution, and allowed to stand for phase separation. The aqueous phase was extracted by adding dichloromethane (50 mL×2), and the organic phases were combined and dried over anhydrous sodium sulfate and then subjected to silica gel column chromatography (petroleum ether:ethyl acetate=10:1-1:1) for gradient elution. The resulting eluate was concentrated to dryness, added with methyl tert-butyl ether (10 mL) and homogenized for 2 hours, filtered, and then homogenized with petroleum ether-ethyl acetate (1:15) to obtain compound 23-4. $^1$H NMR (400 MHz, DMSO-d6, 298 K) δ (ppm)=7.58-7.46 (m, 1H), 7.28-7.17 (m, 2H), 7.17-7.08 (m, 3H), 6.99-6.93 (m, 2H), 4.72-4.63 (m, 1H), 4.36-4.30 (m, 1H), 4.21-4.11 (m, 2H), 4.02-3.94 (m, 1H), 3.21-3.14 (m, 1H), 3.07 (t, J=8.3 Hz, 1H), 2.93-2.84 (m, 2H), 2.76-2.65 (m, 2H), 1.42-1.33 (m, 2H), 1.01-0.91 (m, 6H), 0.82 (t, J=7.3 Hz, 3H). MS m/z (ESI): 457.2 $[M+H]^+$.

Step 4: Synthesis of Compound 23-5

The compound 23-4 (0.71 g, 1.56 mmol) was dissolved in THF (7 mL), and added with a solution of $LiOH{\cdot}H_2O$ in $H_2O$ (3 mL) (195.77 mg, 4.67 mmol) at 0° C., and the reaction solution was stirred at 25° C. for 4 hours. The reaction solution was concentrated to dryness under reduced pressure, and then extracted by adding water (100 mL) and ethyl acetate (30 mL×3). The organic phase was discarded, and the aqueous phase was adjusted to a pH of 2 with 2 M dilute hydrochloric acid and concentrated under reduced pressure to obtain compound 23-5. $^1$H NMR (400 MHz, DMSO-d6, 298 K) δ (ppm)=7.99-7.65 (m, 1H), 7.31-7.18 (m, 1H), 7.17-7.08 (m, 1H), 4.32-3.79 (m, 3H), 3.28-3.17 (m, 1H), 3.17-3.14 (m, 2H), 1.81-1.67 (m, 2H), 1.35-1.25 (m, 6H), 0.91 (t, J=7.3 Hz, 3H). MS m/z (ESI): 298.0 $[M+H]^+$.

Step 5: Synthesis of Compound 23

The hydrochloride salt of the compound 3-4 (322.21 mg), the compound 23-5 (460 mg, 1.55 mmol) and triethylamine (782.73 mg, 7.74 mmol, 1.08 mL) were dissolved in dichloromethane (6 mL), added with a 50% solution of propylphosphoric anhydride in ethyl acetate (1.38 mL, 2.32 mmol), and stirred at 25° C. for 1 hour. The reaction solution was concentrated under reduced pressure and separated by preparative HPLC (chromatographic column: Phenomenex C18 80*40 mm*3 μm; mobile phase: water (10 mM ammonium bicarbonate)-acetonitrile]; acetonitrile %: 40%-80%, 8 min) to obtain compound 23. $^1$H NMR (400 MHz, DMSO-d6, 298 K) δ (ppm)=7.66-7.50 (m, 1H), 7.26-6.99 (m, 6H), 4.31-4.09 (m, 1H), 3.93-3.68 (m, 2H), 3.54-3.36 (m, 1H), 3.21-3.05 (m, 1H), 3.05-2.98 (m, 1H), 2.97-2.57 (m, 5H), 2.47-2.28 (m, 1H), 1.44-1.34 (m, 2H), 1.03-0.91 (m, 6H), 0.88-0.78 (m, 3H), 0.70-0.45 (m, 6H). MS m/z (ESI): 488.2 $[M+H]^+$.

Biological Testing

Experimental Example 1: Test of In Vitro Activity of MCR Receptors

Test purpose: to evaluate the agonistic effect of the compound on MCRs by detecting intracellular cAMP signal changes.

Test Materials:

TABLE 1

Test materials

| Reagents and Materials | Supplier | Product Number |
|---|---|---|
| HEK293T/MCR cell line | HDB | / |
| DMEM medium | Gibco | #12100 |
| Fetal bovine serum (FBS) | Biosera | #FB-1058/500 |
| 0.25% trypsin/EDTA | HDB | #MCP007 |
| Dimethyl sulfoxide (for frozen cell) | Sigma | #D2650 |
| Dimethyl sulfoxide (for compounds preparation) | Amresco | #0231 |
| Phosphate buffered saline (PBS) solution | Invitrogen | #70013 |
| 3-isobutyl-1-methylxanthine (IBMX) | Sigma | #I7018 |
| cAMP Dynamic2 Kit | Cisbio | #62AM4PEJ |
| 384-well compound plate | Corning | #3824 |
| 384-well Echo LDV plate (low dead volume) | Labcyte | #LP-0200 |
| Echo Liquid Workstation | Labcyte | / |
| Envision multifunctional microplate reader | PerkinElmer | / |

Test Procedures and Methods:

Cells were resuspended with 1×PBS+500 μM IBMX. 10 μL of the cell suspension was added into a 384-well plate to be tested, and the cell concentration was adjusted to $1\times10^4$ cells per well for later use. A pre-prepared solution of the compound to be tested was added, and dimethyl sulfoxide of the same volume was added to blank control wells. The test plate was centrifuged at 300 rpm for 1 minute, incubated at 37° C. for 30 minutes, and added with 5 μL of CAMP-d2 and 5 μL of a cAMP-cry antibody detection reagent. The test plate was centrifuged at 300 rpm for 1 minute, and incubated at room temperature for 60 minutes. The test plate was placed in the Envision multifunctional microplate reader for reading, with a detection wavelength of 665/615 nm. The test results were shown in Table 2:

TABLE 2

Test results of MCRs activity

| Compound ID | MC4R $EC_{50}$(nM) | MC1R $EC_{50}$(nM) | MC3R $EC_{50}$(nM) | MC5R $EC_{50}$(nM) |
|---|---|---|---|---|
| Compound 1 | 148 | 2332 | >10000 | >10000 |
| Compound 3 | 30 | 300 | 2400 | >10000 |
| Compound 5 | 35 | 882 | 3502 | >10000 |
| Hydrochloride salt of compound 6 | 24 | 80 | 2029 | 1152 |
| compound 7 | 12 | 459 | 4215 | >10000 |
| Hydrochloride salt of compound 8 | 18 | 55 | 1469 | 2800 |
| Compound 9 | 16 | 45 | 1761 | 402 |
| Compound 11 | 0.4 | 82 | 26 | 2128 |
| Compound 12 | 0.2 | 234 | 5 | 740 |
| Compound 13 | 50 | >10000 | 3299 | >10000 |
| Compound 14 | 10 | 575 | 672 | 919 |
| Compound 15 | 3 | 580 | 574 | >10000 |
| Compound 16 | 6 | 167 | 254 | 1175 |
| Compound 17 | 6.7 | 55 | 1104 | 8146 |
| Compound 18 | 4 | 29 | 201 | 1366 |
| Compound 20a | 26 | 2012 | 3126 | >10000 |
| Compound 21b | 5.3 | 492 | 268 | >10000 |
| Compound 22a | 0.03 | 790 | 265 | >10000 |
| Compound 22d | 1.9 | 106 | 696 | >10000 |
| Compound 23 | 4 | 58 | 316 | 1949 |

Conclusion: The compound of the present disclosure had selective agonistic effects on human MC4R receptors.

Experimental Example 2: Test of Pharmacokinetic Parameters in Rat Plasma 4 healthy SD rats of 6-9 weeks old were selected and randomly divided into two groups, 2 rats in each group. One group was administered with the test compound via intravenous injection, with 5% DMSO+95% (a 10% HP-β-CD aqueous solution) as a solvent, and the other group was administered with the test compound by gavage, with a 50 mM citric acid buffer solution at pH=5 as a solvent. Plasma samples were collected from animals in both intravenous and intragastric groups at 0.083 hour, 0.25 hour, 0.5 hour, 1.0 hour, 2.0 hours, 4.0 hours, 6.0 hours, 8.0 hours and 24 hours after administration, respectively. Quantitative analysis of all biological samples was performed using an LC-MS/MS method, with WinNonlin™ Version 6.3 (Pharsight, Mountain View, CA) pharmacokinetic software, to calculate relevant pharmacokinetic parameters using a non-atrioventricular model linear logarithmic trapezoid method. $AUC_{0-last}$ represented an area under a plasma concentration time curve from a time point zero to a last time point where the concentration can be detected; p.o. represented oral administration; i.v. represented intravenous injection; $T_{12}$ represented the half life; CL represented the clearance rate; Vd represented the apparent distribution volume; $AUC_{0-last}$ represented the area under the curve; $C_{max}$ represented the peak concentration; $T_{max}$ represented the peak time; and F % represented oral bioavailability.

Test Results

The test results of the compound of the present disclosure were shown in Table 3.

TABLE 3

Pharmacokinetic properties of the compound

| | | Compound 7 |
|---|---|---|
| i.v. 2 mg/kg | $T_{1/2}$ (h) | 1.5 |
| | Vd (L/kg) | 8.0 |
| | CL(mL/min/kg) | 73 |
| | $AUC_{0-last}$ (nM · h) | 897 |

TABLE 3-continued

| Pharmacokinetic properties of the compound | | |
|---|---|---|
| | | Compound 7 |
| p.o. 5 mg/kg | $T_{max}$ (h) | 1.0 |
| | $C_{max}$ (nM) | 195 |
| | $AUC_{0\text{-}last}$ (nM · h) | 796 |
| | F % | 37% |

Conclusion: The compound of the present disclosure showed good pharmacokinetic properties in rats.

Experimental Example 3: Determination of Drug Concentration in Brain Tissues of Rats 3.1 6 healthy SD rats of 6-9 weeks old were selected, and the test compound was administered via intravenous injection. Two animals were randomly selected at 0.5 hour, 2 hours and 4 hours after administration respectively, and plasma and brain tissue samples were collected, and the quantitative assay of all biological samples was performed using the LC-MS/MS method.

The test results of the compound of the present disclosure were shown in Table 4.

TABLE 4

| Brain-to-blood ratio of the compound in rats | | | | |
|---|---|---|---|---|
| | | Compound 7 (0.5 hour) | Compound 7 (2 hours) | Compound 7 (4 hours) |
| i.v. 2 mg/kg | Brain drug concentration (nmol/L) | 2834 | 965 | BQL |
| | Plasma drug concentration (nmol/L) | 362 | 141 | BQL |
| | Brain-to-blood ratio | 7.8 | 6.9 | NA |

BQL: below the limit of quantization, NA indicated failure of calculation.

3.2 6 healthy SD rats of 6-9 weeks old were selected, and the test compound was administered by oral gavage (with a solvent of 50 mM citrate buffer solution, pH=5). Two animals were randomly selected at 0.5 hour, 1 hour and 4 hours after administration respectively, and plasma and brain tissue samples were collected for quantitative analysis of all biological samples using the LC-MS/MS method.

The test results of the compound of the present disclosure were shown in Table 5.

TABLE 5

| Brain-to-blood ratio of the compound in rats | | | | |
|---|---|---|---|---|
| | | Compound 7 (0.5 hour) | Compound 7 (1 hour) | Compound 7 (4 hours) |
| p.o. 20 mg/kg | Brain drug concentration (nmol/L) | 8600 | 9675 | 11400 |
| | Plasma drug concentration (nmol/L) | 783 | 899 | 1197 |
| | Brain-to-blood ratio | 11.0 | 10.8 | 9.5 |
| | Kp, uu | 1.5 | 1.5 | 1.3 |

Conclusion: the compound of the present disclosure could penetrate the blood brain barrier into brain tissues at a high brain-to-blood ratio in rats, and reached a high drug concentration.

Experimental Example 4: Test of In Vitro MDCK-MDR1 Permeability

MDR1-MDCKII cells (from the Netherlands Cancer Institute) were inoculated onto a 96-plate (from Corning) with a cell density of $2.5\times10^5$ cells/mL, and cultured for 4-7 days to form a co-polymeric cell monolayer. A Hank's equilibrium salt buffer (pH=7.40±0.05) containing mM of 4-hydroxyethyl piperazine ethanesulfonic acid was used as a transport buffer. The bidirectional transport of the test compound at a concentration of 2 μM was tested, and the concentration of DMSO in the incubation system was controlled below 1%. After sample loading, the cell plate was placed at 37±1° C. for inoculation with 5% $CO_2$ under a saturated humidity condition for 150 minutes. All samples were subjected to quantitative analysis using the LC-MS/MS method.

The apparent permeability coefficient ($P_{app}$, cm/s), the efflux ratio, and the recovery rate were calculated using the following formula.

The apparent permeability coefficient ($P_{app}$, cm/s) was calculated using the following formula:

$$P_{app} = (dC_r/d_t) \times V_r/(A \times C_0)$$

$DC_r/d_t$ was the cumulative concentration (μM/s) of the compound at the receiving end per unit time; $V_r$ was the volume of the solution at the receiving end (the solution volumes at the top and base ends were 0.075 mL and 0.250 mL, respectively); A was the relative surface area of the cell monolayer (0.0804 $cm^2$); and $C_0$ was the initial concentration (nM) of a test sample at the administration end or the peak area ratio of a control sample.

The efflux ratio was calculated using the following formula:

$$\text{Efflux ratio} = P_{app}(BA)/P_{app}(AB)$$

The recovery rate was calculated using the following formula:

$$\%\ \text{recovery rate} = 100 \times [(V_r \times C_r) + (V_d \times C_d)]/(V_d \times C_0)$$

$C_0$ was the initial concentration (nM) of the test sample at the administration end or the peak area ratio of the control sample; $V_d$ was the volume of the administration end (0.075 mL on the top side and 0.250 mL on the base side); Ca and Cr were the final concentrations (nM) of the test sample at the administration end and the receiving end, or the peak area ratios of the control sample, respectively.

The test results of the compound of the present disclosure were shown in Table 6.

TABLE 6

| In vitro permeability data of the compound | | | | |
|---|---|---|---|---|
| Compound | $P_{app}$(AB) ($10^{-6}$ cm/s) | $P_{app}$(BA) ($10^{-6}$ cm/s) | Efflux ratio | Rating |
| Compound 7 | 13.46 | 13.15 | 0.98 | High permeability, low efflux |

Conclusion: The compound of the present disclosure was good in permeability and low in efflux ratio.

What is claimed is:

1. A compound of formula (III) or pharmaceutically acceptable salts thereof, (III)

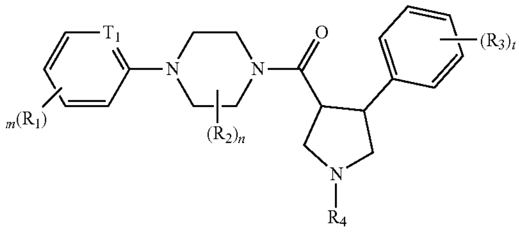

wherein, each $R_1$ is independently selected from the group consisting of halogen, $C_{1-3}$ alkyl, $C_{1-3}$ alkoxyl, —C(═O)$NR_aR_b$ and —$CH_2C$(═O)$NR_aR_b$, the $C_{1-3}$ alkyl and the $C_{1-3}$ alkoxyl are optionally substituted by 1, 2 or 3 halogens;

each $R_2$ is independently selected from the group consisting of $C_{1-3}$ alkyl and $C_{3-6}$ cycloalkyl;

each $R_3$ is independently selected from the group consisting of halogen, —$C_{1-3}$ alkyl and $C_{1-3}$ alkoxyl;

$R_4$ is selected from the group consisting of tert-butyl, phenyl, pyridyl, pyridazinyl, tetrahydropyranyl, cyclobutyl, cyclohexyl, tetrahydrofuranyl and oxabicyclooctyl, each of which is independently optionally substituted by 1, 2 or 3 $R_c$;

$R_a$ and $R_b$ are each independently selected from the group consisting of H and $C_{1-3}$ alkyl;

each $R_c$ is independently selected from the group consisting of halogen, —CN and $C_{1-3}$ alkyl;

m and t are each independently selected from the group consisting of 0, 1 and 2;

n is 1 or 2; and $T_1$ is selected from the group consisting of N and CH.

2. The compound or pharmaceutically acceptable salts thereof according to claim 1, wherein the $R_a$ and $R_b$ are each independently selected from the group consisting of H and —$CH_3$.

3. The compound or pharmaceutically acceptable salts thereof according to claim 1, wherein each of the $R_1$ is independently selected from the group consisting of F, Cl, —$CF_3$, —C(═O)$NHCH_3$ and —$CH_2C$(═O)$NHCH_3$.

4. The compound or pharmaceutically acceptable salts thereof according to claim 1, wherein a structural unit

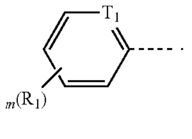

is selected from the group consisting of

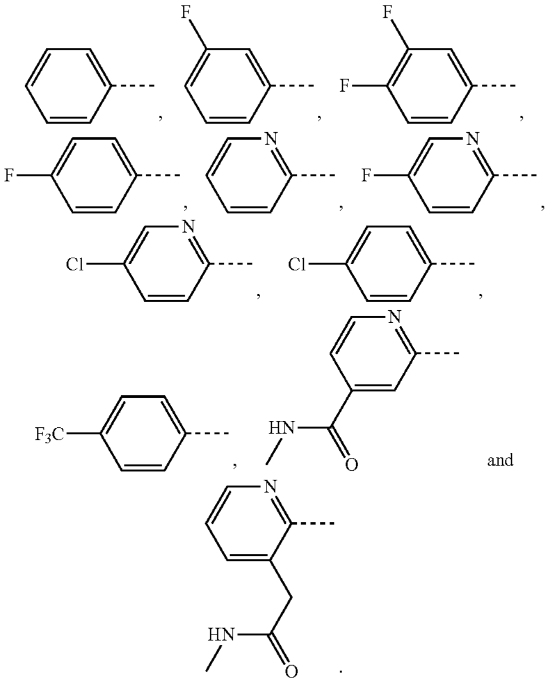

, , , , , , , , and .

5. The compound or pharmaceutically acceptable salts thereof according to claim 1, wherein each of the $R_2$ is independently selected from the group consisting of —$CH_3$ and cyclopropyl.

6. The compound or pharmaceutically acceptable salts thereof according to claim 1, wherein each of the $R_3$ is independently selected from the group consisting of F, Cl and Br.

7. The compound or pharmaceutically acceptable salts thereof according to claim 1, wherein each of the Re is independently selected from the group consisting of —CN and —$CH_3$.

8. The compound or a pharmaceutically acceptable salt thereof according to claim 1, wherein the $R_4$ is selected from the group consisting of

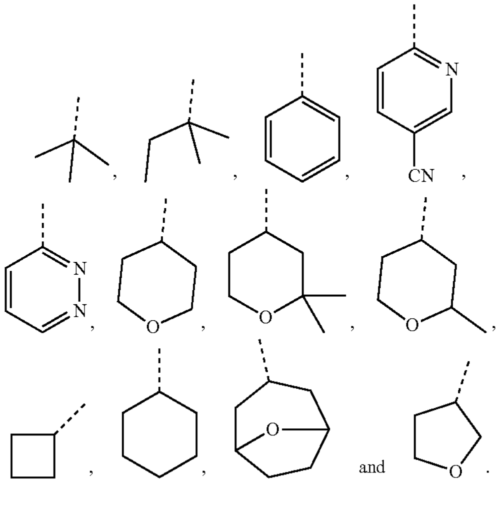

, , , , , , , , , , and .

9. The compound or pharmaceutically acceptable salts thereof according to claim 1 which is selected from:

(I)

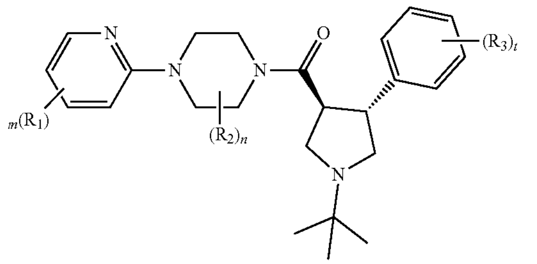

(II-1)

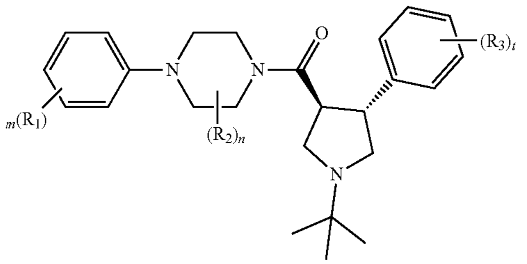

(II-2)

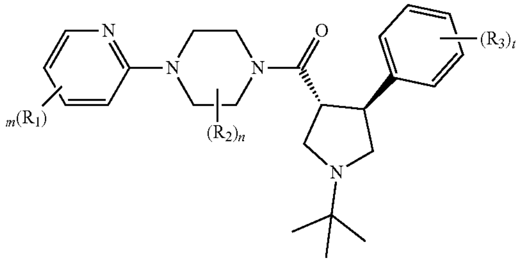

(II-3)

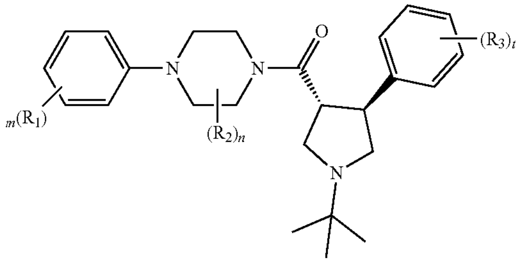

wherein, $R_1$, $R_2$, $R_3$, m, n and t are as defined in claim 1.

10. The compound or pharmaceutically acceptable salts thereof according to claim 1, which is selected from:

(III-1)

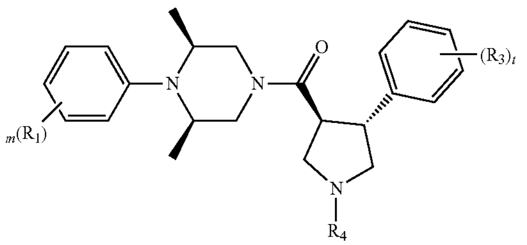

-continued (III-2)

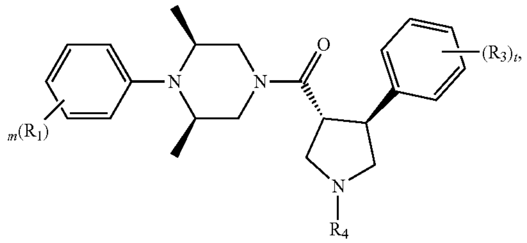

wherein, $R_1$, $R_3$, $R_4$, m and t are as defined in claim 1.

11. A compound represented by a formula selected from the group consisting of:

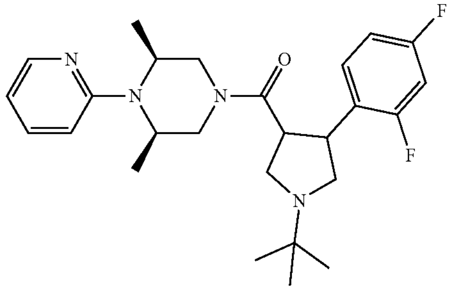

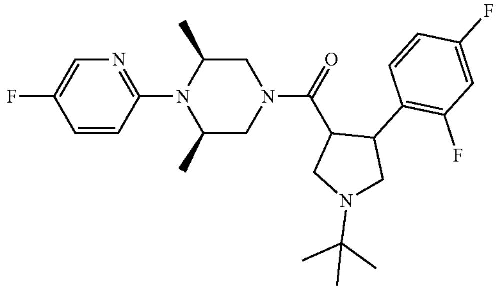

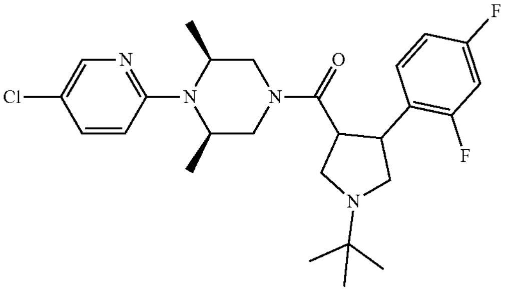

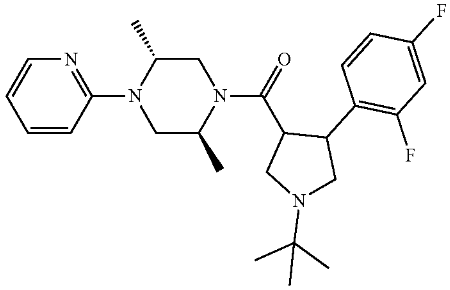

-continued
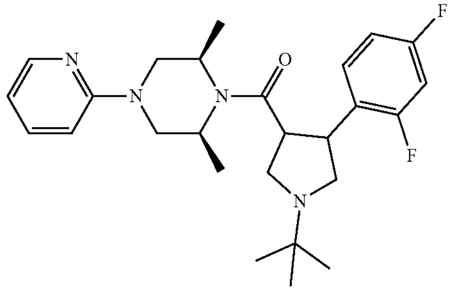
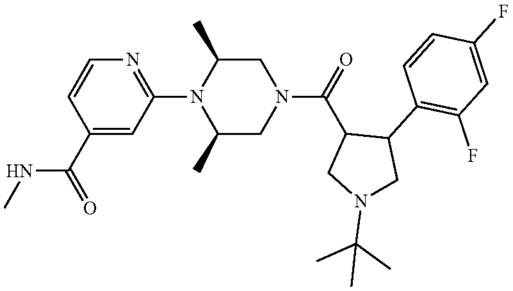
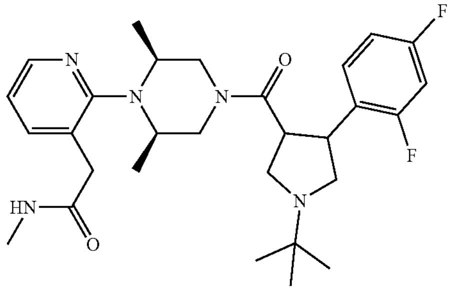
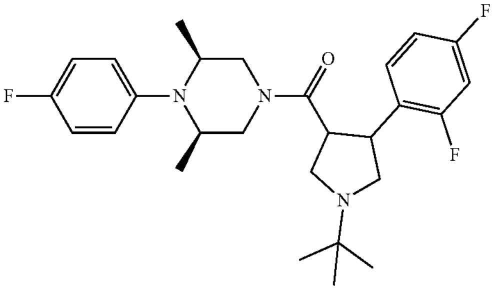
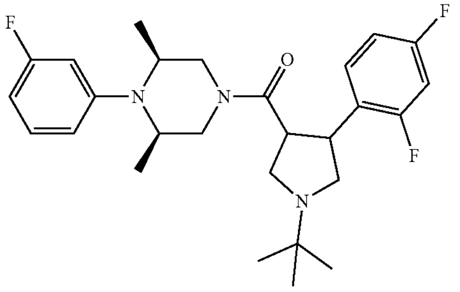
-continued
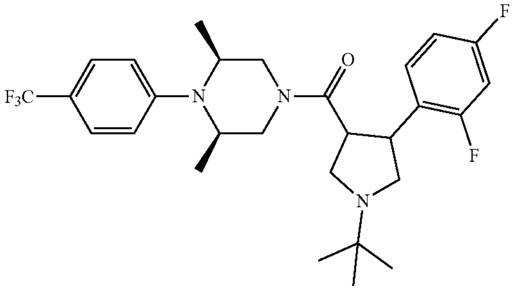
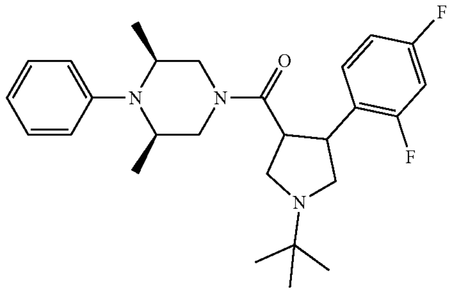
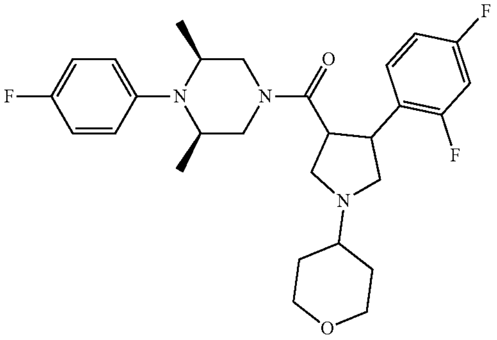
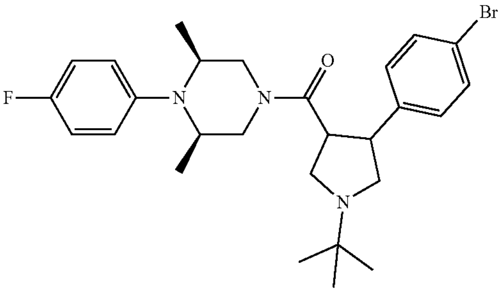
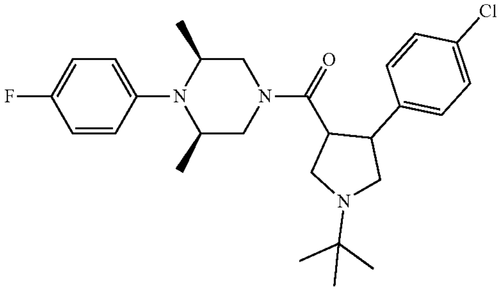

-continued
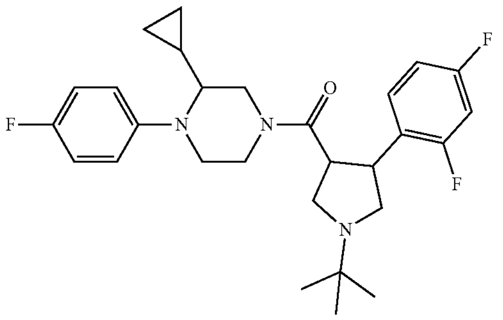
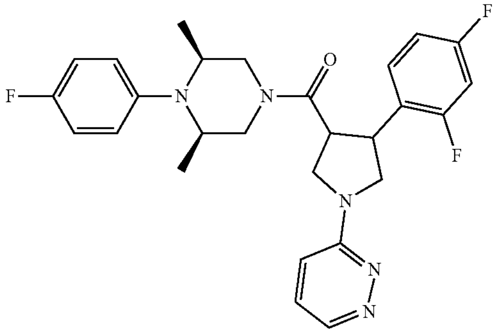
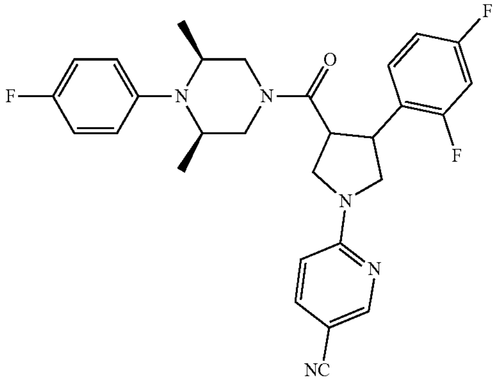
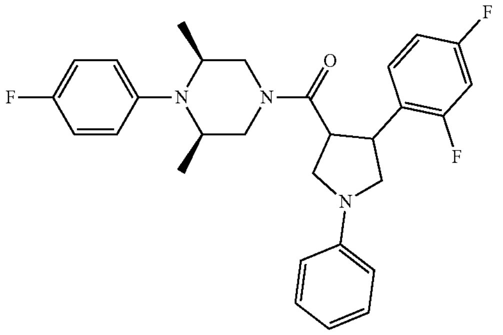
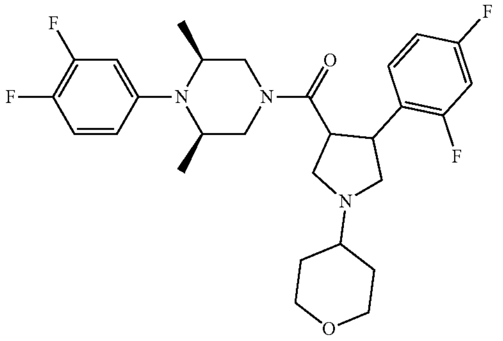
-continued
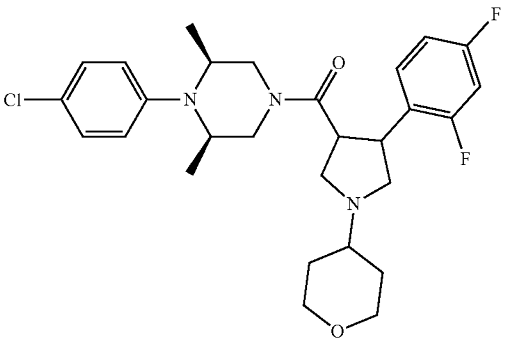
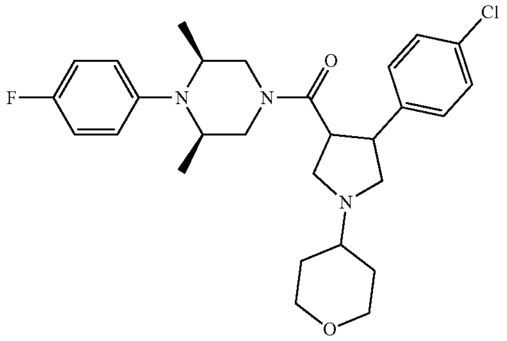
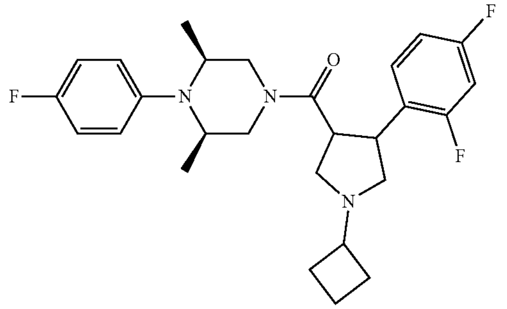
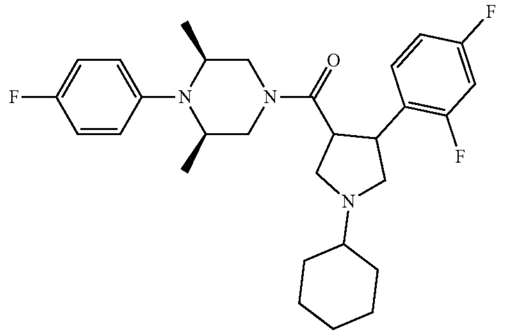
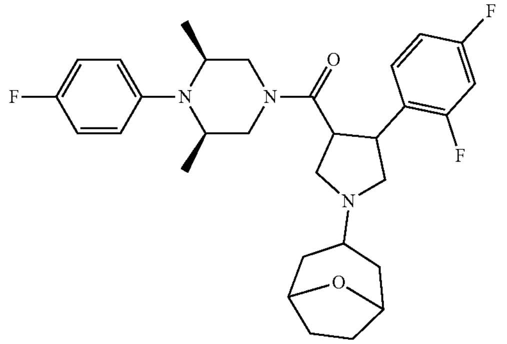

-continued
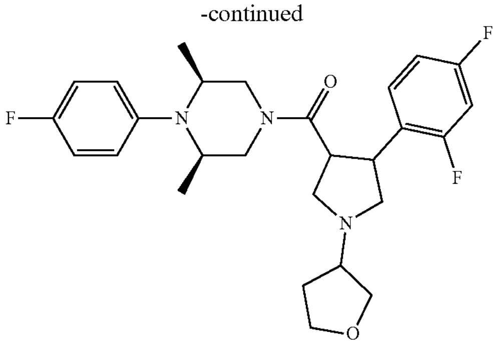
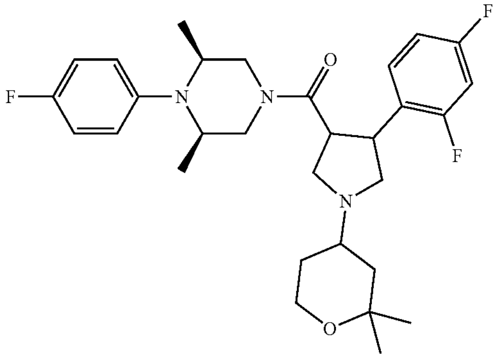
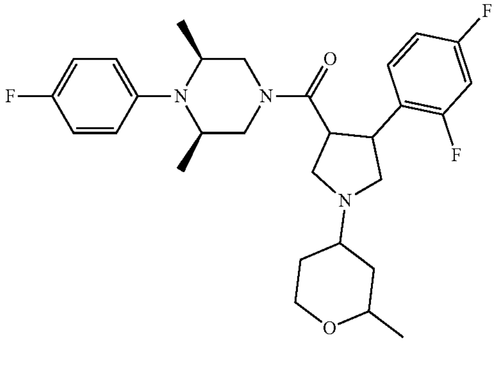
and
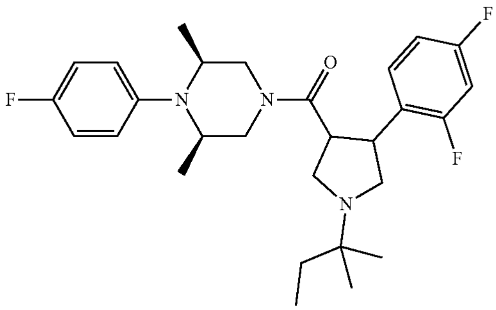 [SMILES: CCC(C)(C)N1CC(C(=O)N2C[C@@H](C)N(c3ccc(F)cc3)[C@@H](C)C2)C(c2ccc(F)cc2F)C1]
or pharmaceutically acceptable salts thereof.
12. The compound or pharmaceutically acceptable salts thereof according to claim 11, wherein the compound is selected from the group consisting of:
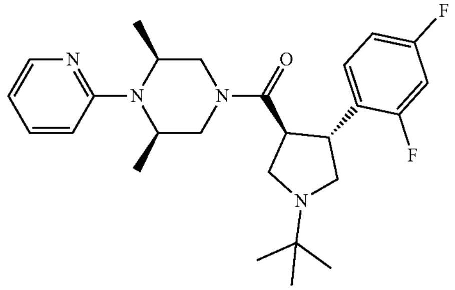
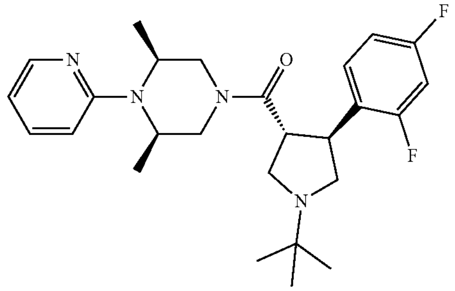
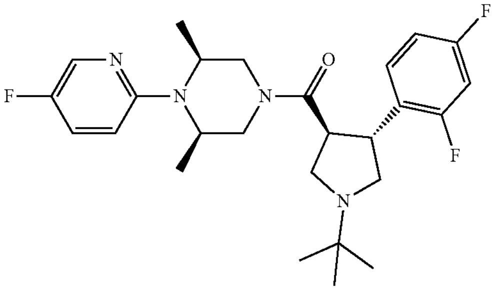
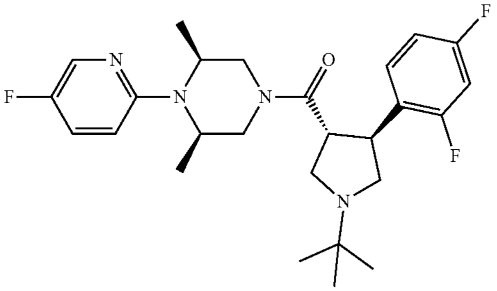
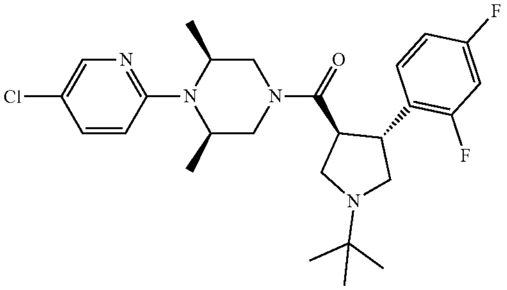
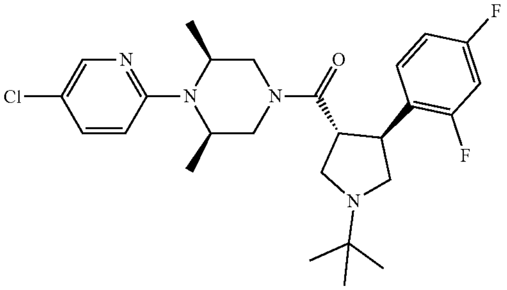

-continued
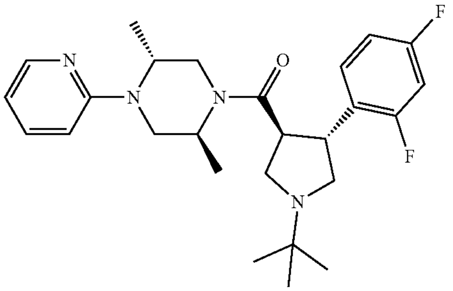
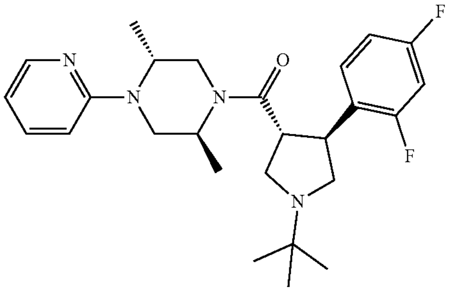
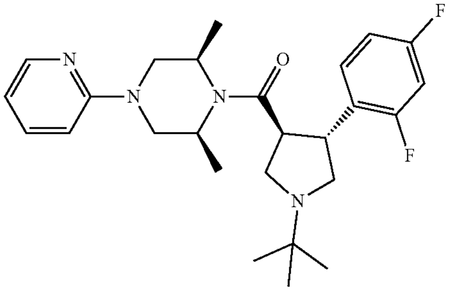
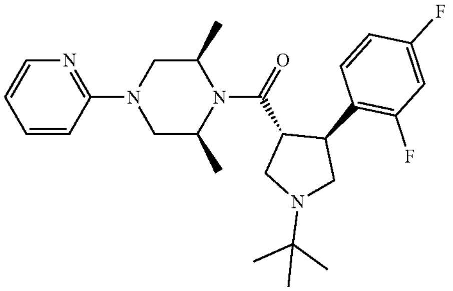
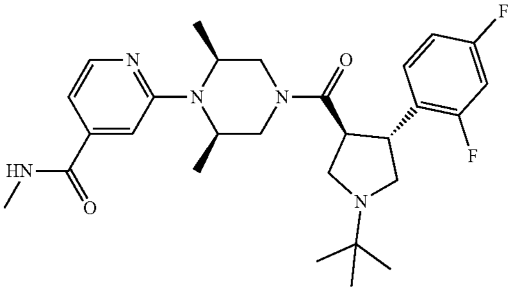
-continued
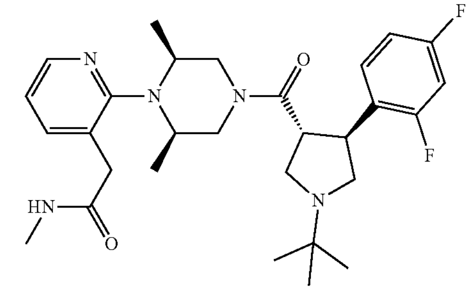
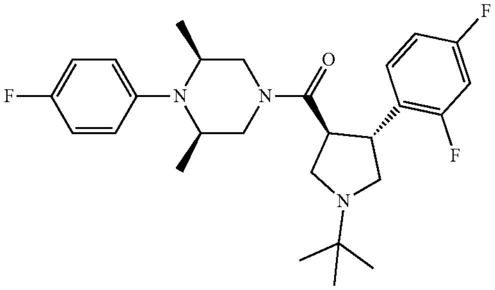
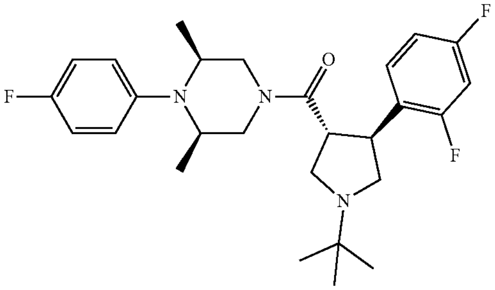
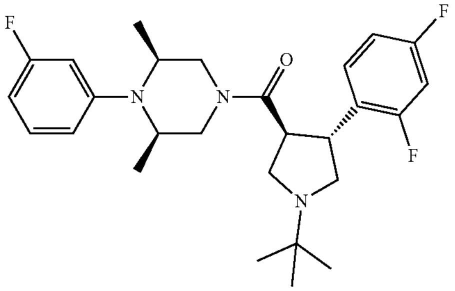
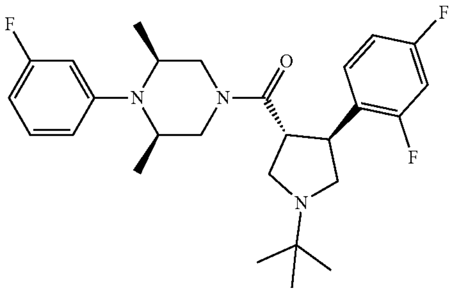

-continued
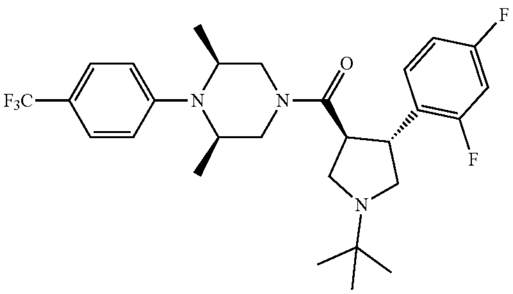
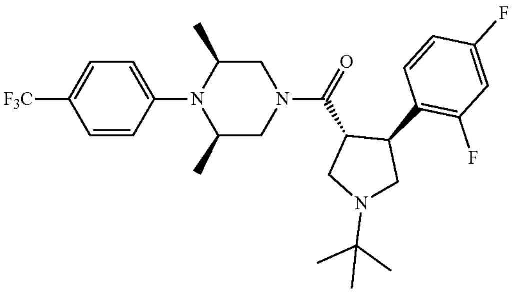
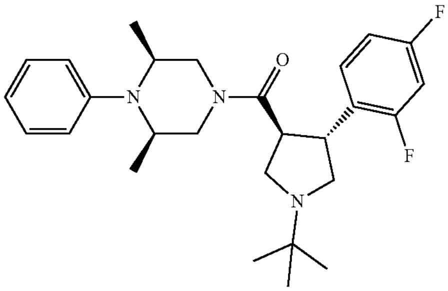
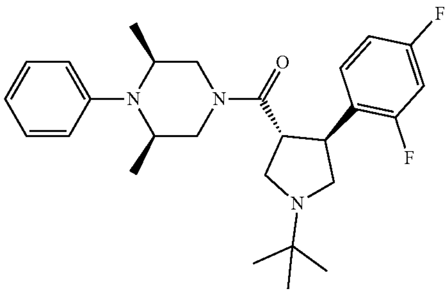
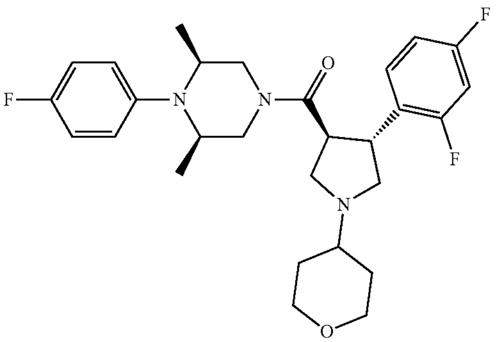
-continued
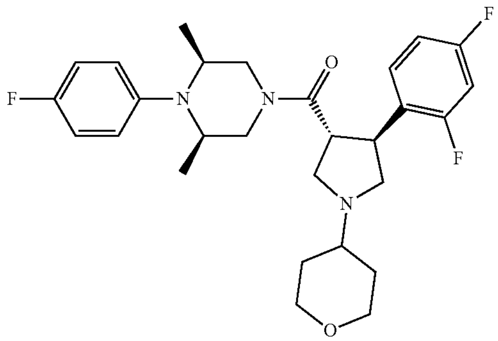
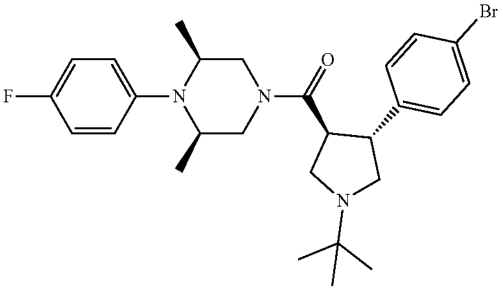
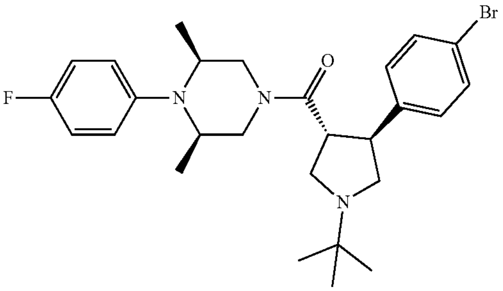
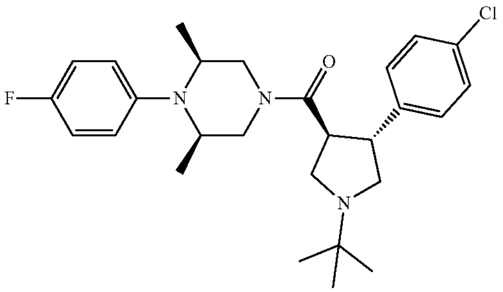
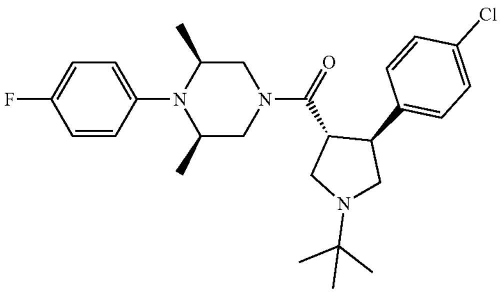

-continued
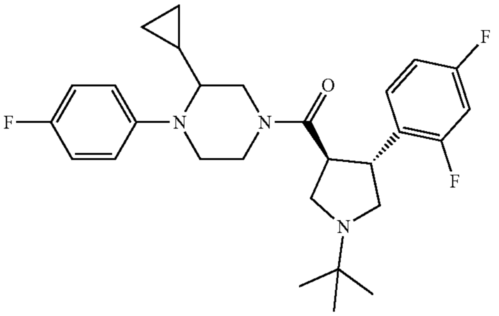
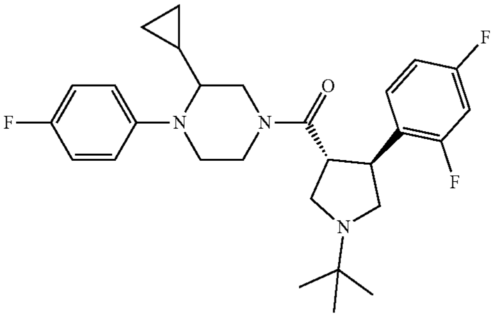
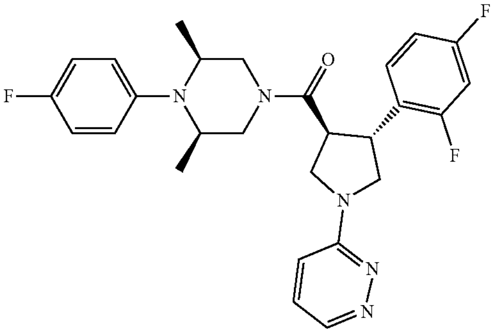
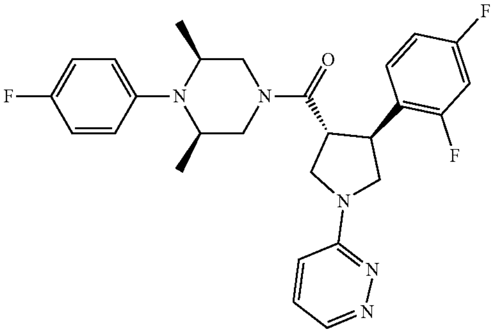
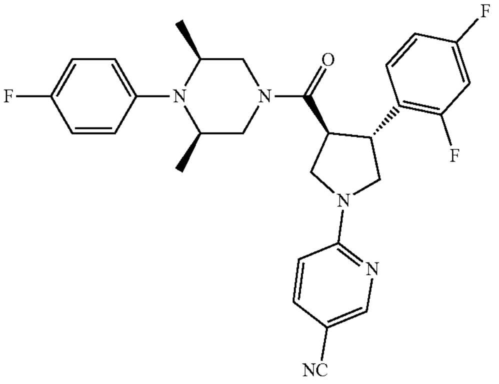
-continued
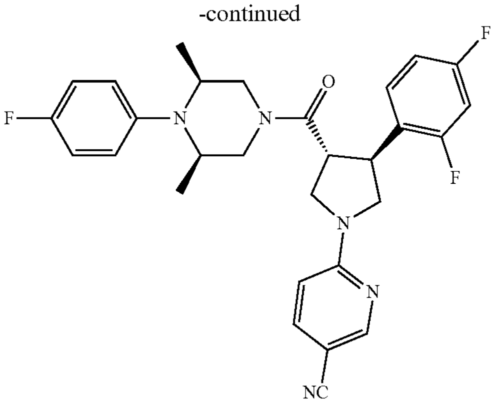
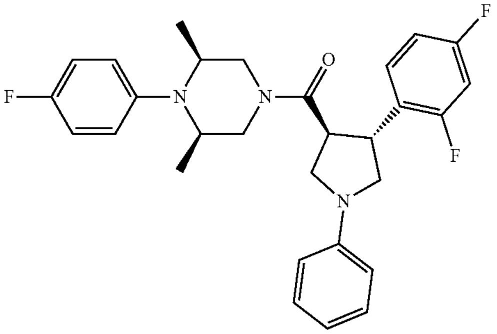
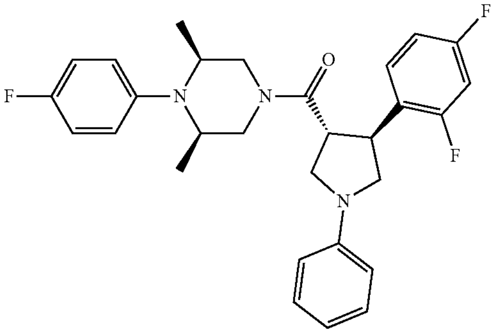
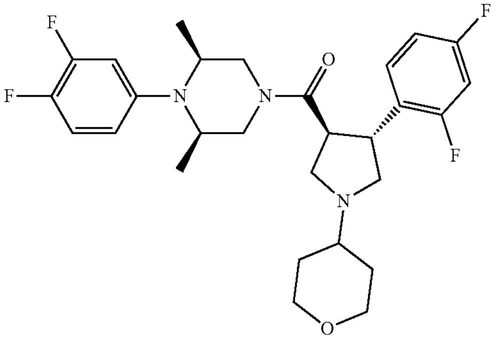
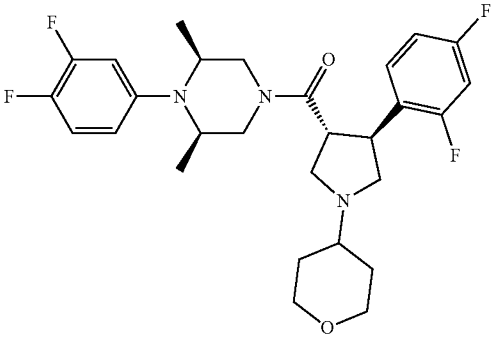

-continued
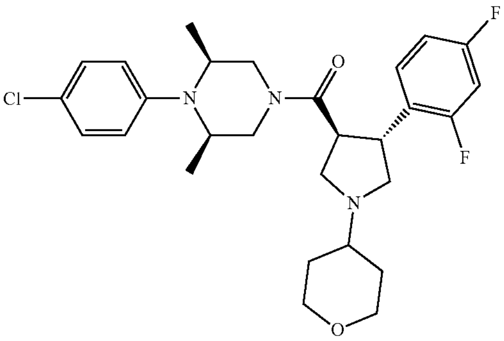
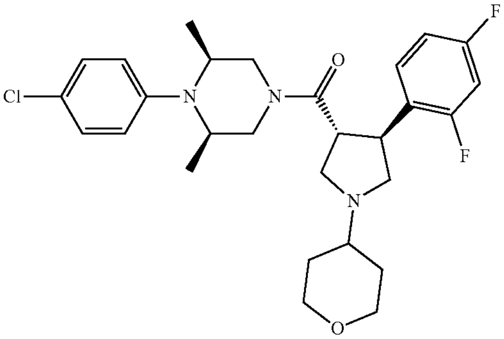
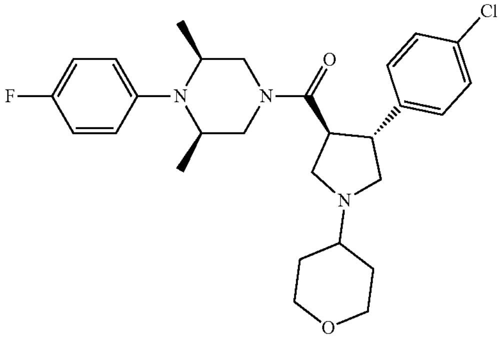
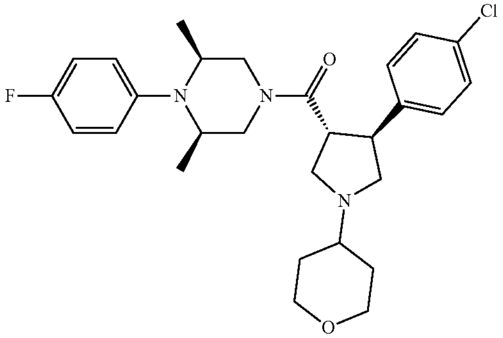
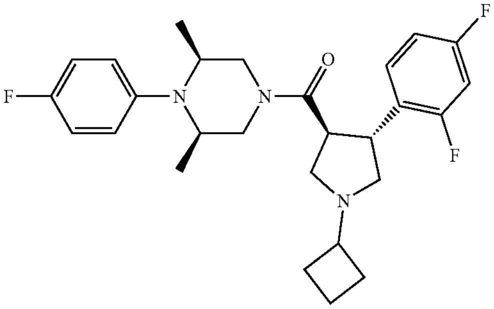
-continued
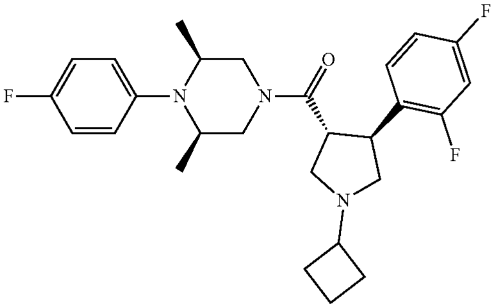
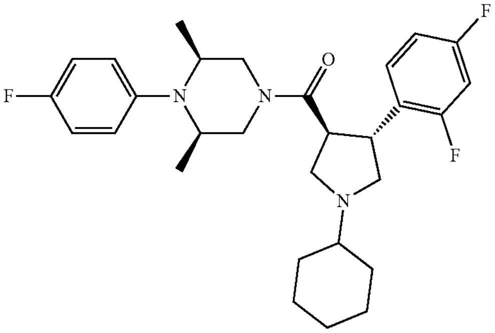
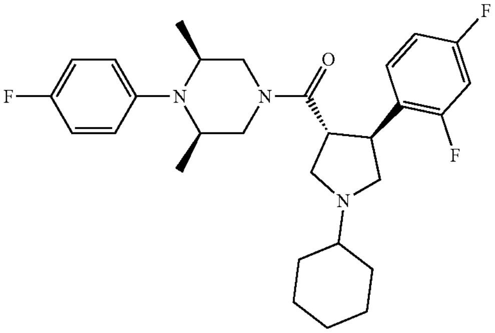
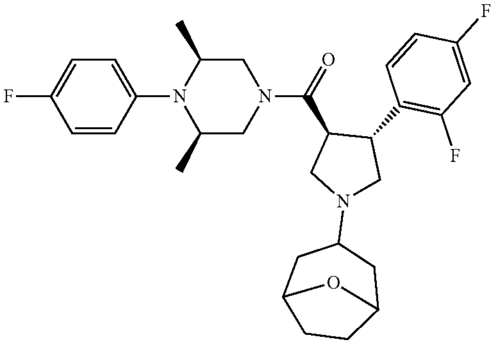
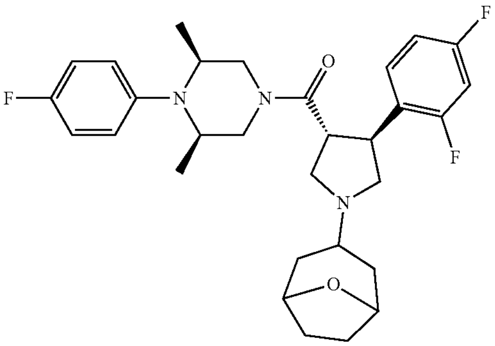

-continued
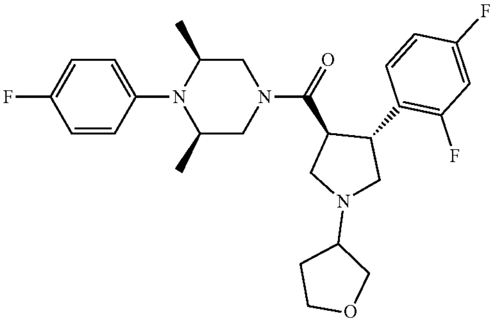
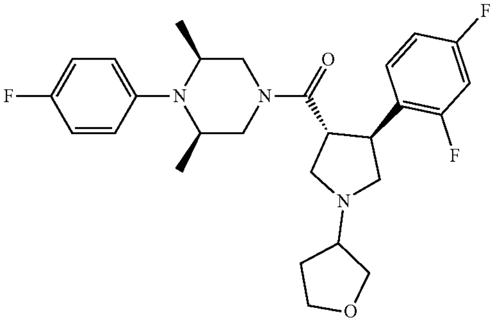
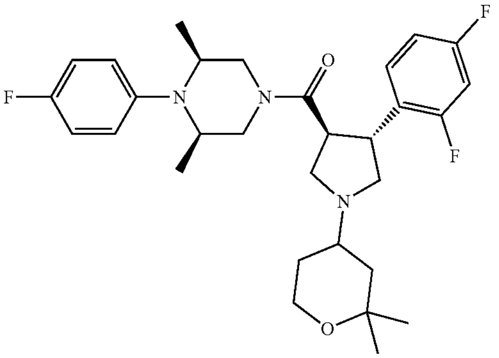
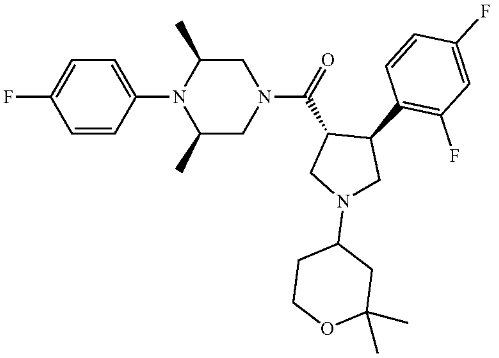
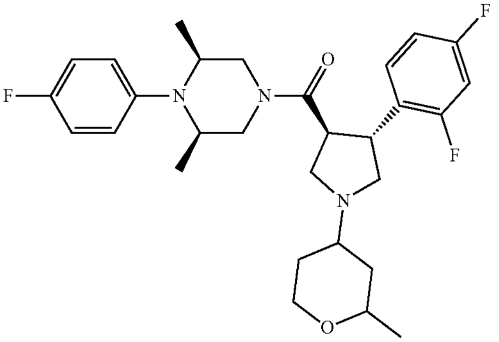
-continued
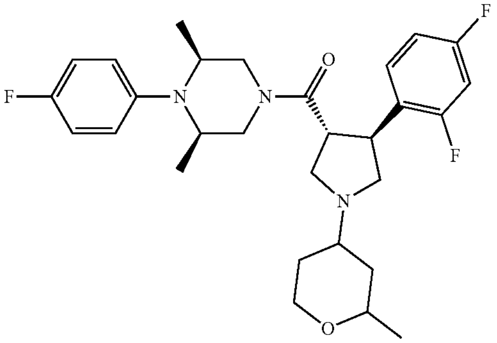
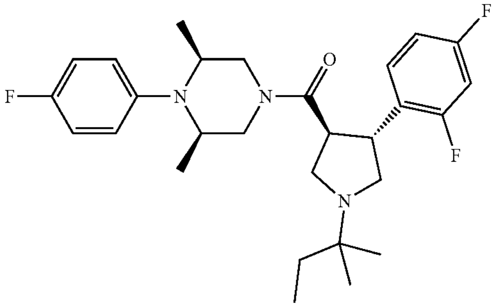
and
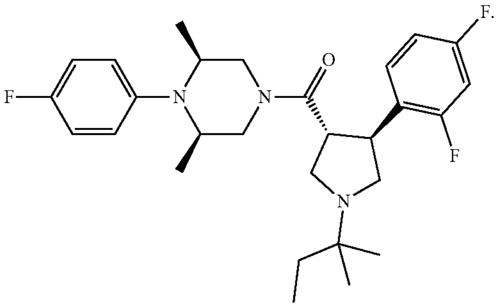 [SMILES: CCC(C)(C)N1C[C@H](C(=O)N2C[C@@H](C)N(c3ccc(F)cc3)[C@@H](C)C2)[C@@H](c2ccc(F)cc2F)C1]
13. The compound or pharmaceutically acceptable salts thereof according to claim 12, wherein the compound is selected from the group consisting of:
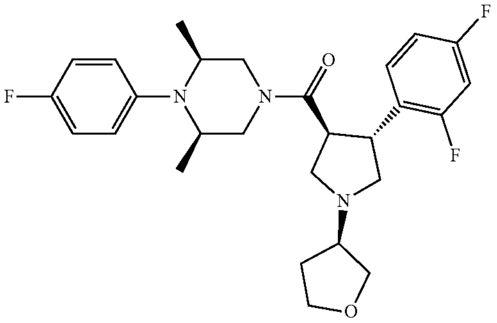

-continued
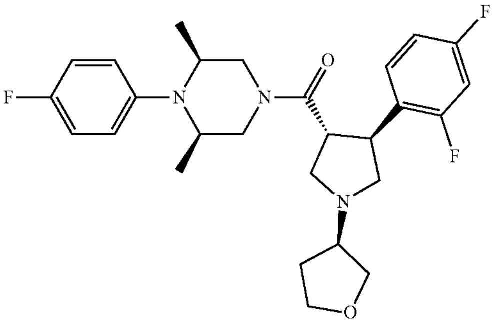
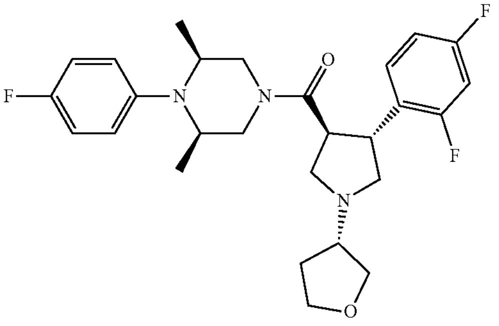
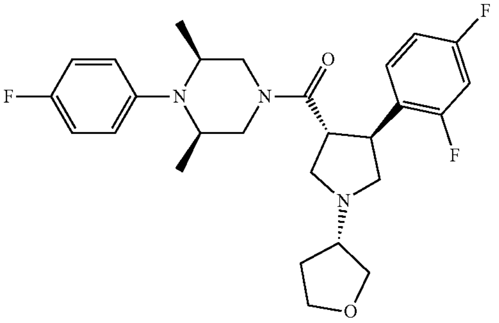
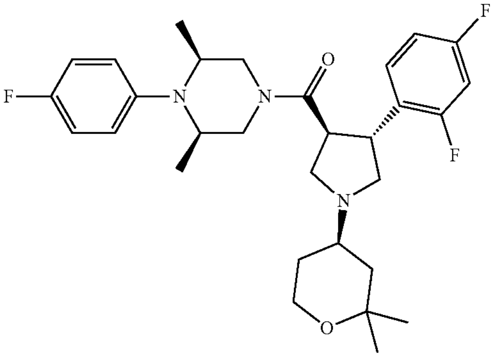
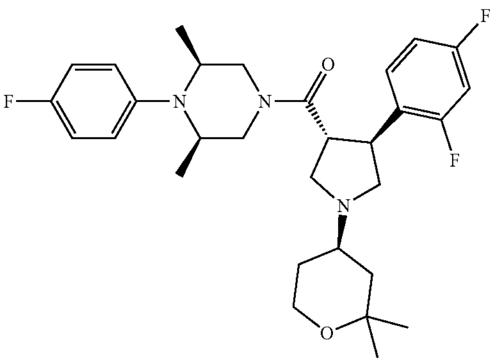
-continued
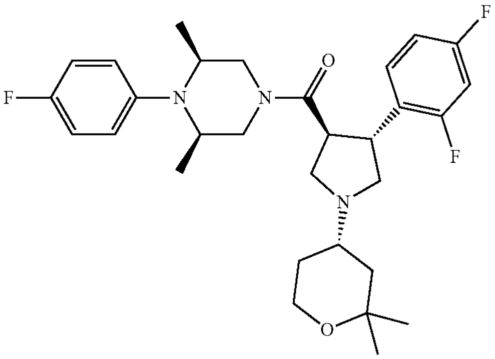
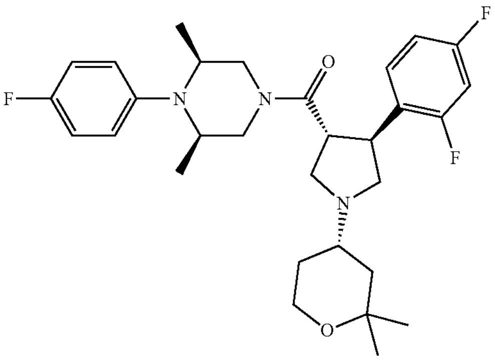
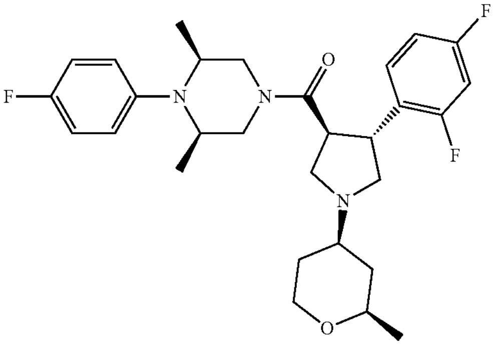
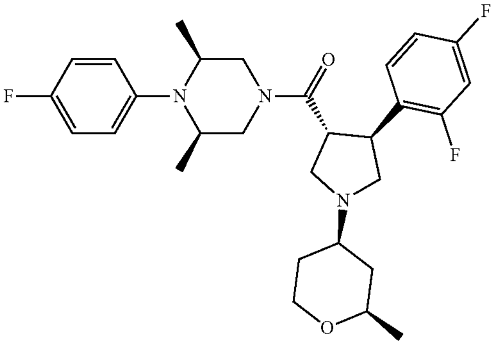

-continued

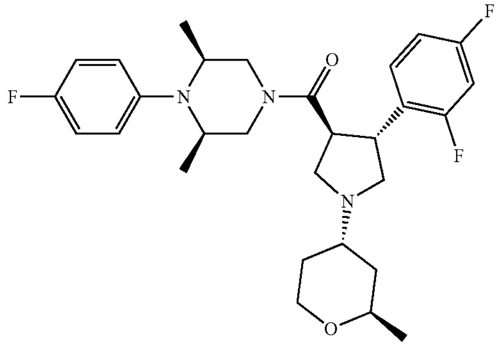

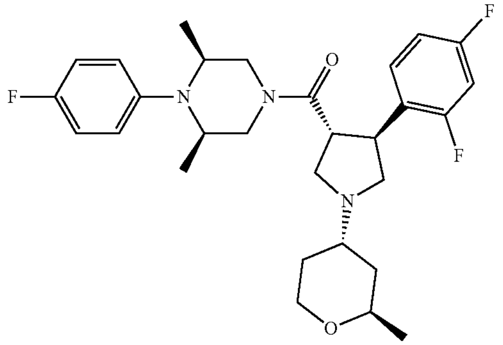

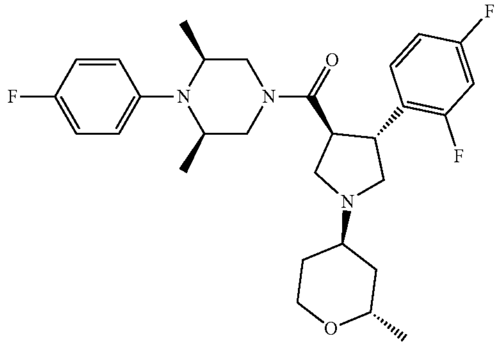

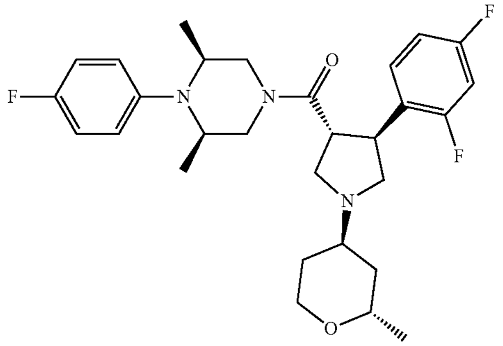

-continued

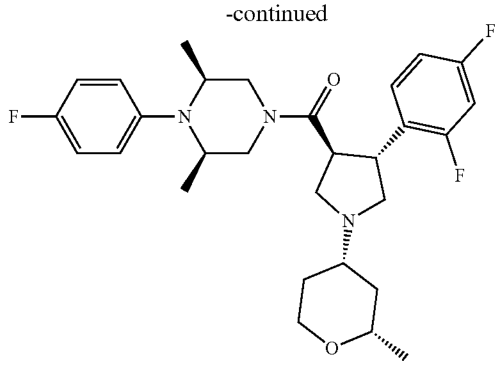

and

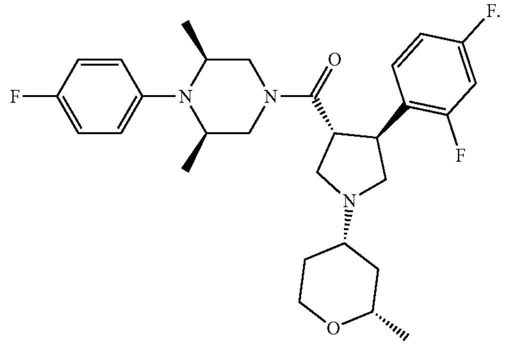 [SMILES: C[C@@H]1CN(C(=O)[C@H]2CN([C@H]3CCO[C@@H](C)C3)C[C@@H]2c2ccc(F)cc2F)C[C@H](C)N1c1ccc(F)cc1]

14. A method of treating a MC4R agonist-related disease in a subject in need thereof, comprising: administrating the compound or pharmaceutically acceptable salts thereof according to claim 1 to the subject.

15. The method according to claim 14, wherein the MC4R agonist-related disease is selected from the group consisting of male erectile dysfunction and female sexual desire disorder.

16. A method of treating a MC4R agonist-related disease in a subject in need thereof, comprising: administrating the compound or pharmaceutically acceptable salts thereof according to claim 11 to the subject.

17. The method according to claim 16, wherein the MC4R agonist-related disease is selected from the group consisting of male erectile dysfunction and female sexual desire disorder.

* * * * *